(12) United States Patent
Hillen et al.

(10) Patent No.: US 7,541,446 B2
(45) Date of Patent: Jun. 2, 2009

(54) TET REPRESSOR-BASED TRANSCRIPTIONAL REGULATORY PROTEINS

(75) Inventors: Wolfgang Hillen, Erlangen (DE);
Hermann Bujard, Heidelberg (DE);
Stefanie Urlinger, Nuremberg (DE)

(73) Assignee: Tet Systems Holding GmbH & Co. KG, Heidelberg (DE)

( * ) Notice: Subject to any disclaimer, the term of this patent is extended or adjusted under 35 U.S.C. 154(b) by 349 days.

(21) Appl. No.: 10/456,395

(22) Filed: Jun. 5, 2003

(65) Prior Publication Data

US 2003/0208783 A1 Nov. 6, 2003

Related U.S. Application Data

(63) Continuation of application No. 09/587,657, filed on Jun. 5, 2000, now abandoned.

(60) Provisional application No. 60/137,986, filed on Jun. 7, 1999.

(51) Int. Cl.
*C07H 21/04* (2006.01)
*C12N 15/63* (2006.01)

(52) U.S. Cl. .................... 536/23.1; 536/23.4; 536/24.1; 435/69.1; 435/320.1; 424/93.21

(58) Field of Classification Search ........................ None
See application file for complete search history.

(56) References Cited

U.S. PATENT DOCUMENTS

| 5,464,758 A | 11/1995 | Gossem et al. |
| 5,849,576 A | 12/1998 | Skerra et al. |
| 5,851,796 A | 12/1998 | Schatz |
| 5,917,122 A * | 6/1999 | Byrne .......................... 800/18 |
| 6,004,941 A | 12/1999 | Bujard et al. |
| 6,114,148 A | 9/2000 | Seed et al. |

FOREIGN PATENT DOCUMENTS

| DE | 19851413 A1 | 5/2000 |
| DE | 19851415 A1 | 5/2000 |
| WO | WO 96/40892 | 12/1996 |

OTHER PUBLICATIONS

Freundlieb et al, J Gene Med; 1999:1:4-12.*
Wells et al, Transgenic Res 1999;8:371-81.*
Urlinger et al, PNAS 2000;97:7963-8.*
Kamper et al, FEBS lett 2002;517:115-20.*
Krueger et al, Gene 2004:331:125-31.*
Baron, U., et al., "Tetracycline-controlled transcription in eukaryotes: novel transactivators with graded transactivation potential," *Nucleic Acids Res.* Jul. 15, 1997;25(14):2723-9.
Baron, U., et al., "Generation of conditional mutants in higher eukaryotes by switching between the expression of two genes," *Proc Natl Acad Sci U S A.* Feb. 2, 1999;96(3):1013-8.
Belli, G., et al., "Functional analysis of yeast essential genes using a promoter-substitution cassette and the tetracycline-regulatable dual expression system," *Yeast.* Sep. 15, 1998;14(12):1127-38.
Belli, G., et al., "An activator/repressor dual system allows tight tetracycline-regulated gene expression in budding yeast," *Nucleic Acids Res.* Feb. 15, 1998;26(4):942-7.
Bello, B., et al., "Spatial and temporal targeting of gene expression in *Drosophila* by means of a tetracycline-dependent transactivator system," *Development.* Jun. 1998;125(12):2193-202.
Bieschke, E.T., et al., "Doxycycline-induced transgene expression during *Drosophila* development and aging," *Mol Gen Genet.* Jun. 1998;258(6):571-9.
Camacho-Vanegas, O., et al., "Construction of *Xenopus* (B3.2) and human (HeLa) cell lines expressing the tetracycline-controlled transactivator," In Vitro *Cell Dev Biol Anim.* Jan. 1998;34(1):14-5.
Colomina, N., et al., "G1 cyclins block the lme1 pathway to make mitosis and meiosis incompatible in budding yeast," *EMBO J.* Jan. 15, 1999;18(2):320-9.
Deonarain, et al., "Ligand-targeted receptor-mediated vector for gene delivery," *Exp. Opin. Ther. Patents.* 1998; 8:53-59.
Eck, et al., "Gene-Based Therapy," Goodman & Gillman's. 1995; 9:77-101.
Efrat, S., et al., "Conditional transformation of a pancreatic beta-cell line derived from transgenic mice expressing a tetracycline-regulated oncogene," *Proc Natl Acad Sci U S A.* Apr. 11, 1995;92(8):3576-80.
Ewald, D., et al., "Time-sensitive reversal of hyperplasia in transgenic mice expressing SV40 T antigen," *Science.* Sep. 6, 1996;273(5280):1384-6.
Fishman, G.I., et al., "Tetracycline-regulated cardiac gene expression in vivo," *J Clin Invest.* Apr. 1994;93(4):1864-8.
Foster, K., et al., "Tetracycline-inducible expression systems with reduced basal activity in mammalian cells." *Nucleic Acids Research.* 1999;27(2):708-10.
Freundlieb, S., et al., "Use of tetracycline-controlled gene expression systems to study mammalian cell cycle," *Methods Enzymol.* 1997;283:159-73.
Furth, P.A., et al., "Temporal control of gene expression in transgenic mice by a tetracycline-responsive promoter," *Proc Natl Acad Sci U S A.* Sep. 27, 1994;91(20):9302-6.
Gallego, C., et al., "The Cln3 cyclin is down-regulated by translational repression and degradation during the G1 arrest caused by nitrogen deprivation in budding yeast," *EMBO J.* Dec. 1, 1997;16(23):7196-206.
Gari, E., et al., "A set of vectors with a tetracycline-regulatable promoter system for modulated gene expression in *Saccharomyces cerevisiae*," *Yeast.* Jul. 1997;13(9):837-48.
Gatz, C., et al., "Tn10-encoded tet repressor can regulate an operator-containing plant promoter," *Proc Natl Acad Sci U S A.* Mar. 1988;85(5):1394-7.

(Continued)

*Primary Examiner*—Q. Janice Li
(74) *Attorney, Agent, or Firm*—Foley & Lardner LLP

(57) ABSTRACT

The present invention provides a panel of transcriptional activator fusion proteins which comprises both tetracycline controlled transactivator proteins and reverse tetracycline transactivator proteins. These transactivators have novel phenotypes such as altered basal transcriptional activity in the absence of doxycycline, altered induced transcriptional activity in the presence of doxycycline, or differential induction by tetracycline and analogs of tetracycline.

13 Claims, 9 Drawing Sheets

OTHER PUBLICATIONS

Gossen, M., et al., "Tight control of gene expression in mammalian cells by tetracycline-responsive promoters," *Proc Natl Acad Sci U S A*. Jun. 15, 1992;89(12):5547-51.

Gossen, M., et al., "Transcriptional activation by tetracyclines in mammalian cells," *Science*. Jun. 23, 1995;268(5218):1766-9.

Harding, T.C., et al., "Switching transgene expression in the brain using an adenoviral tetracycline-regulatable system," *Nat Biotechnol*. Jun. 1998;16(6):553-5.

Harvey, et al., "Inducib le control of gene expression: prospects for gene therapy," *Chemical Biology*. 1998; 2:512-518.

Hecht, B., et al., "Noninducible Tet repressor mutations map from the operator binding motif to the C terminus," *J Bacteriol*. Feb. 1993;175(4):1206-10.

Helbl, V., et al., "Stepwise selection of TetR variants recognizing tet operator 4C with high affinity and specificity," *J Mol Biol*. Feb. 20, 1998;276(2):313-8.

Helbl, V., et al., "Stepwise selection of TetR variants recognizing tet operator 6C with high affinity and specificity," *J Mol Biol*. Feb. 20, 1998;276(2):319-24.

Hillen, W., et al., "Mechanisms underlying expression of Tn10 encoded tetracycline resistance," *Annu Rev Microbiol*. 1994;48:345-69.

Hinrichs, W., et al., "Structure of the Tet repressor-tetracycline complex and regulation of antibiotic resistance," *Science*. Apr. 15, 1994;264(5157):418-20.

Kisker, C., et al., "The complex formed between Tet repressor and tetracycline-Mg2+ reveals mechanism of antibiotic resistance," *J Mol Biol*. Mar. 24, 1995;247(2):260-80.

Kistner, A., et al., "Doxycycline-mediated quantitative and tissue-specific control of gene expression in transgenic mice," *Proc Natl Acad Sci U S A*. Oct. 1, 1996;93(20):10933-8.

Muller, G., et al., "Characterization of non-inducible Tet repressor mutants suggests conformational changes necessary for induction," *Nat Struct Biol*. Aug. 1995;2(8):693-703.

Nagahashi, S., et al., "Isolation of *Candida glabrata* homologs of the *Saccharomyces cerevisiae* KRE9 and KNH1 genes and their involvement in cell wall beta-1,6-glucan synthesis," *J Bacteriol*. Oct. 1998;180(19):5020-9.

Nakayama, H., et al., "A controllable gene-expression system for the pathogenic fungus *Candida glabrata*," *Microbiology*. Sep. 1998;144 ( Pt 9):2407-15.

Niedenthal, R.K., et al., "Green fluorescent protein as a marker for gene expression and subcellular localization in budding yeast," *Yeast*. Jun. 30, 1996;12(8):773-86.

Oldenburg, K.R., et al., "Recombination-mediated PCR-directed plasmid construction in vivo in yeast," *Nucleic Acids Res*. Jan. 15, 1997;25(2):451-2.

Orth, P., et al., "Conformational changes of the Tet repressor induced by tetracycline trapping," *J Mol Biol*. Jun. 5, 1998;279(2):439-47.

Paulus, W., et al., "Regulated expression of the diphtheria toxin A gene in human glioma cells using prokaryotic transcriptional control elements," *J Neurosurg*. Jul. 1997;87(1):89-95.

Schnappinger, D., et al., "Determinants of protein-protein recognition by four helix bundles: changing the dimerization specificity of Tet repressor," *EMBO J*. Jan. 15, 1998;17(2):535-43.

Shockett, P., et al., "A modified tetracycline-regulated system provides autoregulatory, inducible gene expression in cultured cells and transgenic mice," *Proc Natl Acad Sci USA*. Jul. 3, 1995;92(14):6522-6.

Verma, et al., "Gene therapy-promises, problems and prospects," *Nature*. Sep. 18, 1997; 389:239-242.

Wach, A., et al., "Heterologous HIS3 marker and GFP reporter modules for PCR-targeting in *Saccharomyces cerevisiae*," *Yeast*. Sep. 15, 1997;13(11):1065-75.

Weinmann, P., et al., "A chimeric transactivator allows tetracycline-responsive gene expression in whole plants," *Plant J*. Apr. 1994;5(4):559-69.

Wissmann, A., et al., "Selection for Tn10 tet repressor binding to tet operator in *Escherichia coli*: isolation of temperature-sensitive mutants and combinatorial mutagenesis in the DNA binding motif," *Genetics*. Jun. 1991;128(2):225-32.

Zeidler, M., et al., "Tetracycline-regulated reporter gene expression in the moss *Physcomitrella patens*," *Plant Mol Biol*. Jan. 1996;30(1):199-205.

Zink, et al., "Mammalian genome organization and its implications for the development of gene therapy vectors," *Gene Ther. Mol. Biol*. Jan. 2001; 6:1-24.

\* cited by examiner

Sequence of the rtTA gene (SEQ ID NO:22)

ATGTCTAGATTAGATAAAAGTAAAGTGATTAACAGCGCATTAGAGCTGCTTAATG
AGGTCGGAATCGAAGGTTTAACAACCCGTAAACTCGCCCAGAAGCTtGGTGTAGA
GCAGCCTACAcTGTATTGGCATGTAAAAAATAAGCGGGCTTTGCTCGACGCCTTA
GCCATTGAGATGTTAGATAGGCACCATACTCACTTTTGCCCTTTAaAAGGGGAAA
GCTGGCAAGATTTTTTACGcAATAACGCTAAAAGTTTTAGATGTGCTTTACTAAGT
CATCGCaATGGAGCAAAAGTACATTcAGaTACACGGCCTACAGAAAAACAGTATG
AAACTCTCGAAAATCAATTAGCCTTTTTATGCCAACAAGGTTTTTCACTAGAGAAc
GCgTTATATGCACTCAGCGCTGTGGGGCATTTTACTTTAGGTTGCGTATTGGAAGA
TCAAGAGCATCAAGTCGCTAAAGAAGAAAGGGAAACACCTACTACTGATAGTAT
GCCGCCATTATTACGACAAGCTATCGAATTATTTGATCACCAAGGTGCAGAGCCA
GCCTTCTTATTCGGCCTTGAATTGATCATATGCGGATTAGAAAAACAACTTAAAT
GTGAAAGTGGGTCcgcgtacagccgcgcgcgtacgaaaaacaattacgggtctaccatcgagggcctgctcgatctcccg
gacgacgacgcccccgaagaggcggggctggcggctccgcgcctgtcctttctccccgcgggacacacgcgcagactgtcgacgg
ccccccgaccgatgtcagcctgggggacgagctccacttagacggcgaggacgtggcgatggcgcatgccgacgcgctagacgat
ttcgatctggacatgttgggggacggggattccccgggtccgggatttaccccccacgactccgcccctacggcgctctggatatggc
cgacttcgagtttgagcagatgtttaccgatgcccttggaattgacgagtacggtgggtag

FIGURE 8

Sequence of the tTA gene (SEQ ID NO: 24)

ATGTCTAGATTAGATAAAAGTAAAGTGATTAACAGCGCATTAGAGCTGCTTAATG
AGGTCGGAATCGAAGGTTTAACAACCCGTAAACTCGCCCAGAAGCTAGGTGTAG
AGCAGCCTACATTGTATTGGCATGTAAAAAATAAGCGGGCTTTGCTCGACGCCTT
AGCCATTGAGATGTTAGATAGGCACCATACTCACTTTTGCCCTTTAGAAGGGGAA
AGCTGGCAAGATTTTTTACGTAATAACGCTAAAAGTTTTAGATGTGCTTTACTAA
GTCATCGCGATGGAGCAAAAGTACATTTAGGTACACGGCCTACAGAAAAACAGT
ATGAAACTCTCGAAAATCAATTAGCCTTTTTATGCCAACAAGGTTTTTCACTAGA
GAATGCATTATATGCACTCAGCGCTGTGGGGCATTTTACTTTAGGTTGCGTATTG
GAAGATCAAGAGCATCAAGTCGCTAAAGAAGAAAGGGAAACACCTACTACTGAT
AGTATGCCGCCATTATTACGACAAGCTATCGAATTATTTGATCACCAAGGTGCAG
AGCCAGCCTTCTTATTCGGCCTTGAATTGATCATATGCGGATTAGAAAAACAACT
TAAATGTGAAAGTGGGTCcgcgtacagccgcgcgcgtacgaaaaacaattacgggtctaccatcgagggcctgctc
gatctcccggacgacgacgcccccgaagaggcggggctggcggctccgcgcctgtcctttctccccgcgggacacacgcgcagact
gtcgacggccccccgaccgatgtcagcctgggggacgagctccacttagacggcgaggacgtggcgatggcgcatgccgacgcg
ctagacgatttcgatctggacatgttgggggacggggattccccgggtccgggatttaccccccacgactccgcccccctacggcgctct
ggatatggccgacttcgagtttgagcagatgtttaccgatgcccttggaattgacgagtacggtgggtag

FIGURE 9

TET REPRESSOR-BASED TRANSCRIPTIONAL REGULATORY PROTEINS

RELATED APPLICATIONS

This application claims priority to U.S. application Ser. No. 09/587,657, filed on Jun. 5, 2000, which claims priority to U.S. Provisional Application No. 60/137,986, filed on Jun. 7, 1999, the contents of which are incorporated herein in their entirety by this reference.

BACKGROUND OF THE INVENTION

The Tn10-encoded Tet repressor (TetR) protein regulates the expression of tetracycline resistance genes in gram negative bacteria, e.g., *Escherichia coli*, in a tetracycline (Tc) dependent fashion (reviewed in Hillen & Berens, 1994). In the absence of Tc, a TetR protein dimer binds to operator sequences (tetO) and inhibits expression of the tetracycline resistance gene (tetA). When the inducer Tc enters the cell and binds to TetR, the affinity for tetO is reduced and TetR dissociates from tetO, allowing expression of tetA. The crystal structures of the TetR-[Mg—Tc]$^+$ complex (Hinrichs et al., 1994; Kisker et al., 1995) and free TetR (Orth et al., 1998), and analysis of non-inducible TetR mutants (Müller et al., 1995), imply that the binding of Tc induces conformational changes in TetR. Dimerization of TetR is mediated by a four helix bundle, and residues which determine the dimerization specificity have been identified (Schnappinger et al, 1998). This has led to TetR based regulators which cannot heterodimerize.

TetR-based transcription activators have been developed which allow inducible expression of appropriately modified genes in a tetracycline dependent mode (Gossen & Bujard, 1992; Gossen et al, 1995) in various cellular systems of mammalian (Gossen & Bujard, 1992), plant (Weinmann et al, 1994; Zeidler et al, 1996) and amphibian (Camacho-Vanegas et al., 1998) origin, as well as in whole organisms including fungi (Gari et al., 1997), plants (Weinmann et al., 1994), *Drosophila* (Bello et al., 1998), mice (Kistner et al., 1996; Efrat et al., 1995; Ewald et al., 1996) and rats (Fishman et al., 1994; Harding et al., 1998).

Tetracycline controlled transactivators (tTA) are fusions between TetR and proper domains of transcriptional activators. In one such fusion protein, a major portion of the Herpes simplex virus protein 16 (VP16) was fused at the level of DNA to TetR. Yet, other tTA's demonstrate a graded transactivation potential resulting from connecting different combinations of minimal activation domains to the C-terminus of TetR (Baron et al., 1997). These chimeric "tetracycline controlled transactivators" (tTA) allow one to regulate the expression of genes placed downstream of minimal promoter-tetO fusions ($P_{tet}$). In absence of Tc $P_{tet}$ is activated whereas in presence of the antibiotic activation of $P_{tet}$ is prevented.

A "reverse tetracycline controlled transactivator" (rtTA) was developed which binds operator DNA only in the presence of some tetracycline derivatives such as doxycycline (Dox) or anhydrotetracycline (ATc), and thus activates $P_{tet}$ upon addition of Dox (Gossen et al., 1995). Both tTA and rtTA are widely used to regulate gene expression in various systems (for review see Freundlieb et al., 1997).

Despite widespread use of Tet systems in academic and industrial research, as well as in some technical processes such as high throughput screening and fermentation, there are limitations which prevent their use in a number of areas because of the specific properties of the transactivators, and of the inducing effector substances. These limitations concern particularly:

the residual affinity of rtTA to tetO sequences in the absence of the inducer;

the relatively low susceptibility of rtTA towards Dox;

the interdependence between different domains of tTA and rtTA, that can affect the specificity of transactivator/operator interaction;

the stability of tTA and rtTA in different eukaryotic systems;

the relatively narrow temperature optimum of tTA/rtTA function;

the antibiotic activity of some of the best effector molecules; and the restriction of effectors to substances of the tetracycline family.

For example, the known rtTA described above has retained a residual affinity to tetO in the absence of doxycycline (Dox). This can lead to an intrinsic basal activity of rtTA responsive promoters, and indeed such increased basal levels of transcription have been observed in mammalian cell lines as well as in *S. cerevisiae*. Tc controlled expression using tTA and rtTA in *S. cerevisiae* has been published (Gallego et al., 1997; Gan et al., 1997; Belli et al., 1998a; Belli et al., 1998b; Nagahashi et al., 1998; Nakayama et al., 1998; Colomina et al., 1999). Gene regulation was achieved with tTA showing high expression of lacZ and low basal activities (Bari et al., 1997). In contrast, rtTA did not regulate expression in response to Tc due to extremely high basal expression, leaving no room for apparent induction of gene expression. Thus, an additional regulated repressor was introduced to lower the basal expression (Belli et al., 1998). Only this dual control system previously yielded reasonable induction factors in *S. cerevisiae*. In addition, the known rtTA is fully induced only at relatively high levels of Dox.

Moreover, it appears that active rtTA proteins cannot be synthesized in a number of systems including B-cells in transgenic (tg) mice, *Drosophila melanogaster*, and plants. Whether this is due to instabilities at the level of RNA or protein, or both is not entirely clear.

The known transactivators also exhibit a rather narrow temperature optimum. In mammalian systems, this does not pose a particular problem. By contrast, applying Tet regulation to plants will require an expanded temperature tolerance of transactivators.

Previously, the most efficient way of producing TetR variants was based on random or directed mutagenesis, followed by screening procedures that relied on TetR function in *E. coli* (Helbl & Hillen, 1998; Helbl et al., 1998; Müller et al., 1995; Hecht et al., 1993; Wissmann et al., 1991). TetR variants identified in this way were subsequently converted to tTA and/or rtTA fusion proteins whose properties were examined in eukaryotic systems. Frequently, the properties of TetR variants as identified in *E. coli* would not correlate with those of the corresponding tTA or rtTAs in eukaryotic cells. The main reasons for these inconsistencies are: (a) fusion of activator domains to TetR variants or introduction of mutations, e.g., mutations that confer the reverse phenotype, may negatively affect the overall function of the respective TetR variant; (b) the properties of tTA/rtTA's such as stability or the interaction with operator sequences is affected by differences in the cellular environment between *E. coli* and various eukaryotic systems; and (c) tetracycline and many of its derivatives are toxic in prokaryotes where they act primarily to inhibit protein biosynthesis, and thus limit screening procedures to sublethal concentrations of the effector molecule. By contrast, tetracyclines are tolerated at higher concentrations in eukaryotic cells.

It is therefore necessary to examine fully the useful sequence space of the Tet repressor. To this end, it is desirable to develop a screening method which is capable of rapidly and efficiently identifying novel variants of tTA and rtTA out of large pools of candidates produced by random, semi-random and directed mutagenesis.

Optimal application of tTA's and rtTA's in different eukaryotic systems will require the development of transactivators that are specifically adapted to defined tasks. Therefore, screening systems that are capable of identifying tTA/rtTA phenotypes directly in eukaryotes like yeast or other fungi will constitute a significant improvement over the current screening technology for the following reasons:

the phenotypes identified will directly reflect the properties of the transactivating fusion protein (TetR fused to an activation domain) in an eukaryotic system;

mutagenesis can be performed throughout the gene encoding the entire transactivator;

mutations within the activation domain can be included in the analysis; and using yeast or other fungal systems will result in screening efficiencies that are comparable to those obtained in *E. coli*.

SUMMARY OF THE INVENTION

In one aspect, the invention provides an isolated polypeptide comprising a sequence variant of a reverse tetracycline controlled transactivator (rtTA) protein which has altered basal transcriptional activity in the absence of doxycycline, or an analog thereof. In another aspect, the invention provides an isolated polypeptide comprising a sequence variant of a rtTA protein which has altered induced transcriptional activity in the presence of doxycycline, or an analog thereof.

In one embodiment, the invention provides an isolated polypeptide comprising an rtTA protein having at least one amino acid mutation within the DNA binding domain. In one embodiment, the DNA binding domain comprises amino acids 1 to 45 of SEQ ID NO:23. In a preferred embodiment, the mutation is selected from the group comprising: S12G, E19G, and T26A. In yet another preferred embodiment, the mutation confers altered basal affinity for the Tet operator in the absence of doxycycline, or an analog thereof. In another embodiment, the invention provides an isolated polypeptide comprising an rtTA protein having at least one amino acid mutation within the tetracycline binding domain. In one embodiment, the tetracycline binding domain comprises amino acids 46 to 207 of SEQ ID NO:23. In a preferred embodiment, the mutation is selected from the group comprising: A56P, R87S , deletion C88, D95G, G96R, V99E, D148E, H179R, and E204K. In yet another preferred embodiment the mutation confers altered sensitivity towards doxycycline, or an analog thereof.

The invention provides an isolated polypeptide comprising a rtTA protein comprising an amino acid sequence having at least 50% homology to the amino acid sequence of SEQ ID NO:23, wherein the polypeptide has at least one amino acid mutation within the DNA binding domain. In one embodiment, the invention provides an isolated polypeptide comprising a rtTA protein comprising an amino acid sequence having at least 50% homology to the amino acid sequence of SEQ ID NO:23, wherein the polypeptide has at least one amino acid mutation within the tetracycline binding domain.

In another aspect, the invention provides an isolated polypeptide comprising a sequence variant of a tetracycline controlled transactivator (tTA) protein which displays differential regulation by tetracycline, and analogs thereof. In one embodiment, the invention is an isolated polypeptide comprising a tTA protein having at least one amino acid mutation within the tetracycline binding domain. In one embodiment, the tetracycline binding domain comprises amino acids 46 to 207 of SEQ ID NO:25. In a preferred embodiment the mutation is selected from the group comprising: A56V, F78S, S85G, S85R, Y110C, L113H, Y132C, I164L, P167S, L170V, I174V, I174T, or E183K. In yet another preferred embodiment, the mutation confers differential sensitivity towards tetracycline, or an analog thereof. In another embodiment, the invention is an isolated polypeptide comprising a tTA protein which contains at least one amino acid mutation within the DNA binding domain. In one embodiment, the DNA binding domain comprises amino acids 46 to 207 of SEQ ID NO:25.

The invention also provides an isolated polypeptide comprising a tTA protein comprising an amino acid sequence having at least 50% homology to the amino acid sequence of SEQ ID NO:25, wherein the polypeptide has at least one amino acid mutation within the tetracycline binding domain.

In one embodiment the invention provides an isolated polypeptide comprising the amino acid sequence of SEQ ID NO: 2, 4, 7, 9, 11, 13, 15, 17, 19, 21, 23, 25, 27, 29, 31, 33, 35, 37, 39, 41, 43 or 45. In another embodiment the invention provides an isolated polypeptide having at least 50% identity to the amino acid sequence comprising SEQ ID NO: 2, 4, 7, 9, 11, 13, 15, 17, 19, 21, 23, 25, 27, 29, 31, 33, 35, 37, 39, 41, 43 or 45.

Another embodiment of the invention provides an isolated polypeptide encoded by the nucleic acid sequence of SEQ ID NO: 1, 3, 5, 6, 8, 10, 12, 14, 16, 18, 20, 22, 24, 26, 28, 30, 32, 34, 36, 38, 40, 42, or 44. Another aspect of the invention provides an isolated polypeptide encoded by a polynucleotide having at least 50% identity to SEQ ID NO: 1, 3, 5, 6, 8, 10, 12, 14, 16, 18, 20, 22, 24, 26, 28, 30, 32, 34, 36, 38, 40, 42, or 44.

In one aspect, the invention provides a fusion protein comprising the polypeptides of the invention operatively linked to heterologous amino acid sequences.

In another aspect, the invention provides an isolated polynucleic acid molecule selected from the group consisting of:

(a) a polynucleotide comprising the nucleotide sequence of SEQ ID NO: 1, 5, 6, 8, 10, 12, 14, 16, 18, or 20;

(b) a polynucleotide that is antisense to the polynucleotide of (a);

(c) a polynucleotide having at least 50% identity to the polynucleotide of (a) or (b);

(d) a polynucleotide comprising a fragment of at least 100 contiguous nucleotides of a nucleic acid comprising the nucleotide sequence of SEQ ID NO: 1, 5, 6, 8, 10, 12, 14, 16, 18, or 20;

(e) a polynucleotide which encodes a polypeptide comprising the amino acid sequence of SEQ ID NO: 2, 7, 9, 11, 13, 15, 17, 19 or 21;

(f) a polynucleotide which encodes a fragment of a polypeptide comprising the amino acid sequence of SEQ ID NO: 2, 7, 9, 11, 13, 15, 17, 19 or 21, wherein the fragment comprises at least 30 contiguous amino acid residues of the amino acid sequence of SEQ ID NO: 2, 7, 9, 11, 13, 15, 17, 19 or 21;

(g) a polynucleotide which encodes a polypeptide having at least 50% identity to the polypeptide comprising the amino acid sequence of SEQ ID NO: 2, 7, 9, 11, 13, 15, 17, 19 or 21; and (h) a polynucleotide having at least 50% identity to the nucleic acid of (a)-(g) encoding a protein capable of regulating transcription from sequences derived from the tet operator.

In another aspect, the invention provides an isolated polynucleic acid molecule selected from the group consisting of:

(a) a polynucleotide comprising the nucleotide sequence of SEQ ID NO: 3, 26, 28, 30, 32, 34, 36, 38, 40, 42, or 44;

(b) a polynucleotide that is antisense to the polynucleotide of (a);

(c) a polynucleotide having at least 50% identity to the polynucleotide of (a) or (b);

(d) a polynucleotide comprising a fragment of at least 100 contiguous nucleotides of a nucleic acid comprising the nucleotide sequence of SEQ ID NO: 3, 26, 28, 30, 32, 34, 36, 38, 40, 42, or 44;

(e) a polynucleotide which encodes a polypeptide comprising the amino acid sequence of SEQ ID NO: 4, 27, 29, 31, 33, 35, 37, 39, 41, 43 or 45;

(f) a polynucleotide which encodes a fragment of a polypeptide comprising the amino acid sequence of SEQ ID NO: 4, 27, 29, 31, 33, 35, 37, 39, 41, 43 or 45, wherein the fragment comprises at least 15 contiguous amino acid residues of the amino acid sequence of SEQ ID NO: 4, 27, 29, 31, 33, 35, 37, 39, 41, 43 or 45;

(g) a polynucleotide which encodes a polypeptide having at least 50% identity to the polypeptide comprising the amino acid sequence of SEQ ID NO: 4, 27, 29, 31, 33, 35, 37, 39, 41, 43 or 45; and (h) a polynucleotide having at least 50% identity to the nucleic acid of (a)-(g) encoding a protein capable of regulating transcription from sequences derived from the tet operator.

In yet another aspect, the invention provides a nucleic acid molecule comprising a polynucleotide of the invention operably linked to nucleic acid sequences encoding a heterologous peptide.

One aspect of the invention provides a vector comprising the nucleic acid molecules of the invention. In one embodiment, the vector is an expression vector.

Another aspect of the invention provides an antibody which binds to a polypeptide of the invention.

In one embodiment, the invention provides a recombinant cell comprising the isolated polypeptides of the invention. In a further embodiment, the invention provides a recombinant cell which comprises the nucleic acid molecules of the invention. In a preferred embodiment, the invention provides a recombinant cell comprising an expression vector of the invention. In another embodiment the recombinant cell is selected from the group consisting of a eukaryotic cell, a prokaryotic cell and a virus. In a preferred embodiment the recombinant cell is selected from the group consisting of a plant cell, an insect cell, a fungal cell, a bacterial cell, or a mammalian cell.

One aspect of the invention provides a method for producing a polypeptide selected from the group consisting of:

(a) a polypeptide comprising the amino acid sequence of SEQ ID NO: 2, 4, 7, 9, 11, 13, 15, 17, 19, 21, 27, 29, 31, 33, 35, 37, 39, 41, 43 or 45;

(b) a fragment of a polypeptide comprising the amino acid sequence of SEQ ID NO: 2, 4, 7, 9, 11, 13, 15, 17, 19, 21, 27, 29, 31, 33, 35, 37, 39, 41, 43 or 45, wherein the fragment comprises at least 15 contiguous amino acid residues of the amino acid sequence of SEQ ID NO: 2, 4, 7, 9, 11, 13, 15, 17, 19, 21, 27, 29, 31, 33, 35, 37, 39, 41, 43 or 45; and (c) an allelic variant of a polypeptide comprising the amino acid sequence of SEQ ID NO: 2, 4, 7, 9, 11, 13, 15, 17, 19, 21, 27, 29, 31, 33, 35, 37, 39, 41, 43 or 45;

comprising culturing a recombinant cell containing an expression vector comprising a polynucleotide encoding a polypeptide of the present invention under conditions such that the polypeptide is expressed.

Another aspect of the invention provides a method for regulating transcription of a Tet operator-linked gene in a cell, comprising:

introducing into the cell a nucleic acid molecule encoding a fusion protein comprising the amino acid sequence of SEQ ID NO: 2, 4, 7, 9, 11, 13, 15, 17, 19, 21, 27, 29, 31, 33, 35, 37, 39, 41, 43 or 45; and modulating the concentration of tetracycline, or an analog thereof, in contact with the cell.

A further aspect of the invention provides a method for producing a protein encoded by a gene whose expression is regulated by sequences derived from the tet operator in a cell, comprising:

introducing into the cell a nucleic acid molecule encoding a fusion protein comprising the amino acid sequence of SEQ ID NO2, 4, 7, 9, 11, 13, 15, 17, 19, 21, 27, 29, 31, 33, 35, 37, 39, 41, 43 or 45; and modulating the concentration of tetracycline, or an analog thereof, in contact with the cell, such that the protein is produced.

In yet another aspect, the invention provides non-human transgenic organisms. One embodiment of the invention is a non-human transgenic organism comprising a transgene comprising a nucleic acid molecule of the invention in a form suitable for expression of a rtTA protein in cells of the non-human transgenic organism. Another embodiment of the invention is a non-human transgenic organism comprising a transgene comprising the nucleic acid molecule of the invention in a form suitable for expression of a tTA protein in cells of the non-human transgenic organism.

One aspect of the invention encompasses gene therapy for regulating the expression of a Tet operator-linked gene. In one embodiment the gene therapy comprises administering a pharmaceutical composition comprising a first nucleic acid molecule encoding a protein selected from the group consisting of at least one rtTA protein with decreased basal transcriptional activity in the absence of doxycycline or a sequence variant thereof, a second nucleic acid molecule comprising a gene of interest, the expression of which is regulated by sequences derived from the tet operator; and a therapeutically effective dose of tetracycline, or an analog thereof. In another embodiment the gene therapy comprises administering a pharmaceutical composition comprising a first nucleic acid molecule encoding a protein selected from the group consisting of at least one rtTA protein with increased induced transcriptional activity in the absence of doxycycline or a sequence variant thereof, a second nucleic acid molecule comprising a gene of interest, the expression of which is regulated by sequences derived from the tet operator; and a therapeutically effective dose of tetracycline or an analog thereof. In a further embodiment the gene therapy comprises administering a pharmaceutical composition comprising a first nucleic acid molecule encoding a protein selected from the group consisting of at least one tTA protein with differential induction by tetracycline or analogs thereof, or a sequence variant thereof, a second nucleic acid molecule comprising a gene of interest, the expression of which is regulated by sequences derived from the tet operator; and a therapeutically effective dose of tetracycline or an analog thereof.

The invention also provides compositions for gene therapy for regulating the expression of a Tet operator-linked gene. In one embodiment the gene therapy composition comprises a gene therapy vector encoding a protein selected from the group consisting of at least one rtTA protein with decreased basal transcriptional activity in the absence of doxycycline or a sequence variant thereof; a second gene therapy vector comprising a gene of interest, the expression of which is regulated by sequences derived from the tet operator; and a therapeutically effective dose of tetracycline, or an analog thereof. In another embodiment the gene therapy composition comprises a gene therapy vector encoding a protein selected from the group consisting of at least one rtTA protein with increased induced transcriptional activity in the absence of doxycycline or a sequence variant thereof; a second gene therapy vector comprising a gene of interest, the expression of which is regulated by sequences derived from the tet operator; and a therapeutically effective dose of tetracycline or an analog thereof. In a further embodiment the gene therapy composition comprises a gene therapy vector encoding a protein selected from the group consisting of at least one tTA protein with differential induction by tetracycline or analogs thereof, or a sequence variant thereof; a second gene therapy vector comprising a gene of interest, the expression of which is regulated by sequences derived from the tet operator; and a therapeutically effective dose of tetracycline or an analog thereof.

BRIEF DESCRIPTION OF THE DRAWINGS

FIG. 8 depicts the nucleic acid sequence encoding the parent rtTA protein (SEQ ID NO: 22).

FIG. 9 depicts the nucleic acid sequence encoding the parent tTA protein (SEQ ID NO: 24).

DETAILED DESCRIPTION OF THE INVENTION

Figure 1:
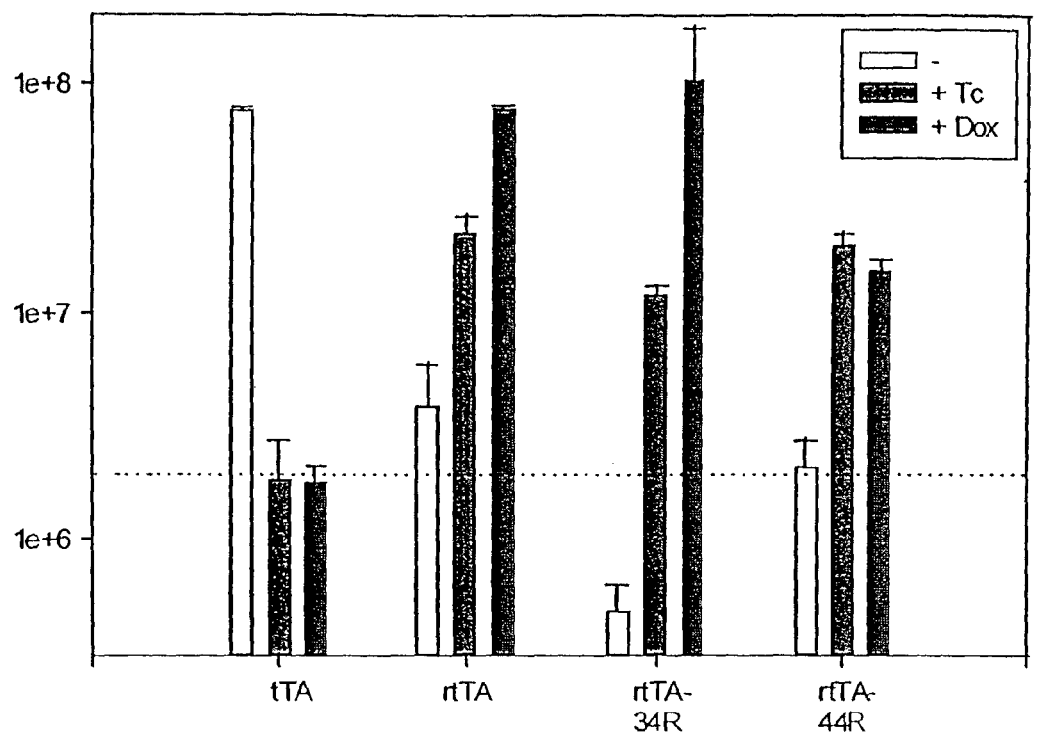
FIG. 1 is a graph depicting the rtTA dependent GFP fluorescence in *S. cerevisiae* in dependence of Tc and doxycycline (Dox).

The present invention provides a panel of transcriptional activator fusion proteins which comprises both tetracycline controlled transactivator proteins and reverse tetracycline transactivator proteins. These transactivators have novel phenotypes such as decreased basal transcriptional activity in the absence of doxycycline, increased induced transcriptional activity in the presence of doxycycline, or differential induction by tetracycline and analogs of tetracycline.

In one aspect of the present invention, specific mutations or alterations are introduced into a transcriptional regulatory protein. In another aspect, random mutagenesis techniques, coupled with selection or screening systems, are used to introduce large numbers of mutations into a transcriptional regulatory protein. The resulting collection of randomly mutated proteins is then subjected to a selection for the desired phenotype or a screen in which the desired phenotype can be observed against a background of undesirable phenotypes.

In accordance with the random mutagenesis, in one aspect of the invention one can mutagenize an entire molecule or one can proceed by cassette mutagenesis. In the former instance, the entire coding region of a molecule is mutagenized by one of several methods (chemical, PCR, doped oligonucleotide synthesis), and the resulting collection of randomly mutated molecules is subjected to selection or screening procedures. Random mutagenesis can be applied in this way in cases where the molecule being studied is relatively small and there are powerful and stringent selections or screens available to discriminate between the different classes of mutant phenotypes that will inevitably arise.

Random mutagenesis may be accomplished by many means, including:

1. PCR mutagenesis, in which the error prone Taq polymerase is exploited to generate mutant alleles of transcriptional regulatory proteins, which are assayed directly in yeast for an ability to couple.

2. Chemical mutagenesis, in which expression cassettes encoding transcriptional regulatory proteins are exposed to mutagens and the protein products of the mutant sequences are assayed directly in yeast for an ability to couple.

3. Doped synthesis of oligonucleotides encoding portions of the transcriptional regulatory protein gene.

4. In vivo mutagenesis, in which random mutations are introduced into the coding region of transcriptional regulatory proteins by passage through a mutator strain of *E. coli*, XL1-Red (mutD5 mutS mutT) (Stratagene, Menasa, Wis.). Substitution of mutant peptide sequences for functional domains in a transcriptional regulatory protein permits the determination of specific sequence requirements for the accomplishment of function.

In accordance with the specific mutagenesis aspect of the invention, discrete regions of a protein, corresponding either to defined structural (i.e. α-helices, β-sheets, turns, surface loops) or functional determinants (e.g., DNA binding determinants, transcription regulatory domains) are subjected to saturating or semi-random mutagenesis. The resulting mutagenized cassettes are re-introduced into the context of the otherwise wild type allele. Cassette mutagenesis is useful when there is experimental evidence available to suggest a particular function for a region of a molecule, and there is a selection and/or screening approach available to discriminate between interesting and uninteresting mutants. Cassette mutagenesis is also useful when the parent molecule is comparatively large and the desire is to map the functional domains of a molecule by mutagenizing the molecule in a step-wise fashion, i.e., mutating one linear cassette of residues at a time and then assaying for function.

Mutagenesis of tTA encoding sequences facilitates the identification of transactivators that interact differentially with different effector molecules. For example, mutagenesis can be restricted to portions of the sequence responsible for forming the effector binding pocket. Such properties can be exploited to control different genes via specific sets of transactivators and effectors (see Baron et al., 1999). Modification of the effector binding pocket is most likely a prerequisite for the detection of tetracyclines that are not deposited in bone tissue. For gene therapy, it will be advantageous to use transactivators that are insensitive toward tetracyclines used in human medicine.

Full effector function at Dox concentrations of 10 to 30 ng/ml, as with tTA, is highly desirable, particularly in experiments involving transgenic animals or in gene therapy. Accordingly, the present invention provides for screening for rtTA variants with increased sensitivity towards Dox.

In addition, new effector molecules for tTA and rtTA may be identified. For example, effector substances that fully induce rtTA at lower concentrations can be identified. The screening methods in accordance with the invention facilitate the examination of substance libraries, advantageously in a high throughput format, for new effectors with superior effector properties and negligible antibiotic activity. Candidates for screening include:
- tetracyclines that have lost antibiotic activity;
- tetracyclines that mediate rtTA activation at low concentrations;
- tetracyclines that may not deposit in bone tissue;
- tetracyclines with improved tissue penetration properties;
- tetracycline antagonists; and
- non-tetracycline compounds that can serve as effectors for tTA and/or rtTA.

Similarly, mutagenesis of tTA and rtTA encoding sequences within the DNA binding domain will facilitate the identification of transactivator proteins with decreased residual affinity for tet operator sequences in the presence and absence of tetracycline or analogs thereof, respectively, and altered DNA binding specificity. Structure-function analysis of tet repressor-based transcriptional regulatory proteins is also likely to identify improved transactivators with increased temperature tolerance.

Definitions

Before further description of the invention, certain terms employed in the specification, examples and appended claims are, for convenience, collected here.

The term "allelic variants of transactivator fusion proteins" is intended to include both functional and non-functional transactivator fusion proteins. Functional allelic variants are amino acid sequence variants of the transactivator fusion proteins that maintain the ability to regulate transcription. Non-functional allelic variants are amino acid sequence variants of the transactivator fusion proteins that do not have the ability to regulate transcription.

The term "antibody" as used herein is intended to include immunoglobulin molecules and immunologically active portions of immunoglobulin molecules, i.e., molecules that contain an antigen binding site which specifically binds (immunoreacts with) an antigen, such as a transactivator fusion protein. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind the transactivator fusion proteins. The term "monoclonal antibody" or "monoclonal antibody composition", as used herein, refers to a population of antibody molecules that contain only one species of an antigen binding site capable of immunoreacting with a particular epitope of a transactivator fusion protein. A monoclonal antibody composition thus typically displays a single binding affinity for a particular transactivator fusion protein with which it immunoreacts.

As used herein, a "biologically active portion" of a transactivator fusion protein is intended to include a fragment of a transactivator fusion protein which carries out the transcriptional regulatory function of a transactivator fusion protein.

As used herein, a chimeric transactivator fusion protein comprises a transactivator fusion protein polypeptide which is further operatively linked to a heterologous polypeptide. A "transactivator fusion protein polypeptide" refers to a polypeptide having an amino acid sequence corresponding to transactivator fusion protein, whereas a "heterologous polypeptide" refers to a polypeptide having an amino acid sequence corresponding to a protein which is not substantially homologous to the transactivator fusion protein, e.g., a protein which is different from the transactivator fusion protein and which is derived from the same or a different organism. Within a chimeric transactivator fusion protein the transactivator fusion protein polypeptide can correspond to all or a portion of a transactivator fusion protein.

The term "derived from" is intended to mean that a sequence is identical to or modified from another sequence. Polypeptide or protein derivatives include polypeptide or protein sequences that differ from the sequences described or known in amino acid sequence, or in ways that do not involve sequence, or both, and still preserve the activity of the polypeptide or protein. Derivatives in amino acid sequence are produced when one or more amino acids is substituted with a different natural amino acid, an amino acid derivative or non-native amino acid. In certain embodiments protein derivatives include naturally occurring polypeptides or proteins, or biologically active fragments thereof, whose sequences differ from the wild type sequence by one or more conservative amino acid substitutions, which typically have minimal influence on the secondary structure and hydrophobic nature of the protein or peptide. Derivatives may also have sequences which differ by one or more non-conservative amino acid substitutions, deletions or insertions which do not abolish the biological activity of the polypeptide or protein.

Conservative substitutions (substituents) typically include the substitution of one amino acid for another with similar characteristics (e.g., charge, size, shape, and other biological properties) such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

The polypeptides and proteins of this invention may also be modified by various changes such as insertions, deletions and substitutions, either conservative or nonconservative where such changes might provide for certain advantages in their use.

In other embodiments, derivatives with amino acid substitutions which are less conservative may also result in desired derivatives, e.g., by causing changes in charge, conformation and other biological properties. Such substitutions would include, for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

Derivatives within the scope of the invention also include polynucleotide derivatives. Polynucleotide or nucleic acid derivatives differ from the sequences described or known in nucleotide sequence. For example, a polynucleotide derivative may be characterized by one or more nucleotide substitutions, insertions, or deletions.

The term "DNA binding protein" is intended to include any protein, or functional domain thereof, that specifically interacts with a cognate DNA sequence, or response element, within the regulatory sequences of a gene. The DNA binding domains of transcriptional regulatory proteins can be classified into structural families which include, but are not limited to, basic helix-loop-helix domains, leucine zipper domains, zinc finger domains, and helix-turn-helix domains/homeodomains. A fusion protein of the present invention includes a polypeptide comprising a DNA binding protein, or a functional DNA binding domain thereof. The recognition and binding of a DNA binding protein to its cognate DNA sequence can be regulated by conformational changes in the DNA binding protein itself conferred by the binding of a modulator molecule or ligand. Similarly, the conformation of the cognate DNA sequence within the chromatin, e.g., organized into nucleosome, also influences the binding of a DNA binding protein to its cognate DNA sequence.

As used herein, the terms "gene" and "recombinant gene" are intended to include nucleic acid molecules which include an open reading frame encoding a transactivator fusion protein.

The term "gene regulatory sequences" or "regulatory sequences" is intended to include the DNA sequences that control the transcription of an adjacent gene. Gene regulatory sequences include, but are not limited to, promoter sequences that are found in the 5' region of a gene proximal to the transcription start site which bind RNA polymerase to initiate transcription. Gene regulatory sequences also include enhancer sequences which can function in either orientation and in any location with respect to a promoter, to modulate the utilization of a promoter. Transcriptional control elements include, but are not limited to, promoters, enhancers, and repressor and activator binding sites. The gene regulatory sequences of the present invention contain binding sites for transcriptional regulatory proteins. In a preferred embodiment, gene regulatory sequences comprise sequences derived from the tet operator (tetO) which bind tet repressor proteins.

The term "homologous recombinant organism" as used herein is intended to include an organism, e.g. animal or plant, containing a gene which has been modified by homologous recombination between the gene and a DNA molecule introduced into a cell of the animal, e.g., an embryonic cell of the animal.

The terms "host cell" and "recombinant host cell" are used interchangeably herein. A "host cell" includes any cultivatable cell that can be modified by the introduction of heterologous DNA. Preferably, a host cell is one in which a transcriptional regulatory protein can be stably expressed, post-translationally modified, localized to the appropriate subcellular compartment, and made to engage the appropriate transcription machinery. The choice of an appropriate host cell will also be influenced by the choice of detection signal. For example, reporter constructs, as described above, can provide a selectable or screenable trait upon activation or inhibition of gene transcription in response to a transcriptional regulatory protein; in order to achieve optimal selection or screening, the host cell phenotype will be considered. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell of the present invention includes prokaryotic cells and eukaryotic cells. Prokaryotes include gram negative or gram positive organisms, for example, *E. Coli* or *Bacilli*. Suitable prokaryotic host cells for transformation include, for example, *E. coli, Bacillus subtilis, Salmonella typhimurium*, and various other species within the genera *Pseudomonas, Streptomyces,* and *Staphylococcus*. Eukaryotic cells include, but are not limited to, yeast cells, plant cells, fungal cells, insect cells (e.g., baculovirus), mammalian cells, and the cells of parasitic organisms, e.g., trypanosomes.

As used herein, the term "yeast" includes not only yeast in a strict taxonomic sense, i.e., unicellular organisms, but also yeast-like multicellular fungi of filamentous fungi. Exemplary species include *Kluyverei lactis, Schizosaccharomyces pombe*, and *Ustilaqo maydis*, with *Saccharomyces cerevisiae* being preferred. Other yeast which can be used in practicing the present invention are *Neurospora crassa, Aspergillus niger, Aspergillus nidulans, Pichia pastoris, Candida tropicalis*, and *Hansenula polymorpha*.

Mammalian host cell culture systems include established cell lines such as COS cells, L cells, 3T3 cells, Chinese hamster ovary (CHO) cells, embryonic stem cells, with HeLa cells being preferred.

As used herein, an "isolated" or "purified" protein or biologically active portion thereof is intended to include proteins that are substantially free of cellular material or other contaminating proteins from the cell or tissue source from which the transactivator fusion protein is derived, or substantially free from chemical precursors or other chemicals when chemically synthesized.

The language "substantially free of cellular material" is intended to include preparations of transactivator fusion proteins in which the protein is separated from cellular components of the cells from which it is isolated or recombinantly produced. In one embodiment, when the transactivator fusion protein or biologically active portion thereof is recombinantly produced, the language "substantially free of cellular material" includes preparations of transactivator fusion proteins that are substantially free of culture medium, i.e., culture medium represents less than about 20%, more preferably less than about 10%, and most preferably less than about 5% of the volume of the protein preparation.

The language "substantially free of chemical precursors or other chemicals" is intended to include preparations of transactivator fusion proteins in which the protein is separated from chemical precursors or other chemicals which are involved in the synthesis of the protein. In one embodiment, the language "substantially free of chemical precursors or other chemicals" includes preparations of transactivator fusion proteins having less than about 30% (by dry weight) of chemical precursors or non-transactivator fusion protein chemicals, more preferably less than about 20% chemical precursors or non-transactivator fusion protein chemicals, still more preferably less than about 10% chemical precursors or non-transactivator fusion protein chemicals, and most preferably less than about 5% chemical precursors or non-transactivator fusion protein chemicals.

A "minimal activation domain" as used herein is intended to include a polypeptide sequence or fragment that comprises the transactivation potential of a transcriptional regulatory protein. A polypeptide encoding a minimal activation domain can be a naturally occurring polypeptide, e.g., it can be found within a protein that exists in nature, or it can be a polypeptide that has a composition that does not exist within a naturally occurring protein. In the context of the present invention a minimal activation domain is sufficient to confer upon a heterologous protein the ability to activate gene transcription. In a preferred embodiment, a minimal activation domain is derived from a 12 amino acid segment, residues 436 to 447, comprising the "acidic activation domain" of VP16.

A "non-essential" amino acid residue is intended to include a residue that can be altered from the wild-type sequence of a transactivator fusion protein (i.e., the sequence of SEQ ID NO:23 or 25) without altering the biological activity, whereas an "essential" amino acid residue is required for biological activity.

As used herein, the term "nucleic acid molecule" is intended to include DNA molecules (e.g., cDNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" is intended to include nucleic acid molecules which are separated from other nucleic acid molecules and which are substantially free of other cellular material, or culture medium when produced by recombinant techniques, or substantially free of chemical precursors or other chemicals when chemically synthesized.

The term "operatively linked" or "operably linked" is intended to mean that molecules are functionally coupled to each other in that the change of activity or state of one molecule is affected by the activity or state of the other molecule. Nucleotide sequences are "operably linked" when the regulatory sequence functionally relates to the DNA sequence encoding the polypeptide or protein of interest. For example, a promoter nucleotide sequence is operably linked to a DNA sequence encoding the protein or polypeptide of interest if the promoter nucleotide sequence controls the transcription of the DNA sequence encoding the protein of interest. Typically, two polypeptides that are operatively linked are covalently attached through peptide bonds.

The term "a polypeptide which activates transcription in eukaryotic cells" as used herein is intended to include polypeptides which either directly or indirectly activates transcription.

As used herein, a "reverse tetracycline controlled transactivator" or "rtTA" is intended to include a fusion protein comprising a TetR mutant which binds operator DNA only in presence of some tetracycline derivatives, or analogues, such as doxycycline (Dox) or anhydrotetracycline (ATc), operatively linked to a transcription activation domain. Thus, a rtTA protein will activate gene expression driven by $P_{tet}$ upon addition of Dox (Gossen et al., 1995).

The term "sequence variant" or "variant allele" is intended to include a polynucleotide encoding a polypeptide or protein that comprises at least one mutation relative to the wild type allele. A mutation in a polynucleotide sequence is transferred to a mutation in the amino acid sequence encoded by said polynucleotide, and may thus affect protein structure and function. Types of mutations include silent, missense and nonsense mutations, as well as insertion and deletion mutations.

A "tetracycline analog" is any one of a number of compounds that are closely related to tetracycline (Tc) and which bind to the tet repressor with a Ka of at least about $10^6$ $M^{-1}$. Preferably, the tetracycline analogue binds with an affinity of about $10^9$ $M^{-1}$ or greater, e.g., $10^9 M^{-1}$. Examples of such tetracycline analogues include, but are not limited to those disclosed by Hlavka and Boothe, "The Tetracyclines," in Handbook of Experimental Pharmacology 78, R. K. Blackwood et al. (eds.), SpringerVerlag, Berlin-New York, 1985; L. A. Mitscher "The Chemistry of the Tetracycline Antibiotics, Medicinal Research 9, Dekker, New York, 1978; Noyee Development Corporation, "Tetracycline Manufacturing Processes," Chemical Process Reviews, Park Ridge, N.J., 2 volumes, 1969; R. C. Evans, "The Technology of the Tetracyclines," Biochemical Reference Series 1, Quadrangle Press, New York, 1968; and H. F. Dowling, "Tetracycline," Antibiotics Monographs, no. 3, Medical Encyclopedia, New York, 1955; the contents of each of which are fully incorporated by reference herein. Examples of tetracycline analogues include anhydrotetracycline, doxycycline, chlorotetracycline, epioxytetracycline, cyanotetracycline and the like. Certain Tc analogues, such as anhydrotetracycline and epioxytetracycline, have reduced antibiotic activity compared to Tc.

As used herein, "Tetracycline controlled transactivators" or "tTAs" are fusions between TetR and proper domains of transcriptional activators.

The terms "transactivator fusion protein" and "transcriptional activator protein" are intended to include any protein that is capable of stimulating the transcription of a gene by contact, either directly or indirectly, with the gene regulatory sequences of the gene. Typically, the DNA binding and transcriptional activation functions of a transcriptional regulatory protein, or transcription factor, are contained within discrete, modular domains of the protein. A transactivator fusion protein of the present invention includes a fusion protein comprising a polypeptide comprising a DNA binding protein operatively linked, e.g., functionally coupled, to a polypeptide comprising amino acid sequences derived from a transcriptional activation domain.

The term "transcriptional regulatory domain" is intended to include the discrete domain of a transcriptional regulatory protein that modulates transcription of a gene. The mechanism by which a transcriptional regulatory domain modulates transcription includes, but is not limited to, direct or indirect interaction with elements of the basal transcription complex, e.g., RNA polymerase and TATA binding protein, direct or indirect interaction with other transcriptional regulatory proteins, and alteration of the conformation of the gene regulatory sequences. A transcriptional regulatory domain can either activate or inhibit transcription.

The Herpes simplex virion protein 16 contains two distinct transcriptional activation domains characterized by bulky, hydrophobic amino acids positioned in a highly negatively charged surrounding (Regier, J. L., Shen, F., and Triezenberg, S. J. (1993) *Proc. Natl. Acad. Sci. U.S.A.* 90, 883-887). Each domain was shown to activate transcription when fused to a heterologous DNA binding domain, such as the one of GAL4 (Seipel, K., Georgiev, O., and Schaffner, W. (1992) *EMBO-J* 11, 4961-4968). The C-terminal transcriptional activation domain of Herpes simplex virion protein 16 has been used frequently as the activator component of transactivator fusion proteins because of its strong capacity to stimulate transcription in eukaryotic cells.

In one embodiment, a transcriptional regulatory domain of the present invention is a polypeptide derived from the Herpes simplex virion protein 16. In another embodiment, a transcriptional regulatory domain includes at least one copy of a minimal activation domain of Herpes simplex virion protein 16. In a preferred embodiment, a transcriptional regulatory domain comprises an acidic region comprising amino acid residues 436 to 447 of the Herpes simplex virion protein 16.

The terms "transcriptional regulatory protein" and "transcriptional regulator" are used interchangeably and are intended to include any protein that is capable of modulating the transcription of a gene by contact, either directly or indirectly, with the gene regulatory sequences of the gene. Typically, the DNA binding and transcriptional activation or repression functions of a transcriptional regulatory protein, or transcription factor, are contained within discrete, modular domains of the protein. A transcriptional regulatory protein of the present invention includes a fusion protein comprising a polypeptide comprising a DNA binding protein operatively linked, e.g., functionally coupled, to a polypeptide comprising amino acid sequences derived from a transcriptional regulatory domain.

As used herein, the term "vector" is intended to include a nucleic acid molecule capable of transporting another nucleic acid to which it has been linked. A vector may be characterized by one or a small number of restriction endonuclease sites at which such DNA sequences may be cut in a determinable fashion without the loss of an essential biological function of the vector, and into which a DNA fragment may be spliced in order to bring about its replication and cloning. A vector may further contain a marker suitable for use in the identification of cells transformed with the vector. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The present invention pertains to nucleic acid molecules and proteins which can be used to regulate the expression of genes in vitro or in vivo in a highly controlled manner. Various aspects of the invention pertain to fusion proteins which are capable of activating gene transcription when bound to tet operator (tetO) sequences, but which bind to tet operator sequences only in the presence or, alternatively, in the absence of tetracycline, or an analog thereof. Thus, in a host cell, transcription of a gene operatively linked to a tet operator sequence(s) is stimulated by a fusion protein of the invention by altering the concentration of tetracycline (or analog) in contact with the host cell (e.g., adding or removing tetracycline from a culture medium, or administering or ceasing to administer tetracycline to a host organism, etc.)

The transcriptional regulatory proteins of the invention are transactivators which stimulate the transcription of a gene under the control of sequences derived from the tet operator. The transactivators of the invention are fusion proteins. One aspect of the invention thus pertains to fusion proteins and nucleic acids (e.g., DNA) encoding fusion proteins. The term "fusion protein" is intended to describe at least two polypeptides, typically from different sources, which are operatively linked. Typically, the two polypeptides are covalently attached through peptide bonds. The fusion protein is preferably produced by standard recombinant DNA techniques. For example, a DNA molecule encoding the first polypeptide is ligated to another DNA molecule encoding the second polypeptide, and the resultant hybrid DNA molecule is expressed in a host cell to produce the fusion protein. The DNA molecules are ligated to each other in a 5' to 3' orientation such that, after ligation, the translational frame of the encoded polypeptides is not altered (i.e., the DNA molecules are ligated to each other in-frame).

The First Polypeptide of the Transactivator Fusion Protein

The transactivator fusion proteins of the invention are composed, in part, of a first polypeptide which binds to a tet operator sequence in the presence or absence of tetracycline (Tc), or an analog thereof. The first polypeptide of the fusion protein is a Tet repressor. In a preferred embodiment, the first polypeptide of the fusion protein is a sequence variant of a Tet repressor. This mutated Tet repressor is intended to include polypeptides having an amino acid sequence which is similar to a wild-type Tet repressor but which has at least one amino acid difference from the wild-type Tet repressor. The term "wild-type Tet repressor" is intended to describe a protein occurring in nature which represses transcription from tet operator sequences in prokaryotic cells in the absence of Tc. The term "tet repressor" is intended to include repressors of different class types, e.g., class A, B, C, D, E, or G tet repressors. The amino acid difference(s) between a mutated Tet repressor and a wild-type Tet repressor may be substitution of one or more amino acids, deletion of one or more amino acids or addition of one or more amino acids.

A first polypeptide of the transactivator fusion protein (e.g., the Tet repressor) has the property of binding specifically to a tet operator sequence. Each class of Tet repressor has a corresponding target tet operator sequence. Accordingly, the term "tet operator sequence" is intended to encompass all classes of tet operator sequences, e.g. class A, B, C, D, E, or G. In a preferred embodiment, the mutated Tet repressor is a Tn10-encoded repressor (i.e., class B) and the tet operator sequence is a class B tet operator sequence. Alternatively, a mutated class A Tet repressor can be used with a class A tet operator sequence, and so on for the other classes of Tet repressor/operators.

The Second Polypeptide of the Transactivator Fusion Protein

The first polypeptide of the transactivator fusion protein is operatively linked to a second polypeptide which directly or indirectly activates transcription in eukaryotic cells. To operatively link the first and second polypeptides, typically nucleotide sequences encoding the first and second polypeptides are ligated to each other in-frame to create a chimeric gene encoding a fusion protein, although the first and second polypeptides can be operatively linked by other means that preserve the function of each polypeptide (e.g., chemically crosslinked). In a preferred embodiment, the second polypeptide of the transactivator itself possesses transcriptional activation activity (i.e., the second polypeptide directly activates transcription). In another embodiment, the second polypeptide activates transcription by indirect mechanisms, through recruitment of a transcriptional activation protein to interact with the fusion protein.

Polypeptides which can function to activate transcription in eukaryotic cells are well known in the art. In particular, transcriptional activation domains of many DNA binding proteins have been described and have been shown to retain their activation function when the domain is transferred to a heterologous protein. A preferred polypeptide for use in the fusion protein of the invention is the herpes simplex virus virion protein 16 (referred to herein as VP16, the amino acid sequence of which is disclosed in Triezenberg, S. J. et al. (1988) *Genes Dev.* 2:718-729). In one embodiment, the second polypeptide of the fusion protein is a polypeptide derived from the Herpes simplex virus protein 16 (VP16). In another embodiment the second polypeptide of the fusion protein comprises at least one copy of an minimal activation domain of Herpes simplex VP16. In a further embodiment, the second polypeptide of the fusion protein comprises at least one copy of an acidic region comprising amino acid residues 436 to 447 of Herpes simplex VP16.

Other polypeptides with transcriptional activation ability in eukaryotic cells can be used in the fusion protein of the invention. Transcriptional activation domains found within various proteins have been grouped into categories based upon similar structural features. Types of transcriptional activation domains include acidic transcription activation domains, proline-rich transcription activation domains, serine/threonine-rich transcription activation domains and glutamine-rich transcription activation domains. Examples of acidic transcriptional activation domains include the VP16 regions already described and amino acid residues 753-881 of GAL4. Examples of proline-rich activation domains include amino acid residues 399-499 of CTF/NF1 and amino acid residues 31-76 of AP2. Examples of serine/threonine-rich transcription activation domains include amino acid residues 1-427 of ITF1 and amino acid residues 2-451 of ITF2. Examples of glutamine-rich activation domains include amino acid residues 175-269 of Oct1 and amino acid residues 132-243 of Sp1. The amino acid sequences of each of the above described regions, and of other useful transcriptional activation domains, are disclosed in Seipel, K. et al. (*EMBO J.* (1992) 13:4961-4968).

In addition to previously described transcriptional activation domains, novel transcriptional activation domains, which can be identified by standard techniques, are within the scope of the invention. The transcriptional activation ability of a polypeptide can be assayed by linking the polypeptide to another polypeptide having DNA binding activity and determining the amount of transcription of a target sequence that is stimulated by the fusion protein. For example, a standard assay used in the art utilizes a fusion protein of a putative transcriptional activation domain and a GAL4 DNA binding domain (e.g., amino acid residues 1-93). This fusion protein is then used to stimulate expression of a reporter gene linked to GAL4 binding sites (see e.g., Seipel, K. et al. (1992) *EMBO J.* 11:4961-4968 and references cited therein).

In another embodiment, the second polypeptide of the fusion protein indirectly activates transcription by recruiting a transcriptional activator to interact with the fusion protein. For example, a tetR of the invention can be fused to a polypeptide domain (e.g., a dimerization domain) capable of mediating a protein-protein interaction with a transcriptional activator protein, such as an endogenous activator present in a host cell. It has been demonstrated that functional associations between DNA binding domains and transactivation domains need not be covalent (see e.g., Fields and Song (1989) *Nature* 340:245-247; Chien et al. (1991) *Proc. Natl. Acad. Sci. USA* 88:9578-9582; Gyuris et al. (1993) *Cell* 75:791-803; and Zervos, A. S. (1993) *Cell* 72:223-232). Accordingly, the second polypeptide of the fusion protein may not directly activate transcription but rather may form a stable interaction with an endogenous polypeptide bearing a compatible protein-protein interaction domain and transactivation domain. Examples of suitable interaction (or dimerization) domains include leucine zippers (Landschulz et al. (1989) *Science* 243:1681-1688), helix-loop-helix domains (Murre, C. et al. (1989) *Cell* 58:537-544) and zinc finger domains (Frankel, A. D. et al. (1988) *Science* 240:70-73). Interaction of a dimerization domain present in the fusion protein with an endogenous nuclear factor results in recruitment of the transactivation domain of the nuclear factor to the fusion protein, and thereby to a tet operator sequence to which the fusion protein is bound.

In a preferred embodiment, a transactivator fusion protein of the present invention is a tetracycline controlled transactivator protein. The chimeric "tetracycline controlled transactivators" (tTA) allow one to regulate the expression of genes placed downstream of minimal promoter tetO fusions ($P_{tet}$). In absence of Tc, $P_{tet}$ is activated whereas in presence of the antibiotic activation of $P_{tet}$ is prevented. In one embodiment, a polynucleotide encoding a polypeptide derived from the Herpes simplex virus protein 16 (VP16) is fused at the level of DNA to TetR. In another embodiment, a polynucleotide encoding at least one copy of a minimal activation domain of Herpes simplex VP16 is operably linked to TetR. In a further embodiment, a polynucleotide encoding at least one copy of an acidic region comprising amino acid residues 436 to 447 of Herpes simplex VP16 is operably linked to TetR.

In a further preferred embodiment, a transactivator fusion protein of the present invention is a reverse tetracycline controlled transactivator protein. In one embodiment, a transcription activation domain of a rtTA protein is a polypeptide derived from the Herpes simplex virus protein 16 (VP16). In another embodiment, a transcription activation domain of a rtTA protein comprises at least one copy of an minimal activation domain of Herpes simplex VP16 is operably linked to TetR. In further embodiment, a transcription activation domain of a rtTA protein comprises at least one copy of an acidic region comprising amino acid residues 436 to 447 of Herpes simplex VP16 is operably linked to TetR.

In one aspect of the invention a transactivator fusion protein of the invention is a sequence variant of an rtTA protein (i.e., as compared to the reference rtTA sequence in SEQ ID NO:22 or 23). A sequence variant of an rtTA protein will contain at least one mutation that confers a novel phenotype upon the protein.

In one embodiment, the mutated rtTA protein has altered basal transcriptional activity in the absence of doxycycline, or an analog thereof. In a preferred embodiment, a rtTA protein has at least one amino acid within the DNA binding domain. In one embodiment the DNA binding domain comprises amino acid positions 1-45 of SEQ ID NO:23. In a preferred embodiment, the mutation is selected from the group comprising: S12G, E19G, and T26A. In another embodiment, a mutation within the DNA binding domain confers increased or decreased basal affinity for the tet operator in the absence of doxycycline, or an analog thereof.

In another embodiment, the mutated rtTA protein has increased or decreased induced transcriptional activity in the presence of doxycycline, or an analog thereof. In a preferred embodiment, a rtTA protein of the invention has at least one amino acid mutation within the tetracycline binding domain. In one embodiment the tetracycline binding domain comprises amino acid positions 46-207 of SEQ ID NO:23. In a preferred embodiment, the mutation is selected from the group comprising: A56P, R87S, deletion C88, D95G, G96R, V99E, D148E, H179R, and E204K. In another embodiment, a mutation within the tetracycline binding domain confers increased or decreased sensitivity towards doxycycline, or an analog thereof.

Table 1 specifies the mutations that occur within the novel rtTA fusion proteins of the invention. An rtTA protein is preferably mutated at at least one of these positions. Other amino acid substitutions, deletions or additions at these or other amino acid positions which retain the desired functional properties of the mutated rtTA protein are within the scope of the invention.

In another aspect of the invention a transactivator fusion protein of the invention is a sequence variant of a tTA protein (i.e., as compared to the reference tTA sequence in SEQ ID NO:24 or 25). A sequence variant of a tTA protein will contain at least one mutation that confers a novel phenotype upon the protein.

In one embodiment, the mutated tTA protein displays differential induction by tetracycline, and analogs thereof. In a preferred embodiment, a tTA protein of the invention has at least one amino acid mutation within the tetracycline binding domain. In one embodiment the tetracycline binding domain comprises amino acid positions 46-207 of SEQ ID NO:25. In a preferred embodiment the mutation is selected from the group comprising: A56V, F78S, S85G, S85R, Y110C, L113H, Y132C, I164L, P167S, L170V, I174V, I174T, or E183K. In another embodiment, a mutation within the tetracycline binding domain confers either increased or decreased sensitivity towards tetracycline, or an analog thereof.

In another embodiment, a tTA protein of the invention has at least one amino acid mutation within the DNA binding domain. In one embodiment the DNA binding domain comprises amino acid positions 1-45 of SEQ ID NO:25 Table 2 specifies the mutations that occur within the novel tTA fusion proteins of the invention. A tTA protein is preferably mutated at least one of these positions. Other amino acid substitutions, deletions or additions at these or other amino acid positions which retain the desired functional properties of the mutated tTA protein are within the scope of the invention.

Additional mutated transactivator fusion proteins can be created according to the teachings of the invention. A number of different classes of Tet repressors have been described, e.g., A, B, C, D, E, and G. The amino acid sequences of the different classes of Tet repressors share a high degree of homology (i.e., 40-60% across the length of the proteins), including in the region encompassing the above-described mutations. The amino acid sequences of various classes of Tet repressors are described in Tovar, K. et al. (1988) *Mol. Gen. Genet.* 215:76-80. Accordingly, equivalent mutations to those described in Tables 1 and 2 can be made in other classes of Tet repressors for inclusion in a fusion protein of the invention. Additional suitable equivalent mutations will be apparent to those skilled in the art and can be created and tested for functionality. Nucleotide and amino acid sequences of Tet repressors of the A, C, D and E classes are disclosed in Waters, S. H. et al. (1983) *Nucl. Acids Res* 11:6089-6105, Unger, B. et al. (1984) *Gene* 31: 103-108, Unger, B. et al. (1984) *Nucl Acids Res.* 12:7693-7703 and Tovar, K. et al. (1988) *Mol. Gen. Genet.* 215:76-80, respectively. These wild-type sequences can be mutated according to the teachings of the invention for use in inducible regulation of gene transcription.

Additional suitable mutated rtTA and tTA proteins in accordance with the invention (i.e., having the desired functional properties described above) can be created by mutagenesis of a wild type rtTA or tTA protein, respectively. The nucleotide and amino acid sequences of wild-type rtTA and tTA proteins are indicated herein (FIGS. 8 and 9). A mutated rtTA or tTA can be created and selected, for example as follows: a nucleic acid (e.g., DNA) encoding a wild-type rtTA is subjected to random mutagenesis and the resultant mutated nucleic acids are incorporated into an expression vector and introduced into a host cell for screening (e.g., See Example 1). A screening assay is used which allows for selection of a rtTA protein which binds to a tet operator sequence only in the presence of doxycycline. For example, a library of mutated nucleic acids in an expression vector can be introduced into an yeast strain in which tet operator sequences control the expression of a gene encoding green fluorescent protein (GFP). Binding of a rtTA protein to tet operator sequences in yeast will stimulate expression of the GFP gene. Cells expressing the GFP are selected based upon fluorescence. For wild-type rtTAs, expression of the GFP gene will occur in the presence of doxycycline. A nucleic acid encoding a mutated rtTA protein is selected using this system based upon the ability of the nucleic acid to decrease expression of the GFP gene in yeast in the absence of doxycycline. A mutated rtTA protein having specific mutations (e.g., at positions 19, 56, 148 and 179) can be created by introducing nucleotide changes into a nucleic acid encoding a wild-type repressor by standard molecular biology techniques, e.g., site directed mutagenesis or PCR-mediated mutagenesis using oligonucleotide primers incorporating the nucleotide mutations. Alternatively, when a mutated Tet repressor is identified by selection from a library, the mutated nucleic acid can be recovered from the library vector.

It is understood to one skilled in the art, that the nucleotide sequence determined from the sequencing of the mutant transactivator fusion protein genes allows for the generation of comparable transactivator fusion protein mutations within homologous genes.

Isolated Nucleic Acid Molecules

One aspect of the invention pertains to isolated nucleic acid molecules that encode transactivator fusion proteins or biologically active portions thereof, as well as nucleic acid fragments sufficient for use as hybridization probes to identify transactivator fusion protein-encoding nucleic acid molecules (e.g., transactivator fusion protein mRNA) and fragments for use as PCR primers for the amplification or mutation of transactivator fusion protein nucleic acid molecules.

A nucleic acid molecule of the present invention, e.g., a nucleic acid molecule having the nucleotide sequence of SEQ ID NO: 1, 3, 5, 6, 8, 10, 12, 14, 16, 18, 20, 22, 24, 26, 28, 30, 32, 34, 36, 38, 40, 42, or 44, or a portion thereof, can be generated using standard molecular biology techniques and the sequence information provided herein.

In a preferred embodiment, an isolated nucleic acid molecule of the invention comprises the nucleotide sequence shown in SEQ ID NO:1, 3, 5, 6, 8, 10, 12, 14, 16, 18, 20, 22, 24, 26, 28, 30, 32, 34, 36, 38, 40, 42, or 44.

In still another preferred embodiment, an isolated nucleic acid molecule of the present invention comprises a nucleotide sequence which is at least about 80%, 85%, 90%, 95%, 98% or more homologous to the entire length of the nucleotide sequence shown in SEQ ID NO: 1, 3, 5, 6, 8, 10, 12, 14, 16, 18, 20, 22, 24, 26, 28, 30, 32, 34, 36, 38, 40, 42, or 44.

Moreover, the nucleic acid molecule of the invention can comprise only a portion of the nucleic acid sequence of SEQ ID NO: 1, 3, 5, 6, 8, 10, 12, 14, 16, 18, 20, 22, 24, 26, 28, 30, 32, 34, 36, 38, 40, 42, or 44, for example, a fragment which can be used as a primer or a fragment encoding a portion of a transactivator fusion protein, e.g., a biologically active portion of a transactivator fusion protein. In a preferred embodiment, a nucleic acid molecule comprises at least 100 contiguous nucleotides of a nucleic acid comprising SEQ ID NO: 1, 3, 5, 6, 8, 10, 12, 14, 16, 18, 20, 22, 24, 26, 28, 30, 32, 34, 36, 38, 40, 42, or 44.

Probes based on the transactivator fusion protein nucleotide sequences can be used to detect transcripts encoding the same or homologous proteins. Such probes can be used as a part of a diagnostic test kit for identifying cells or tissue which express a transactivator fusion protein of the invention, such as by measuring a level of a transactivator fusion protein-encoding nucleic acid in a sample of cells from a subject e.g., detecting transactivator fusion protein mRNA levels.

A nucleic acid fragment encoding a "biologically active portion" of a transactivator fusion protein can be prepared by isolating a portion of the nucleotide sequence of SEQ ID NO: 1, 3, 5, 6, 8, 10, 12, 14, 16, 18, 20, 22, 24, 26, 28, 30, 32, 34, 36, 38, 40, 42, or 44, which encodes a polypeptide having a transactivator fusion protein biological activity (e.g., the activity of the transactivator fusion protein to regulate transcription), expressing the encoded portion of the transactivator fusion protein (e.g., by recombinant expression in vitro) and assessing the activity of the encoded portion of the transactivator fusion protein. In a preferred embodiment, a polynucleotide of the invention encodes a fragment comprising at least 30 contiguous amino acid residues of the amino acid sequence of SEQ ID NO:2, 4, 7, 9, 11, 13, 15, 17, 19, 21, 23, 25, 27, 29, 31, 33, 35, 37, 39, 41, 43 or 45.

The invention further encompasses nucleic acid molecules that differ from the nucleotide sequence shown in SEQ ID NO: 1, 3, 5, 6, 8, 10, 12, 14, 16, 18, 20, 22, 24, 26, 28, 30, 32, 34, 36, 38, 40, 42, or 44, due to degeneracy of the genetic code and thus encode the same transactivator fusion protein as those encoded by the nucleotide sequence shown in SEQ ID NO: 1, 3, 5, 6, 8, 10, 12, 14, 16, 18, 20, 22, 24, 26, 28, 30, 32, 34, 36, 38, 40, 42, or 44. In one embodiment, an isolated nucleic acid molecule of the invention has a nucleotide sequence encoding a protein having an amino acid sequence shown in SEQ ID NO:2, 4, 7, 9, 11, 13, 15, 17, 19, 21, 23, 25, 27, 29, 31, 33, 35, 37, 39, 41, 43 or 45, or a fragment thereof. In another embodiment, an isolated nucleic acid molecule of the invention has a nucleotide sequence encoding a protein having at least about 80%, 85%, 90%, 95%, 98% or more identity to SEQ ID NO: 2, 4, 7, 9, 11, 13, 15, 17, 19, 21, 23, 25, 27, 29, 31, 33, 35, 37, 39, 41, 43 or 45, or a fragment thereof.

In addition to the transactivator fusion protein nucleotide sequences shown in SEQ ID NO: 1, 3, 5, 6, 8, 10, 12, 14, 16, 18, 20, 22, 24, 26, 28, 30, 32, 34, 36, 38, 40, 42, or 44, it will be appreciated by those skilled in the art that DNA sequence polymorphisms that lead to changes in the amino acid sequences of the polypeptide components of the transactivator fusion proteins may exist within a population. Such genetic polymorphism in the polypeptides of the transactivator fusion protein genes may exist within a population due to natural allelic variation.

Functional allelic variants will typically contain conservative substitution of one or more amino acids of SEQ ID NO: 2, 4, 7, 9, 11, 13, 15, 17, 19, 21, 23, 25, 27, 29, 31, 33, 35, 37, 39, 41, 43 or 45, or substitution, deletion or insertion of non-critical residues in non-critical regions of the protein.

Non-functional allelic variants will typically contain a non-conservative substitution, a deletion, or insertion, or premature truncation of the amino acid sequence of SEQ ID NO: 2, 4, 7, 9, 11, 13, 15, 17, 19, 21, 23, 25, 27, 29, 31, 33, 35, 37, 39, 41, 43 or 45, or a substitution, insertion, or deletion in critical residues or critical regions of the protein.

An isolated nucleic acid molecule encoding a transactivator fusion protein homologous to the protein of SEQ ID NO: 2, 4, 7, 9, 11, 13, 15, 17, 19, 21, 23, 25, 27, 29, 31, 33, 35, 37, 39, 41, 43 or 45, can be created by introducing one or more nucleotide substitutions, additions or deletions into the nucleotide sequence of SEQ ID NO: 1, 3, 5, 6, 8, 10, 12, 14, 16, 18, 20, 22, 24, 26, 28, 30, 32, 34, 36, 38, 40, 42, or 44, such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues.

Thus, a predicted nonessential amino acid residue in a transactivator fusion protein is preferably replaced with another amino acid residue from the same side chain family. Alternatively, in another embodiment, mutations can be introduced randomly along all or part of a transactivator fusion protein coding sequence, such as by saturation mutagenesis, and the resultant mutants can be screened for transactivation protein biological activity to identify mutants that retain transcriptional regulatory activity. Following mutagenesis of SEQ ID NO: 1, 3, 5, 6, 8, 10, 12, 14, 16, 18, 20, 22, 24, 26, 28, 30, 32, 34, 36, 38, 40, 42, or 44, the encoded protein can be expressed recombinantly and the transcriptional regulatory activity of the protein can be determined.

Homology or Identity

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90% or 95% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available online through Accelrys Inc. website (formerly Genetics Computer Group), San Diego, Calif.), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online through Accelrys Inc. website (formerly Genetics Computer Group), San Diego, Calif.), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4.

Nucleic acid and protein sequences can further be used as a "query sequence" to perform a search against public databases to, for example, identify other family members or related sequences. Such searches can be performed using the NBLAST and XBLASAT programs (version 2.0) of Altschul, et al. (1990) *J. Mol. Biol.* 215:403-10. BLAST nucleotide searches can be performed with the NBLAST program, score=100, wordlength=12 to obtain homologous nucleotide sequences. BLAST protein searches can be performed with the XBLAST program, score=50, wordlength=3 to obtain homologous amino acid sequences. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. (See e.g., the National Center for Biotechnology Information on-line database).

Additionally, the "Clustal" method (Higgins and Sharp, Gene, 73:237-44, 1988) and "Megalign" program (Clewley and Arnold, Methods Mol. Biol, 70:119-29, 1997) can be used to align sequences and determine similarity, identity, or homology.

Isolated Transactivator Fusion Proteins and Anti-Transactivator Fusion Protein Antibodies One aspect of the invention pertains to isolated transactivator fusion proteins, and biologically active portions thereof, as well as polypeptide fragments suitable for use as immunogens to raise anti-transactivator fusion protein antibodies. In one embodiment, transactivator fusion proteins are produced by recombinant DNA techniques. Alternative to recombinant expression, a transactivator fusion protein or polypeptide can be synthesized chemically using standard peptide synthesis techniques.

Biologically active portions of a transactivator fusion protein include peptides comprising amino acid sequences sufficiently homologous to or derived from the amino acid sequence of the transactivator fusion protein, (e.g., the amino acid sequence shown in SEQ ID NO: 2, 4, 7, 9, 11, 13, 15, 17, 19, 21, 23, 25, 27, 29, 31, 33, 35, 37, 39, 41, 43 or 45) which include less amino acids than the full length transactivator fusion protein, and exhibit at least one activity of a transactivator fusion protein. A biologically active portion of a transactivator fusion protein can be a polypeptide which is, for example, 10, 25, 50, 100, 200 or more amino acids in length. Biologically active portions of a transactivator fusion protein can be used as targets for developing agents which modulate a transactivator fusion protein mediated activity, e.g., regulation of gene expression.

In a preferred embodiment, the transactivator fusion protein has an amino acid sequence shown in SEQ ID NO: 2, 4, 7, 9, 11, 13, 15, 17, 19, 21, 23, 25, 27, 29, 31, 33, 35, 37, 39, 41, 43 or 45. In other embodiments, the transactivator fusion protein is substantially homologous to SEQ ID NO: 2, 4, 7, 9, 11, 13, 15, 17, 19, 21, 23, 25, 27, 29, 31, 33, 35, 37, 39, 41, 43 or 45, and retains the functional activity of the protein of SEQ ID NO: 2, 4, 7, 9, 11, 13, 15, 17, 19, 21, 23, 25, 27, 29, 31, 33, 35, 37, 39, 41, 43 or 45, yet differs in amino acid sequence due to natural allelic variation or mutagenesis. Accordingly, in another embodiment, the transactivator fusion protein is a protein which comprises an amino acid sequence at least about 80%, 85%, 90%, 95%, 98% or more homologous to SEQ ID NO: 2, 4, 7, 9, 11, 13, 15, 17, 19, 21, 23, 25, 27, 29, 31, 33, 35, 37, 39, 41, 43 or 45.

In one embodiment, a transactivator fusion protein of the invention is encoded by the nucleic acid sequence of SED ID NO: 1, 3, 5, 6, 8, 10, 12, 14, 16, 18, 20, 22, 24, 26, 28, 30, 32, 34, 36, 38, 40, 42, or 44. In another embodiment, a transactivator fusion protein is encoded by a nucleic acid molecule having 80% identity to SEQ ID NO: 1, 3, 5, 6, 8, 10, 12, 14, 16, 18, 20, 22, 24, 26, 28, 30, 32, 34, 36, 38, 40, 42, or 44.

The invention also provides chimeric transactivator fusion proteins. In a preferred embodiment, a chimeric transactivator fusion protein comprises at least one biologically active portion of a transactivator fusion protein. Within the fusion protein, the term "operatively linked" is intended to indicate that the transactivator fusion protein polypeptide and the non-transactivator fusion protein polypeptide are fused in-frame to each other. The non-transactivator fusion protein polypeptide can be fused to the N-terminus or C-terminus of the transactivator fusion protein polypeptide.

For example, in one embodiment, the chimeric protein comprises the transactivator fusion protein sequences are fused to the C-terminus of the GST sequences. Such fusion proteins can facilitate the purification of recombinant transactivator fusion protein.

In another embodiment, the chimeric protein is a transactivator fusion protein containing a heterologous signal sequence at its N-terminus. In certain host cells (e.g., mammalian host cells), expression and/or secretion transactivator fusion proteins can be increased through use of a heterologous signal sequence.

The chimeric transactivator fusion proteins of the invention can be incorporated into pharmaceutical compositions and administered to a subject in vivo. In addition, the chimeric transactivator fusion proteins can be used to affect the bioavailability of a transactivator fusion protein substrate. Moreover, the chimeric transactivator fusion proteins of the invention can be used as immunogens to produce anti-transactivator fusion protein antibodies in a subject, to purify transactivator fusion protein effector molecules, and in screening assays to identify molecules which interact with the transactivator fusion protein.

Preferably, a chimeric transactivator fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A transactivator fusion protein-encoding nucleic acid can be cloned into such an expression vector such that the heterologous moiety is linked in-frame to the transactivator fusion protein.

The present invention also pertains to variants of the transactivator fusion proteins which function as either transactivator fusion protein agonists (mimetics) or as transactivator fusion protein antagonists. Variants of the transactivator fusion proteins can be generated by mutagenesis, e.g., discrete point mutation or truncation of a transactivator fusion protein. An agonist of a transactivator fusion protein can retain substantially the same, or a subset, of the biological activities of the naturally occurring form of a transactivator fusion protein. An antagonist of a transactivator fusion protein can inhibit one or more of the activities of the original form of the transactivator fusion protein by, for example, competitively modulating a transactivator fusion protein-mediated activity of a transactivator fusion protein. Thus, specific biological effects can be elicited by treatment with a variant of limited function. In one embodiment, treatment of a subject with a variant having a subset of the biological activities of original form of the protein has a greater beneficial effect in a subject relative to treatment with the original form of the transactivator fusion protein.

Libraries of fragments of a transactivator fusion protein coding sequence can be used to generate a variegated population of transactivator fusion proteins for screening and subsequent selection of variants of transactivator fusion protein. In one embodiment, a library of coding sequence fragments can be generated by treating a double stranded PCR fragment of a transactivator fusion protein coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the transactivator fusion protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of transactivator fusion proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Reclusive ensemble mutagenesis (REM), a new technique which enhances the frequency of functional mutants in the libraries, can be used in combination with the screening assays to identify transactivator fusion protein variants (Arkin and Yourvan (1992) *Proc. Natl. Acad. Sci. USA* 89:7811-7815; Delgrave et al. (1993) *Protein Engineering* 6(3):327-331).

An isolated transactivator fusion protein, or a portion or fragment thereof, can be used as an immunogen to generate antibodies that bind the transactivator fusion protein using standard techniques for polyclonal and monoclonal antibody preparation. A full-length transactivator fusion protein can be used or, alternatively, the invention provides antigenic peptide fragments of transactivator fusion proteins for use as immunogens. The antigenic peptide of transactivator fusion protein comprises at least 8 amino acid residues of the amino acid sequence shown in SEQ ID NO: 2, 4, 7, 9, 11, 13, 15, 17, 19, 21, 23, 25, 27, 29, 31, 33, 35, 37, 39, 41, 43 or 45 and encompasses an epitope of a transactivator fusion protein such that an antibody raised against the peptide forms a specific immune complex with the transactivator fusion protein. Preferably, the antigenic peptide comprises at least 10 amino acid residues, more preferably at least 15 amino acid residues, even more preferably at least 20 amino acid residues, and most preferably at least 30 amino acid residues.

A transactivator fusion protein immunogen typically is used to prepare antibodies by immunizing a suitable subject, (erg., rabbit, goat, mouse or other mammal) with the immunogen. An appropriate immunogenic preparation can contain, for example, recombinantly expressed transactivator fusion protein or a chemically synthesized transactivator fusion protein polypeptide. The preparation can further include an adjuvant, such as Freund's complete or incomplete adjuvant, or similar immunostimulatory agent. Immunization of a suitable subject with an immunogenic transactivator fusion protein preparation induces a polyclonal anti-transactivator fusion protein antibody response.

Another aspect of the invention pertains to anti-transactivator fusion protein antibodies.

Polyclonal anti-transactivator fusion protein antibodies in accordance with the invention can be prepared by immunizing a suitable subject with a transactivator fusion protein immunogen. The anti-transactivator fusion protein antibody titer in the immunized subject can be monitored over time by standard techniques, such as with an enzyme linked immunosorbent assay (ELISA) using immobilized transactivator fusion protein. If desired, the antibody molecules directed against transactivator fusion protein can be isolated from the mammal (e.g. from the blood) and further purified by well known techniques, such as protein A chromatography to obtain the IgG fraction. At an appropriate time after immunization, e.g., when the anti-transactivator fusion protein antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem* .255: 4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.,* 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a transactivator fusion protein immunogen as described above, and the culture supernatants of the resulting hybridoma cells are screened to identify a hybridoma producing a monoclonal antibody that binds a transactivator fusion protein.

Any of the many well known protocols used for fusing lymphocytes and immortalized cell lines can be applied for the purpose of generating an anti-transactivator fusion protein monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line.

Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind the transactivator fusion protein, e.g., using a standard ELISA assay.

Additionally, recombinant anti-transactivator fusion protein antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al (1986) *Nature* 321:552-525; Verhoeyan et al. (1988) *Science* 239:1534; and Beidler et al. (1988) *J. Immunol.* 141:4053-4060.

An anti-transactivator fusion protein antibody (e.g., monoclonal antibody) can be used to isolate an transactivator fusion protein by standard techniques, such as affinity chromatography or immunoprecipitation. An anti-transactivator fusion protein antibody can facilitate the purification of recombinantly produced transactivator fusion proteins expressed in host cells. Moreover, an anti-transactivator fusion protein antibody can be used to detect a transactivator fusion protein (e.g., in a cellular lysate or cell supernatant) in order to evaluate the abundance and pattern of expression of the transactivator fusion protein. Anti-transactivator fusion protein antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Recombinant Expression Vectors

Another aspect of the invention pertains to vectors, preferably expression vectors, containing a nucleic acid encoding a transactivator fusion protein (or a portion thereof).

A recombinant expression vector of the invention can be a virus, or portion thereof, which allows for expression of a nucleic acid introduced into the viral nucleic acid. For example, replication defective retroviruses, adenoviruses and adeno-associated viruses can be used. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. The genome of adenovirus can be manipulated such that it encodes and expresses a transcriptional regulatory protein but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Alternatively, an adeno-associated virus vector such as that described in Tratschin et al. (1985) *Mol. Cell. Biol.* 5:3251-3260 can be used to express a transactivator protein of the present invention.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., transactivator fusion proteins, mutant forms of transactivator fusion proteins, fusion proteins, and the like).

The recombinant expression vectors of the invention can be designed for expression of transactivator fusion proteins in prokaryotic or eukaryotic cells. For example, transactivator fusion proteins can be expressed in bacterial cells such as *E. coli*, insect cells (using baculovirus expression vectors) yeast cells, mammalian cells, or plant cells. Appropriate cloning and expression vectors for use with bacterial, fungal, yeast, plant, and mammalian cellular hosts are known in the art, and are described in, for example, Powels et al. (*Cloning Vectors: A Laboratory Manual*, Elsevier, New York, 1985). For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Purified chimeric proteins can be utilized in transactivator fusion protein activity assays, or to generate antibodies specific for transactivator fusion proteins, for example.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

A number of vectors exist for the expression of recombinant proteins in yeast. Examples of vectors for expression in yeast *S. cerevisiae* include pYepSec1 (Baldari. et al., (1987) *Embo J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). In addition, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due to the presence of the pBR322 ori, and in *S. cerevisiae* due to the replication determinant of the yeast 2 micron plasmid. In addition, drug resistance markers, e.g., antibiotics which confer resistance in fungal systems, can be used. Suitable promoters for function in yeast include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Req.* 7, 149 (1968); and Holland et al. *Biochemistry* 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EPO Publication. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. Finally, promoters that are active in only one of the two haploid mating types may be appropriate in certain circumstances. Among these haploid-specific promoters, the pheromone promoters MFa1 and MFα1 are of particular interest.

In a preferred embodiment, the recombinant expression vector of the invention is a plasmid selected from the group consisting of: pCM190GFP+, pUHD 15-1, pREP9, and pUHD.

Alternatively, transactivator fusion proteins can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences. When used in mammalian cells, a recombinant expression vector's control functions are often provided by viral genetic material. For example, commonly used promoters are derived from polyoma, Adenovirus 2, cytomegalovirus and Simian Virus 40. Use of viral regulatory elements to direct expression of the fusion protein can allow for high level constitutive expression of the fusion protein in a variety of host cells. Examples of mammalian expression vectors include pCDM8 (Seed, B. (1987) *Nature* 329:840) and pMT2PC (Kaufman et al. (1987) *EMBO J.* 6:187-195).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to the transactivator fusion protein mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Host Cells

Another aspect of the invention pertains to host cells into which a transactivator fusion protein nucleic acid molecule of the invention is introduced, e.g., a transactivator fusion protein nucleic acid molecule within a recombinant expression vector or a transactivator fusion protein nucleic acid molecule containing sequences which allow it to homologously recombine into a specific site of the host cell's genome.

Nucleic acid encoding the fusion protein can be introduced into a host cell by standard techniques for transfecting eukaryotic cells. The term "transfecting" or "transfection" is intended to encompass all conventional techniques for introducing nucleic acid into host cells, including calcium phosphate co-precipitation, DEAE-dextran-mediated transfection, lipofection, electroporation and microinjection. Suitable methods for transfecting host cells can be found in Sambrook et al. (*Molecular Cloning: A Laboratory Manual,* 2nd Edition, Cold Spring Harbor Laboratory press (1989)), and other laboratory textbooks. Nucleic acid can also be transferred into cells in vivo, for example by application of a delivery mechanism suitable for introduction of nucleic acid into cells in vivo, such as retroviral vectors (see e.g., Ferry, N et al. (1991) *Proc. Natl. Acad. Sci. USA* 88:8377-8381; and Kay, M. A. et al. (1992) *Human Gene Therapy* 3:641-647), adenoviral vectors (see e.g., Rosenfeld, M. A. (1992) *Cell* 68:143-155; and Herz, J. and Gerard, R. D. (1993) *Proc. Natl. Acad. Sci. USA* 90:2812-2816), receptor-mediated DNA uptake (see e.g., Wu, G. and Wu, C. H. (1988) *J. Biol. Chem.* 263: 14621; Wilson et al. (1992) *J. Biol. Chem.* 267:963-967; and U.S. Pat. No. 5,166,320), direct injection of DNA (see e.g., Acsadi et al. (1991) *Nature* 332: 815-818; and Wolff et al. (1990) *Science* 247:1465-1468) or particle bombardment (see e.g., Cheng, L. et al. (1993) *Proc. Natl. Acad. Sci. USA* 90:4455-4459; and Zelenin, A. V. et al. (1993) *FEBS Letters* 315:29-32). Thus, for gene therapy purposes, cells can be modified in vitro and administered to a subject or, alternatively, cells can be directly modified in vivo.

The number of host cells transformed with a nucleic acid of the invention will depend, at least in part, upon the type of recombinant expression vector used and the type of transfection technique used. Nucleic acid can be introduced into a host cell transiently, or more typically, for long term regulation of gene expression, the nucleic acid is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acid of interest. Preferred selectable markers include those which confer resistance to certain drugs, such as G418 and hygromycin. Selectable markers can be introduced on a separate plasmid from the nucleic acid of interest or, are introduced on the same plasmid. Host cells transfected with a nucleic acid of the invention (e.g., a recombinant expression vector) and a gene for a selectable marker can be identified by selecting for cells using the selectable marker. For example, if the selectable marker encodes a gene conferring neomycin resistance, host cells which have taken up nucleic acid can be selected with G418. Cells that have incorporated the selectable marker gene will survive, while the other cells die.

A host cell transfected with a nucleic acid encoding a fusion protein of the invention can be further transfected with one or more nucleic acids which serve as the target for the fusion protein. The target nucleic acid comprises a nucleotide sequence to be transcribed operatively linked to at least one tet operator sequence.

A host cell of the invention, such as a prokaryotic or eukaryotic host cell in culture, can be used to produce (i.e., express) a transactivator fusion protein. Accordingly, the invention further provides methods for producing a transactivator fusion protein using the host cells of the invention. In one embodiment, the method comprises culturing the host cell of the invention (into which a recombinant expression vector encoding a transactivator fusion protein has been introduced) in a suitable medium such that a transactivator fusion protein is produced.

Expression of a Transactivator Fusion Protein

A fusion protein of the invention is expressed in a eukaryotic cell by introducing nucleic acid encoding the fusion protein into a host cell, wherein the nucleic acid is in a form suitable for expression of the fusion protein in the host cell. For example, a recombinant expression vector of the invention, encoding the fusion protein, is introduced into a host cell. Alternatively, nucleic acid encoding the fusion protein which is operatively linked to regulatory sequences (e.g., promoter sequences) but without additional vector sequences can be introduced into a host cell.

In addition to cell lines, the invention is applicable to normal (e.g., primary) cells, such as cells to be modified for gene therapy purposes or embryonic cells modified to create a transgenic or homologous recombinant animal. Examples of cell types of particular interest for gene therapy purposes include hematopoietic stem cells, myoblasts, beta cells of the pancreas, hepatocytes, lymphocytes, neuronal cells and skin epithelium and airway epithelium. Primary cells of interest also include cell lines in which genes involved in cell cycle control are placed under tTA/rtTA regulation. Such novel cell lines would be conditionally proliferating and can recover their quiescent, differentiated state upon growth arrest via addition or withdrawal of tetracyclines, and will be of use in pharmacology and gene therapy. Additionally, for transgenic or homologous recombinant animals, embryonic stem cells and fertilized oocytes can be modified to contain nucleic acid encoding a transactivator fusion protein. Moreover, plant cells can be modified to create transgenic plants.

Transgenic Organisms

Nucleic acid a transactivator fusion protein can transferred into a fertilized oocyte of a non-human animal to create a transgenic animal which expresses the fusion protein of the invention in one or more cell types. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell types or tissues of the transgenic animal. In one embodiment, the non-human animal is a mouse, although the invention is not limited thereto. In other embodiments, the transgenic animal is a goat, sheep, pig, cow or other domestic farm animal. Such transgenic animals are useful for large scale production of proteins (so called "gene pharming").

A transgenic animal can be created, for example, by introducing a nucleic acid encoding the fusion protein (typically linked to appropriate regulatory elements, such as a constitutive or tissue-specific enhancer) into the male pronuclei of a fertilized oocyte, e.g., by microinjection, and allowing the oocyte to develop in a pseudopregnant female foster animal. Intronic sequences and polyadenylation signals can also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009 and Hogan, B. et al., (1986) *A Laboratory Manual*, Cold Spring Harbor, N.Y., Cold Spring Harbor Laboratory. A transgenic founder animal can be used to breed additional animals carrying the transgene. Transgenic animals carrying a transgene encoding the fusion protein of the invention can further be bred to other transgenic animals carrying other transgenes, e.g., to a transgenic animal which contains a gene operatively linked to a tet operator sequence (discussed in more detail in Section III below).

It will be appreciated that, in addition to transgenic animals, the regulatory system described herein can be applied to other transgenic organisms, such as transgenic plants. Transgenic plants can be made by conventional techniques known in the art. Accordingly, the invention encompasses non-human transgenic organisms, including animals and plants, that contains cells which express the transactivator fusion protein of the invention (i.e., a nucleic acid encoding the transactivator is incorporated into one or more chromosomes in cells of the transgenic organism).

Homologous Recombinant Organisms

The invention also provides a homologous recombinant non-human organism expressing the fusion protein of the invention. In one embodiment, the non-human animal is a mouse, although the invention is not limited thereto. An animal can be created in which nucleic acid encoding the fusion protein has been introduced into a specific site of the genome, i.e., the nucleic acid has homologously recombined with an endogenous gene.

To create such a homologous recombinant animal, a vector is prepared which contains DNA encoding the fusion protein flanked at its 5' and 3' ends by additional nucleic acid of a eukaryotic gene at which homologous recombination is to occur. The additional nucleic acid flanking that encoding the fusion protein is of sufficient length for successful homologous recombination with the eukaryotic gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced DNA has homologously recombined with the endogenous DNA are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA. These "germline transmission" animals can further be mated to animals carrying a gene operatively linked to at least one tet operator sequence (discussed in more detail in Section III below).

In addition to the homologous recombination approaches described above, enzyme-assisted site-specific integration systems are known in the art and can be applied to the components of the regulatory system of the invention to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nucl. Acids Res.* 21:2025-2029; and Fukushige, S. and Sauer, B. (1992) *Proc. Natl. Acad. Sci. USA* 89:7905-7909) and the FLP recombinase-FRT target system (e.g., as described in Dang, D. T. and Perrimon, N. (1992) *Dev. Genet.* 13:367-375; and Fiering, S. et al. (1993) *Proc. Natl. Acad. Sci. USA* 90:8469-8473).

Regulation of Expression of tet Operator-Linked Nucleotide Sequences

Expression of a tet operator-linked nucleotide sequences is regulated by a transactivator fusion protein of the invention. Thus, the fusion protein and the target nucleic acid are both present in a host cell or organism. The presence of both the transactivator fusion protein and the target transcription unit in the same host cell or organism can be achieved in a number of different ways. For example, a host cell can be transfected with one nucleic acid of the expression system (e.g., encoding the transactivator fusion protein), stably transfected cells can be selected and then the transfected cells can be re-transfected (also referred to as "supertransfected") with nucleic acid corresponding to the other nucleic acid of the expression system (e.g., the target nucleic acid to be transcribed). Two distinct selectable markers can be used for selection, e.g., uptake of the first nucleic acid can be selected with G418 and uptake of the second nucleic acid can be selected with hygromycin. Alternatively, a single population of cells can be transfected with nucleic acid corresponding to both components of the system.

The host cell may be a cell cultured in vitro or a cell present in vivo (e.g., a cell targeted for gene therapy). The host cell can further be a fertilized oocyte, embryonic stem cell or any other embryonic cell used in the creation of non-human transgenic or homologous recombinant animals. Transgenic or homologous recombinant animals which comprise both nucleic acid components of the expression system can be created by introducing both nucleic acids into the same cells at an embryonic stage, or more preferably, an animal which carries one nucleic acid component of the system in its genome is mated to an animal which carries the other nucleic acid component of the system in its genome. Offspring which have inherited both nucleic acid components can then be identified by standard techniques.

In a host cell which carries nucleic acid encoding a transactivator fusion protein of the invention and a nucleotide sequence operatively linked to the tet operator sequence (i.e., gene of interest to be transcribed), transcription of the nucleotide sequence operatively linked to the tet operator sequence(s) can be regulated by tetracycline, or analogs thereof. Accordingly, another aspect of the invention pertains to methods for stimulating transcription of a nucleotide sequence operatively linked to a tet operator sequence in a host cell or animal which expresses a transactivator fusion protein of the invention. The methods involve contacting the cell with tetracycline or a tetracycline analogue or administering tetracycline or a tetracycline analogue to a subject containing the cell.

To induce gene expression in a cell in vitro, the cell is contacted with Tc or an analog thereof by culturing the cell in a medium containing the compound. To induce gene expression in vivo, cells within a subject are contacted with Tc or an analog thereof by administering the compound to the subject. The term "subject" is intended to include humans and other non-human mammals including monkeys, cows, goats, sheep, dogs, cats, rabbits, rats, mice, and transgenic and homologous recombinant species thereof. Furthermore, the term "subject" is intended to include plants, such as transgenic plants. Tc or a Tc analog can be administered to a subject by any means effective for achieving an in viva concentration sufficient for gene induction. Examples of suitable modes of administration include oral administration (e.g., dissolving the inducing agent in the drinking water), slow release pellets and implantation of a diffusion pump. To administer Tc or a Tc analog to a transgenic plant, the inducing agent can be dissolved in water administered to the plant.

The ability to use different Tc analogues as inducing agents in this system allows for modulate the level of expression of a tet operator-linked nucleotide sequence. Thus, an appropriate tetracycline analog is chosen as an inducing agent based upon the desired level of induction of gene expression. It is also possible to change the level of gene expression in a host cell or animal over time by changing the Tc analogue used as the inducing agent. For example, there may be situations where it is desirable to have a strong burst of gene expression initially and then have a sustained lower level of gene expression. Accordingly, an analog which stimulates a high levels of transcription can be used initially as the inducing agent and then the inducing agent can be switched to an analogue which stimulates a lower level of transcription. Moreover, when regulating the expression of multiple nucleotide sequences (e.g., when one sequence is regulated by a one of class tet operator sequence(s) and the other is regulated by another class of tet operator sequence(s)), it may be possible to independently vary the level of expression of each sequence depending upon which transactivator fusion protein is used to regulate transcription and which Tc analogue(s) is used as the inducing agent. Different transactivator fusion proteins are likely to exhibit different levels of responsiveness to Tc analogues. The level of induction of gene expression by a particular combination of transactivator fusion protein and inducing agent (Tc or Tc analogue) can be determined by techniques described herein. Additionally, the level of gene expression can be modulated by varying the concentration of the inducing agent. Thus, the expression system of the invention provides a mechanism not only for turning gene expression on or off, but also for "fine tuning" the level of gene expression at intermediate levels depending upon the type and concentration of inducing agent used.

Applications of the Invention

The present invention is widely applicable to a variety of situations where it is desirable to be able to turn gene expression on and off, or regulate the level of gene expression, in a rapid, efficient and controlled manner without causing pleiotropic effects or cytotoxicity. For example, the nucleic acids and proteins of the invention have use in the study of cellular development and differentiation in eukaryotic cells, plants and animals. The expression of oncogenes can be regulated in a controlled manner in cells to study their function. Additionally, the system can be used to regulate the expression of site-specific recombinases, such as CRE or FLP, to allow for irreversible modification of the genotype of a transgenic organism under controlled conditions at a particular stage of development. For example, drug resistance markers inserted into the genome of transgenic plants that allow for selection of a particular transgenic plant could be irreversibly removed via a Tc-regulated site specific recombinase. Other applications of the regulatory system of the invention include:

A. Gene Therapy

The invention may be particularly useful for gene therapy purposes, in treatments for either genetic or acquired diseases. The general approach of gene therapy involves the introduction of nucleic acid into cells such that one or more gene products encoded by the introduced genetic material are produced in the cells to restore or enhance a functional activity. For reviews on gene therapy approaches see Anderson, W. F. (1992) Science 256:808-813; Miller, A. D. (1992) Nature 357:455-460; Friedmann, T. (1989) Science 244:1275-1281; and Cournoyer, D., et al (1990) Curr. Opin. Biotech. 1:196-208. However, current gene therapy vectors typically utilize constitutive regulatory elements which are responsive to endogenous transcriptions factors. These vector systems do not allow for the ability to modulate the level of gene expression in a subject. In contrast, the proteins, modulator compounds and gene regulatory sequences identified by the methods of the invention provides the ability to modulate gene expression in a cell in vitro or in vivo.

To use the system of the invention for gene therapy purposes, in one embodiment, cells of a subject in need of gene therapy are modified to contain 1) nucleic acid encoding a transactivator fusion protein of the invention in a form suitable for expression of the transactivator in the host cells and 2) a gene of interest (e.g., for therapeutic purposes) operatively linked to a tet operator sequence(s). The cells of the subject can be modified ex vivo and then introduced into the subject or the cells can be directly modified in vivo. Expression of the gene of interest in the cells of the subject is then stimulated by administering Tc or a Tc analogue to the patient. The level of gene expression can be varied depending upon which particular Tc analogue is used as the inducing agent. The level of gene expression can also be modulated by adjusting the dose of the tetracycline, or analogue thereof, administered to the patient to thereby adjust the concentration achieved in the circulation and the tissues of interest.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system. The pharmaceutical compositions can be included in a container, pack, or dispenser together with instructions for administration.

Conventional detection methods known in the art, such as an enzyme linked immunosorbent assay, can be used to monitor the expression of the regulated protein of interest in the host cells and the concentration of Tc or Tc analogue can be varied until the desired level of expression of the protein of interest is achieved. Accordingly, expression of a protein of interest can be adjusted according to the medical needs of an individual, which may vary throughout the lifetime of the individual. To stop expression of the gene of interest in cells of the subject, administration of the inducing agent is stopped. Thus, the regulatory system of the invention offers the advantage over constitutive regulatory systems of allowing for modulation of the level of gene expression depending upon the requirements of the therapeutic situation.

Genes of particular interest to be expressed in cells of a subject for treatment of genetic or acquired diseases include those encoding adenosine deaminase, Factor VIII, Factor IX, dystrophin, β-globin, LDL receptor, CFTR, insulin, erythropoietin, anti-angiogenesis factors, growth hormone, glucocerebrosidase, β-glucouronidase, α1-antitrypsin, phenylalanine hydroxylase, tyrosine hydroxylase, ornithine transcarbamylase, arginosuccinate synthetase, UDP-glucuronysyl transferase, apoA1, TNF, soluble TNF receptor, interleukins (e.g., IL-2), interferons (e.g., α- or γ-IFN) and other cytokines and growth factors. Cells types which can be modified for gene therapy purposes include hematopoietic stem cells, myoblasts, hepatocytes, lymphocytes, skin epithelium and airway epithelium. For further descriptions of cell types, genes and methods for gene therapy see e.g., Wilson, J. M et al. (1988) Proc. Natl. Acad. Sci. USA 85:3014-3018; Armentano, D. et al. (1990) Proc. Natl. Acad. Sci. USA 87:6141-6145; Wolff, J. A. et al. (1990) Science 247:1465-1468; Chowdhury, J. R. et al. (1991) Science 254:1802-1805; Ferry, N. et al. (1991) Proc. Natl. Acad. Sci. USA 88:8377-8381; Wilson, J. M. et al. (1992) J. Biol. Chem. 267:963-967; Quantin, B. et al. (1992) Proc. Natl. Acad. Sci. USA 89:2581-2584; Dai, Y. et al. (1992) Proc. Natl. Acad. Sci. USA 89:10892-10895; van Beusechem, V. W. et al (1992) Proc. Natl. Acad. Sci. USA 89:7640-7644; Rosenfeld, M. A. et al. (1992) Cell 68:143-155; Kay, M. A. et al. (1992) Human Gene Therapy 3:641-647; Cristiano, R. J. et al. (1993) Proc. Natl. Acad. Sci. USA 90:2122-2126; Hwu, P. et al (1993) J. Immunol. 150: 4104-4115; and Herz, J. and Gerard, R. D. (1993) Proc. Natl. Acad. Sci. USA 90:2812-2816.

Gene therapy applications of particular interest in cancer treatment include overexpression of a cytokine gene (e.g., TNF-α) in tumor infiltrating lymphocytes or ectopic expression of cytokines in tumor cells to induce an anti-tumor immune response at the tumor site), expression of an enzyme in tumor cells which can convert a non-toxic agent into a toxic agent, expression of tumor specific antigens to induce an anti-tumor immune response, expression of tumor suppressor genes (e.g., p53 or Rb) in tumor cells, expression of a multi-drug resistance gene (e.g., MDR1 and/or MRP) in bone marrow cells to protect them from the toxicity of chemotherapy.

Gene therapy applications of particular interest in treatment of viral diseases include expression of trans-dominant negative viral transactivation proteins, such as trans-dominant negative tat and rev mutants for HIV or trans-dominant ICp4 mutants for HSV (see e.g., Balboni, P. G. et al (1993) J. Med. Virol. 41:289-295; Liem, S. E. et al. (1993) Hum. Gene Ther. 4:625-634; Malim, M. H. et al. (1992) J. Exp. Med. 176:1197-1201; Daly, T. J. et al (1993) Biochemistry 32:8945-8954; and Smith, C. A. et al. (1992) Virology 191: 581-588), expression of trans-dominant negative envelope proteins, such as env mutants for HIV (see e.g., Steffy, K. R. et al. (1993) J. Virol. 67:1854-1859), intracellular expression of antibodies, or fragments thereof, directed to viral products ("internal immunization", see e.g., Marasco, W. A. et al. (1993) Proc. Natl. Acad. Sci. USA 90:7889-7893) and expression of soluble viral receptors, such as soluble CD4. Additionally, the system of the invention can be used to conditionally express a suicide gene in cells, thereby allowing for elimination of the cells after they have served an intended function. For example, cells used for vaccination can be eliminated in a subject after an immune response has been generated the subject by inducing expression of a suicide gene in the cells by administering Tc or a Tc analogue to the subject.

The Tc-controlled regulatory system of the invention has numerous advantages properties that it particularly suitable for application to gene therapy. For example, the system provides an "on"/"off" switch for gene expression that allows for regulated dosing of a gene product in a subject. There are several situations in which it may be desirable to be able to provide a gene product at specific levels and/or times in a regulated manner, rather than simply expressing the gene product constitutively at a set level. For example, a gene of interest can be switched "on" at fixed intervals (e.g., daily, alternate days, weekly, etc.) to provide the most effective level of a gene product of interest at the most effective time. The level of gene product produced in a subject can be monitored by standard methods (e.g., direct monitoring using an immunological assay such as ELISA or RIA or indirectly by monitoring of a laboratory parameter dependent upon the function of the gene product of interest, e.g., blood glucose levels and the like). This ability to turn "on" expression of a gene at discrete time intervals in a subject while also allowing for the gene to be kept "off" at other times avoids the need for continued administration of a gene product of interest at intermittent intervals. This approach avoids the need for repeated injections of a gene product, which may be painful and/or cause side effects and would likely require continuous visits to a physician. In contrast, the system of the invention avoids these drawbacks. Moreover, the ability to turn "on"

expression of a gene at discrete time intervals in a subject allows for focused treatment of diseases which involve "flare tips" of activity (e.g., many autoimmune diseases) only at times when treatment is necessary during the acute phase when pain and symptoms are evident. At times when such diseases are in remission, the expression system can be kept in the "off" state.

Gene therapy applications that may particularly benefit from this ability to modulate gene expression during discrete time intervals include the following non-limiting examples:

Rheumatoid arthritis—genes which encode gene products that inhibit the production of inflammatory cytokines (e.g., TNF, IL-1 and IL-12) can be expressed in subjects. Examples of such inhibitors include soluble forms of a receptor for the cytokine. Additionally or alternatively, the cytokines IL-10 and/or IL-4 (which stimulate a protective Th2-type response) can be expressed. Moreover, a glucocorticomimetic receptor (GCMR) can be expressed.

Hypopituitarism—the gene for human growth hormone can be expressed in such subjects only in early childhood, when gene expression is necessary, until normal stature is achieved, at which time gene expression can be downregulated.

Wound healing/Tissue regeneration—Factors (e.g., growth factors, angiogenic factors, etc.) necessary for the healing process can be expressed only when needed and then downregulated.

Anti-Cancer Treatments—Expression of gene products useful in anti-cancer treatment can be limited to a therapeutic phase until retardation of tumor growth is achieved, at which time expression of the gene product can be downregulated. Possible systemic anti-cancer treatments include use of tumor infiltrating lymphocytes which express immunostimulatory molecules (e.g., IL-2, IL-12 and the like), angiogenesis inhibitors (PF4, IL-12, etc.), Her-regulin, Leukoregulin (see PCT Publication No. WO 85/04662), and growth factors for bone marrow support therapy, such as G-CSF, GM-CSF and M-CSF. Regarding the latter, use of the regulatory system of the invention to express factors for bone marrow support therapy allows for simplified therapeutic switching at regular intervals from chemotherapy to bone marrow support therapy (similarly, such an approach can also be applied to AIDS treatment, e.g., simplified switching from anti-viral treatments to bone marrow support treatment). Furthermore, controlled local targeting of anti-cancer treatments are also possible. For example, expression of a suicide gene by a regulator of the invention, wherein the regulator itself is controlled by, for example, a tumor-specific promoter or a radiation-induced promoter.

In another embodiment, the regulatory proteins of the invention are used to express angiogenesis inhibitor(s) from within a tumor via a transgene regulated by the system of the invention. Expression of angiogenesis inhibitors in this manner may be more efficient than systemic administration of the inhibitor and would avoid any deleterious side effects that might accompany systemic administration. In particular, restricting angiogenesis inhibitor expression to within tumors could be particularly useful in treating cancer in children still undergoing angiogenesis associated with normal cell growth.

In another embodiment, high level regulated expression of cytokines may represent a method for focusing a patients own immune response on tumor cells. Tumor cells can be transduced to express chemoattractant and growth promoting cytokines important in increasing an individual's natural immune response. Because the highest concentrations of cytokines will be in the proximity of the tumor, the likelihood of eliciting an immunological response to tumor antigens is increased. A potential problem with this type of therapy is that those tumor cells producing the cytokines will also be targets of the immune response and therefor the source of the cytokines will be eliminated before eradication of all tumor cells can be certain. To combat this, expression of viral proteins known to mask infected cells from the immune system can be placed under regulation, along with the cytokine gene(s), in the same cells. One such protein is the E19 protein from adenovirus (see e.g., Cox, *Science* 247:715). This protein prevents transport of class I HLA antigens to the surface of the cell and hence prevents recognition and lysis of the cell by the host's cytotoxic T cells. Accordingly, regulated expression of E19 in tumor cells could shield cytokine producer cells from cytotoxic T cells during the onset of an immune response provoked by cytokine expression. After a sufficient period of time has elapsed to eradicate all tumor cells but those expressing E19, E19 expression can be turned off, causing these cells then to fall victim to the provoked anti-tumor imine response.

Benign prostatic hypertrophy—Similar to the above, a suicide gene can be regulated by a regulator of the invention, wherein the regulator itself is controlled by, for example, a prostate-specific promoter.

The ability to express a suicide gene (e.g., an apoptosis gene, TK gene, etc) in a controlled manner using the regulatory system of the invention adds to the general safety and usefulness of the system. For example, at the end of a desired therapy, expression of a suicide gene can be triggered to eliminate cells carrying the gene therapy vector, such as cells in a bioinert implant, cells that have disseminated beyond the intended original location, etc. Moreover, if a transplant becomes tumorigenic or has side effects, the cells can be rapidly eliminated by induction of the suicide gene. The use of more than one Tc-controlled "on"/"off" switch in one cell allows for completely independent regulation of a suicide gene compared to regulation of a gene of therapeutic interest (as described in detail herein).

The regulatory proteins of the invention further offer the ability to establish a therapeutically relevant expression level for a gene product of interest in a subject, in contrast to unregulated constitutive expression which offers no flexibility in the level of gene product expression that can be achieved. A physiologically relevant level of gene product expression can be established based on the particular medical need of the subject, e.g., based on laboratory tests that monitor relevant gene product levels (using methods as described above). In addition to the clinical examples and gene products already discussed above with gene to dosing of the gene product, other therapeutically relevant gene products which can be expressed at a desired level at a desired time include: Factor XIII and IX in hemophiliacs (e.g., expression can be elevated during times of risk of injury, such as during sports); insulin or amylin in diabetics (as needed, depending on the state of disease in the subject, diet, etc.); erythropoietin to treat erythrocytopenia (as needed, e.g., at end-stage renal failure); low-density lipoprotein receptor (LDLr) or very low-density lipoprotein receptor (VLDLr) for arteriosclerosis or gene therapy in liver (e.g., using ex vivo implants). Applications to treatment of central nervous system disorders are also encompassed. For example, in Alzheimer's disease, "fine tuned" expression of choline acetyl transferase (ChAT) to restore acetylcholine levels, neurotrophic factors (e.g., NGF, BDNGF and the like) and/or complement inhibitors (e.g., sCR1, sMCP, sDAF, sCD59 etc.) can be accomplished. Such gene products can be provided, for example, by transplanted cells expressing the gene products in a regulated manner using the system of the invention. Moreover, Parkinson's disease can be treated by "fine tuned" expression of tyrosine hydroxylase (TH) to increase levodopa and dopamine levels.

In addition to the pertinacious gene products discussed above, gene products that are functional RNA molecules (such as anti-sense RNAs and ribozymes) can be expressed in a controlled manner in a subject for therapeutic purposes. For example, a ribozyme can be designed which discriminates between a mutated form of a gene and a wild-type gene. Accordingly, a "correct" gene (e.g., a wild-type p53 gene) can be introduced into a cell in parallel with introduction of a regulated ribozyme specific for the mutated form of the gene (e.g., a mutated endogenous p53 gene) to remove the defective mRNA expressed from the endogenous gene. This approach is particularly advantageous in situations in which a gene product from the defective gene would interfere with the action of the exogenous wild-type gene.

Expression of a gene product in a subject using the regulatory proteins of the invention is modulated using tetracycline or analogues thereof. Such drugs can be administered by any route appropriate for delivery of the drug to its desired site of action (e.g., delivery to cells containing a gene whose expression is to be regulated). Depending on the particular cell types involved, preferred routes of administration may include oral administration, intravenous administration and topical administration (e.g. using a transdermal patch to reach cells of a localized transplant under the skin, such as keratinocytes, while avoiding any possible side effects from systemic treatment).

In certain gene therapy situations, it may be necessary or desirable to take steps to avoid or inhibit unwanted immune reactions in a subject receiving treatment. To avoid a reaction against the cells expressing the therapeutic gene product, a subject's own cells are generally used, when possible, to express the therapeutic gene product, either by in vivo modification of the subject's cells or by obtaining cells from the subject, modifying them ex vivo and returning them to the subject. In situations where allogeneic or xenogeneic cells are used to express a gene product of interest, the regulatory system of the invention, in addition to regulating a therapeutic gene, can also be used to regulate one or more genes involved in the immune recognition of the cells to inhibit an immune reaction against the foreign cells. For example, cell-surface molecules involved in recognition of a foreign cell by T lymphocytes can be downmodulated on the surface of a foreign cell used for delivery of a therapeutic gene product, such as by regulated expression in the foreign cell of a ribozyme which cleaves the mRNA encoding the cell-surface molecule. Particularly preferred cell surface molecules which can be downmodulated in this manner to inhibit an unwanted immune response include class I and/or class II major histocompatibility complex (MHC) molecules, costimulatory molecules (e.g., B7-1 and/or B7-2), CD40, and various "adhesion" molecules, such as ICAM-1 or ICAM-2. Using approaches described herein for independent but coordinate regulation of multiple genes in the same cell, the down-regulation of expression of a cell-surface molecule(s) in a host cell can be coordinated with the up-regulation of expression of a therapeutic gene. Accordingly, after therapy is completed and expression of the therapeutic gene is halted, expression of the endogenous cell surface molecule(s) can be restored to normal.

Furthermore, as described above regarding anti-cancer treatments, a viral protein (e.g., adenovirus E19 protein) that downmodulates expression of MHC antigens can be regulated in host cells using the system of the invention as a means of avoiding unwanted immunological reactions.

In addition to avoiding or inhibiting an immune response against a foreign cell delivering a therapeutic gene product, it may also be necessary, in certain situations, to avoid or inhibit an immune response against certain components of the regulatory system of the invention (e.g., the regulator fusion proteins described herein) that are expressed in a subject, since these fusion proteins contain non-mammalian polypeptides that may stimulate an unwanted immune reaction. In this regard, regulator fusion proteins can be designed and/or selected for a decreased ability to stimulate an immune response in a host. For example, a transcriptional activator domain for use in the regulator fusion protein can be chosen which has minimal immunogenicity. In this regard, a wild-type transcriptional activation domain of the herpes simplex virus protein VP16 may not be a preferred transcriptional activation domain for use in vivo, since it may stimulate an immune response in mammals. Alternative transcriptional activation domains can be used, as described herein, based on their reduced immunogenicity in a subject. For example, a transcriptional activation domain of a protein of the same species as the host may be preferred (e.g., a transcriptional activation domain from a human protein for use of a regulatory fusion protein in humans). Alternatively, a regulatory fusion protein of the invention can be modified to reduce its immunogenicity in subjects, e.g., by identifying and modifying one or more dominant T cell epitopes within a polypeptide of the fusion protein (e.g., either the Tet repressor moiety or the transcriptional modulator moiety, such as a VP16 polypeptide). Such T cell epitopes can be identified by standard methods and altered by mutagenesis, again by standard methods. A modified form of a regulator fusion protein can then be selected which retains its original transcriptional regulatory ability yet which exhibits reduced immunogenicity in a subject as compared to an unmodified fusion protein.

In addition to the foregoing, all conventional methods for generally or specifically downmodulating immune responses in subjects can be combined with the use of the regulatory system of the invention in situations where inhibition of immune responses is desired. General immunosuppressive agents, such as cyclosporin A and/or FK506, can be administered to the subject. Alternatively, immunomodulatory agents which may allow for more specific immunosuppression can be used. Such agents may include inhibitors of costimulatory molecules (e.g., a CTLA4Ig fusion protein, soluble CD4, anti-CD4 antibodies, anti-B7-1 and/or anti-B7-2 antibodies or anti-gp39 antibodies).

Finally, in certain situations, a delivery vehicle for cells expressing a therapeutic gene can be chosen which minimizes exposure of transplanted cells to the immune system. For example, cells can be implanted into bioinert capsules/biocompatible membranes with pores which allow for diffusion of proteins (e.g., a therapeutic gene product of interest) out of the implant and diffusion of nutrients and oxygen into the implant but which prevent entry of immune cells, thereby avoiding exposure of the transplanted cells to the immune system (as has been applied to islet cell transplantation).

The transactivator fusion protein nucleic acid molecules, fragments of transactivator fusion proteins, and anti-transactivator fusion protein antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration.

B. Production of Proteins in Vitro

Large scale production of a protein of interest can be accomplished using cultured cells in vitro which have been modified to contain: 1) a nucleic acid encoding a transactivator fusion protein of the invention in a form suitable for expression of the transactivator in the cells; and 2) a gene encoding the protein of interest operatively linked to a tet operator sequence(s). For example, mammalian, yeast or fungal cells can be modified to contain these nucleic acid components as described herein. The modified mammalian, yeast or fungal cells can then be cultured by standard fermentation techniques in the presence of Tc or an analogue thereof to induce expression of the gene and produce the protein of interest. Accordingly, the invention provides a production process for isolating a protein of interest. In the process, a host cell (e.g., a yeast or fungus), into which has been introduced both a nucleic acid encoding a transactivator fusion protein of the invention and a nucleic acid encoding the protein of the interest operatively linked to at least one tet operator sequence, is grown at production scale in a culture medium in the presence of tetracycline or a tetracycline analogue to stimulate transcription of the nucleotides sequence encoding the protein of interest (i.e., the nucleotide sequence operatively linked to the tet operator sequence(s)) and the protein of interest is isolated from harvested host cells or from the culture medium. Standard protein purification techniques can be used to isolate the protein of interest from the medium or from the harvested cells.

C. Production of Proteins in Vivo

The invention also provides for large scale production of a protein of interest in animals, such as in transgenic farm animals. Advances in transgenic technology have made it possible to produce transgenic livestock, such as cattle, goats, pigs and sheep (reviewed in Wall, R. J. et al. (1992) *J. Cell. Biochem.* 49:113-120; and Clark, A. J. et al. (1987) *Trends in Biotechnology* 5:20-24). Accordingly, transgenic livestock carrying in their genome the components of the inducible regulatory system of the invention can be constructed, wherein a gene encoding a protein of interest is operatively linked to at least one tet operator sequence. Gene expression, and thus protein production, is induced by administering Tc (or analogue thereof) to the transgenic animal. Protein production can be targeted to a particular tissue by linking the nucleic acid encoding the transactivator fusion protein to an appropriate tissue-specific regulatory element(s) which limits expression of the transactivator to certain cells. For example, a mammary gland-specific regulatory element, such as the milk whey promoter (U.S. Pat. No. 4,873,316 and European Application Publication No. 264,166), can be linked to the transactivator transgene to limit expression of the transactivator to mammary tissue. Thus, in the presence of Tc (or analogue thereof), the protein of interest will be produced in the mammary tissue of the transgenic animal. The protein can be designed to be secreted into the milk of the transgenic animal, and if desired, the protein can then be isolated from the milk.

D. Animal Models of Human Disease

The transcriptional activator proteins of the invention can be used alone or in combination to stimulate expression of specific genes in animals to mimic the pathophysiology of human disease to thereby create animal models of human disease. For example, in a host animal, a gene of interest thought to be involved in a disease can be placed under the transcriptional control of one or more tet operator sequences (e.g., by homologous recombination, as described herein). Such an animal can be mated to a second animal carrying one or more transgenes for a transactivator fusion protein and/or an inhibitor fusion protein to create progeny that carry both a tetracycline-regulated fusion protein(s) gene and a tet-regulated target sequence. Expression of the gene of interest in these progeny can be modulated using tetracycline (or analogue). For example, expression of the gene of interest can be downmodulated using a transcriptional inhibitor fusion protein to examine the relationship between gene expression and the disease. Such an approach may be advantageous over gene "knock out" by homologous recombination to create animal models of disease, since the tet-regulated system described herein allows for control over both the levels of expression of the gene of interest and the timing of when gene expression is down- or up-regulated.

E. Production of Stable Cell Lines for Gene Cloning and Other Uses

The transcriptional activator proteins described herein can be used to regulate gene expression, and thereby allow production of stable cell lines that otherwise may not be produced. For example, stable cell lines carrying genes that are cytotoxic to the cells can be difficult or impossible to create due to "leakiness" in the expression of the toxic genes. By tightly regulating gene expression of such toxic genes using the transcriptional activator fusion proteins of the invention, stable cell lines carrying toxic genes may be created. Such stable cell lines can then be used to clone such toxic genes (e.g., inducing the expression of the toxic genes under controlled conditions using Tc or analog). General methods for expression cloning of genes, to which the transcriptional inhibitor system of the invention can be applied, are known in the art (see e.g., Edwards, C. P. and Aruffo, A. (1993) *Curr. Opin. Biotech.* 4:558-563) Moreover, the transcriptional regulatory proteins can be applied to modulate the expression of genes in other cells to create stable cell lines, such as in embryonic stem (ES) cells. Residual expression of certain genes introduced into ES cells may result in an inability to isolate stably transfected clones. Regulation of transcription of such genes using the transcriptional activator proteins described herein may be useful in overcoming this problem.

Exemplification

The following examples are provided to further illustrate various aspects of the present invention. They are not to be construed as limiting the invention.

The screen described in the following examples is based on the tTA/rtTA dependent expression of green fluorescent protein (GFP) from aequorae victoria (Niedenthal et al., 1996; Wach et al., 1998; Oldenburg et al., 1997, as optimized for enhanced fluorescence). The GFP protein was optimized for enhanced fluorescence by inserting the following mutations: F99S, M153T, and V163A (according to Crameri et al. (1996), *Nature Biotechnology* 14, 315-319); F64L and S65T (according to Cormack et al. (1996), *Gene* 173, 33-38); and Q80R and the insertion of an alanine at position 2; yielding GFP+. The fluorescence of GFP expressing yeast colonies is conveniently detected on suitable agar plates under UV light and can be quantified by FACS or fluorescence spectroscopy (Niedenthal et al., 1996).

Thus, a plasmid, designated pCM190GFP+, was constructed which contains the following elements:
- the coding sequence for GFP controlled by a tTA/rtTA responsive promoter;
- a tTA/rtTA encoding sequence that is constitutively expressed;
- the URA3 marker that allows selection in appropriate yeast strains;
- the replication function of the 2μ episome of S. cerevisiae.

Unique endonuclease cleavage sites allow for the removal of the TetR, the activation domain, or the entire tTA encoding sequences, typically replaced by pools of mutagenized alleles obtained as described previously (Leung et al., 1989).

The plasmid mixture was transformed to S. cerevisiae and transformants were selected via uracil prototrophy. The resulting transformants were screened on agar plates that allow examination for a variety of properties:
- induction of GFP by Tc derivatives or other chemicals;
- new alleles of rtTA with reduced basal expression in the absence of the inducer;
- increased expression levels in the presence of inducers.

If the sequence encoding the activating domain is replaced by appropriate sequence libraries, the screen can identify new activator or silencer domains that function optimally in fusions with TetR variants.

EXAMPLE 1 rtTA Variants with Improved Properties

The gene encoding GFP was cloned into the multiple cloning site of pCM190 (Gari et al., 1997) to serve as an indicator of rtTA activity, yielding plasmid pCM190GFP+. The TetR portion of tTA was amplified for mutagenesis with two oligonucleotide primers, 5'-GACCGATCCAGCCTCCGCGG (SEQ ID NO:46), and 5'-CGTGTGTCCCGCGGGGAGAA (SEQ ID NO:47), from the vector pCM190 as described (Leung et al., 1989). The PCR-fragments and pCM190-GFP+ were restricted with XbaII and BsiWI and purified. The PCR-fragments and the vector were then ligated and transformed into E. coli DH5α. Several thousand E. coli clones were co-cultured, and their plasmid pools were prepared and transformed into S. cerevisiae using the LiAc-method (Ito et al., 1983). The RS453 strain of S. cerevisiae (MATa; ade2-1; trp1-1; can1-100; leu2-3,112; his3-1;ura3-52) was used for the screening protocol.

Transformation of the plasmid into yeast allows one to score differences in GFP activity over a wide range of intensities by direct examination of colonies placed in UV light. In this way, large populations of yeast cells can be screened for promising tTA/rtTA candidates. Differences in the fluorescence of GFP originate from different expression levels of the indicator protein. This will, in general, reflect differences in the activation potential of the transactivators. After the usual screen, biochemical analysis can be performed with only a small number of positive candidates.

Figure 2:
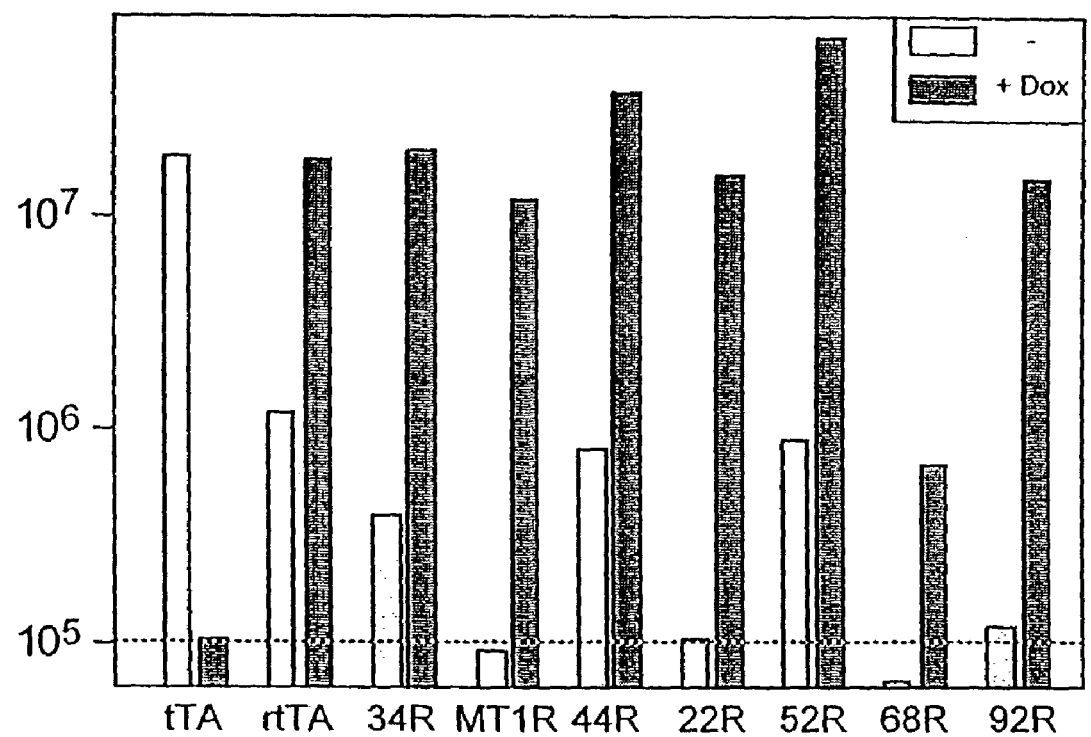
FIG. 2 is a graph depicting the rtTA dependent GFP fluorescence in *S. cerevisiae* in dependence of doxycycline (Dox).

Accordingly, the resulting uracil-prototroph yeast clones were replica plated on minimal medium without uracil containing either Tc and/or Dox and scored after growth for two to three days at 30° C. using long wavelength UV-light to excite GFP fluorescence. This led to the identification of several new rtTA-alleles: 34R, 44R, MT1R, 22R, 52R, 68R and 92R. The phenotype of the rtTA-34R and rtTA-44R alleles in yeast stimulated with Tc and Dox are shown in FIG. 1. The phenotype of the 34R, 44R, MT1R, 22R, 52R, 68R and 92R alleles in yeast stimulated with Dox are shown in FIG. 2. The GFP fluorescence is shown on a logarithmic scale on the left axis. Fluorescence intensities are shown for each transactivator in the absence of inducer, in the presence of 10 μg/ml of Tc, and/or in the presence of 10 μg/ml of Dox. The activities achieved with tTA and rtTA are shown for comparison.

S. cerevisiae strains containing rtTA-34R, rtTA-44R and a GFP$^{31}$ strain, as well as strains containing the original tTA and rtTA were grown overnight in minimal medium. Equivalents containing 1 OD600 of the cells were harvested, washed with PBS, and suspended in 2 ml of PBS. The light emission of these cells was scored in a fluorimeter using an excitation wavelength of 490 nm and recording emission at 512 nm. The basal activities of rtTA-34R and rtTA-44R were clearly lower as compared to rtTA. As shown in FIG. 1, activation of expression was at least in one case slightly higher than that achieved with the original rtTA or tTA, respectively. The induction factors varied between 100 and 300-fold. Thus, the new rtTA alleles are much better suited for regulation of gene expression in yeast than the original rtTA, which leads to only 40-fold induction of expression.

The advantage of the new rtTA's are low basal activities in the uninduced state combined with high levels of induction upon addition of Tc or Dox. This is achieved in absence of any repressor and thus permits regulation of gene expression over a broad range even in S. cerevisiae.

Following isolation of the respective plasmids from S. cerevisiae, the mutagenized rtTA regions were sequenced. The genotype of the novel rtTA alleles is shown in Table 1 below. The reference sequence of the parent rtTA is shown in FIG. 8, SEQ ID NO: 22.

TABLE 1

| | Novel rtTA mutants | | | | | |
|---|---|---|---|---|---|---|
| Designation of rtTA sequence variant | $1^{st}$ aa exchange/ new codon | $2^{nd}$ aa exchange/ new codon | $3^{rd}$ aa exchange/ new codon | $4^{th}$ aa exchange/ new codon | $5^{th}$ aa exchange/ new codon | $6^{th}$ aa exchange/ new codon |
| rtTA-34R0 nt = SEQ ID NO:1 aa = SEQ ID NO:2 | E19G ggg | A56P ccc | H139H cac | D148E gaa | H179R cgc | |
| rtTA-1956R nt = SEQ ID NO:6 aa = SEQ ID NO:7 | E19G ggg | A56P ccc | | | | |
| rtTA-MT1R nt = SEQ ID NO:8 | S12G ggc | E19G ggg | A56P ccc | | | |

TABLE 1-continued

Figure 3:
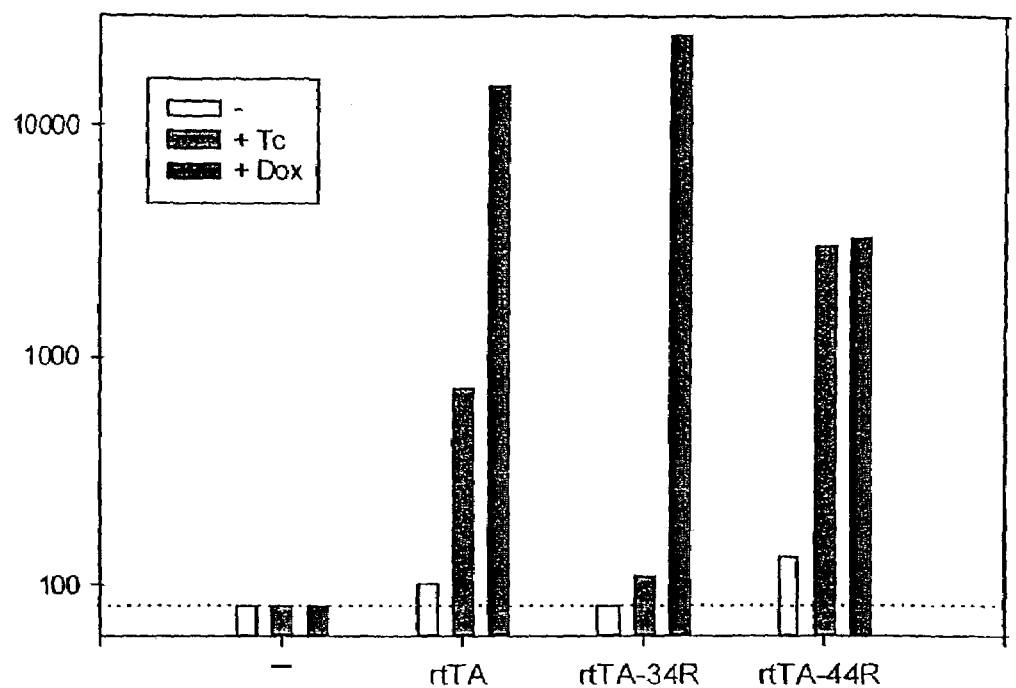
FIG. 3 is a graph depicting the rtTA-dependent luciferase expression in HeLa cells in dependence of Tc and/or Dox.
Figure 6:
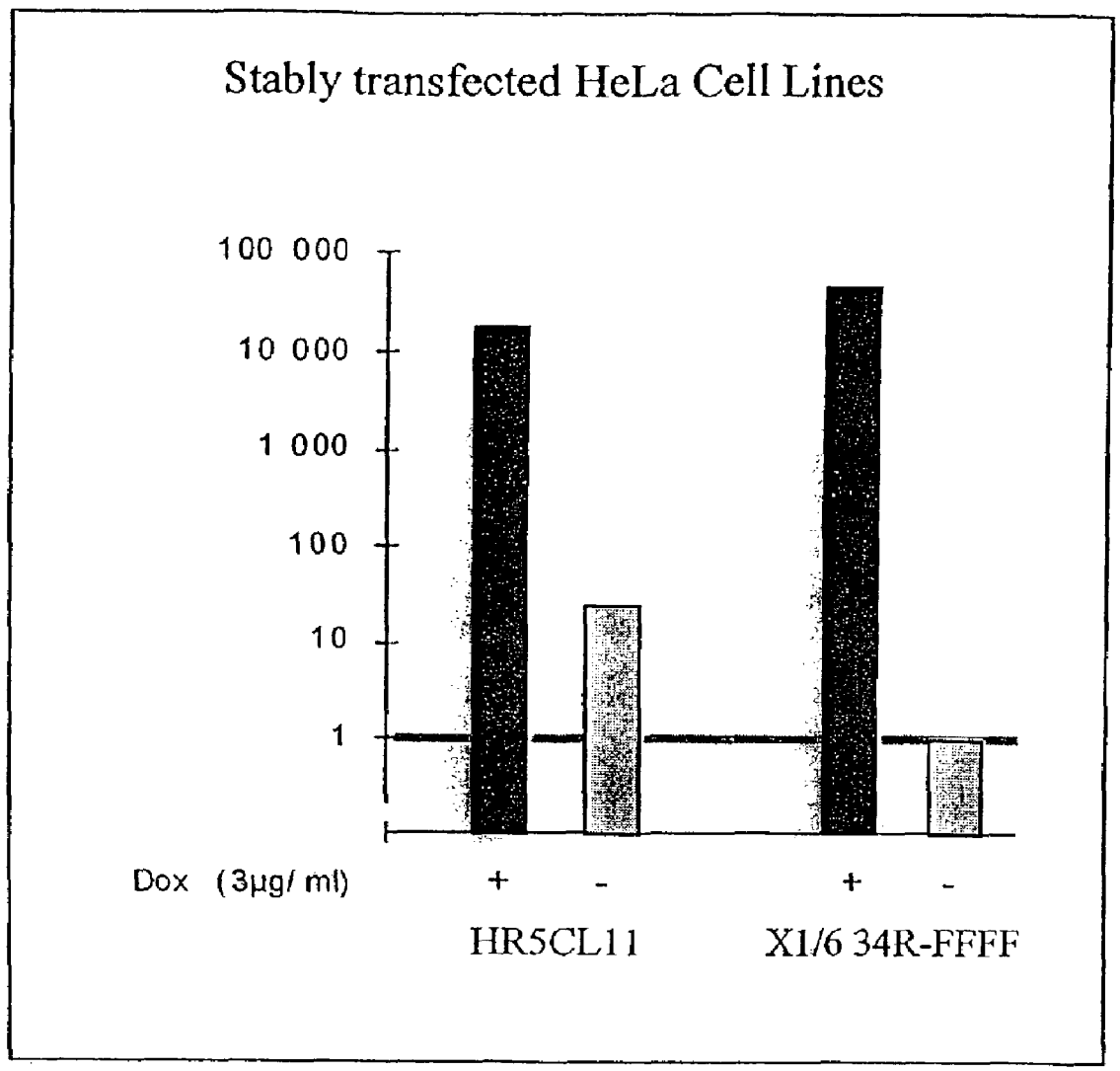
FIG. 6 is a graph depicting the doxycycline-dependent regulation of luciferase by rtTA and rtTA-34R-FFFF in stably transfected HeLa cells.

| | Novel rtTA mutants | | | | | |
|---|---|---|---|---|---|---|
| Designation of rtTA sequence variant | 1st aa exchange/ new codon | 2nd aa exchange/ new codon | 3rd aa exchange/ new codon | 4th aa exchange/ new codon | 5th aa exchange/ new codon | 6th aa exchange/ new codon |
| aa = SEQ ID NO:9 | | | | | | |
| rtTA-MT1/34R | S12G | E19G | A56P | H139H | D148E | H179R |
| nt = SEQ ID NO:10 | ggc | ggg | ccc | cac | gaa | cgc |
| aa = SEQ ID NO:11 | | | | | | |
| rtTA-44R | T26A | D95G | | | | |
| nt = SEQ ID NO:12 | gca | ggt | | | | |
| aa = SEQ ID NO:13 | | | | | | |
| rtTA-22R | G96R | | | | | |
| nt = SEQ ID NO:14 | aga | | | | | |
| aa = SEQ ID NO:15 | | | | | | |
| rtTA-52R | V99E | | | | | |
| nt = SEQ ID NO:16 | gaa | | | | | |
| aa = SEQ ID NO:17 | | | | | | |
| rtTA-68R | E19G | R87S | □C88 | | | |
| nt = SEQ ID NO:18 | ggg | agt | — | | | |
| aa = SEQ ID NO:19 | | | | | | |
| rtTA-92R | V99E | E204K | | | | |
| nt = SEQ ID NO:20 | gaa | aaa | | | | |
| aa = SEQ ID NO:21 | | | | | | | rtTA-34R and rtTA-44R were then recloned into pUHD15-1 (Gossen & Bujard, 1992), replacing the respective portions of tTA. HeLa cells were transiently cotransfected with plasmids pUHC13-3, encoding the luciferase gene controlled by $P_{tet}$ (Gossen & Bujard, 1992), and the pUHD15-1 plasmids containing the genes of the respective transactivators. Luciferase activities were measured in absence (light column) and presence of 5 µg/ml of the effectors tetracycline (Tc, light grey) or doxycycline (Dox, dark grey). On the X axis, (−) corresponds to control HeLa cells into which no DNA was transferred. The results shown in FIG. 3 indicate that rtTA-34R may lead to an even higher induction of luciferase activity as compared to rtTA. The increased regulation factor observed results from both a lower basal and a higher induced activity. Thus, rtTA-34R isolated exhibits an improved reverse phenotype in HeLa cells as well as in S. cerevisiae (FIGS. 3 and 6). As in S. cerevisiae, the mutant rtTA-44R also shows a reverse phenotype in HeLa cells. However, when compared with rtTA, the induction level is not improved over rtTA.

Thus, the described screening procedure for new rtTA alleles identifies mutants which show induction of transcription after Dox addition in HeLa cells. Furthermore, the phenotypes observed in HeLa cells for most mutants reflect faithfully the properties seen in yeast. This demonstrates that the screening procedure in S. cerevisiae is a valuable tool for discovering TetR-based regulatory proteins with novel activities in mammalian cells.

EXAMPLE 2

Selection of tTA Mutants with Differential Induction by Tetracycline Analogues

In order to identify tTA mutations with different sensitivities towards tetracycline analogues, mutagenesis of the TetR portion of tTA, transformation and selection in yeast were performed as outlined above. For further analysis, the resulting candidates were transformed into yeast and spread on minimal medium plates in the absence of uracil, which contained either 10 µg/ml tetracycline, anhydrotetracycline, oxytetracycline, chloro-tetracycline or doxycycline. The yeast were grown for two to three days at 30° C. and their GFP expression phenotype was examined as described above. This led to the identification of several new tTA-alleles: 2, 11, 19, 22, 23, 24, 31, 36, 38, 45, and 50; the genotype of the novel tTA alleles is shown in Table 2 below. The reference sequence of the parent tTA is shown in FIG. 9.

TABLE 2

| | Novel tTA mutants | | | | | |
|---|---|---|---|---|---|---|
| Designation of tTA sequence variant | 1st aa exchange/ new codon | 2nd aa exchange/ new codon | 3rd aa exchange/ new codon | 4th aa exchange/ new codon | 5th aa exchange/ new codon | 6th aa exchange/ new codon |
| tTA-2 | P167S | | | | | |
| nt = SEQ ID NO:26 | tcg | | | | | |
| aa = SEQ ID NO:27 | | | | | | |
| tTA-11 | I164L | | | | | |
| nt = SEQ ID NO:28 | ctt | | | | | |
| aa = SEQ ID NO:29 | | | | | | |
| tTA-19 | F78S | | | | | |
| nt = SEQ ID NO:30 | tct | | | | | |
| aa = SEQ ID NO:31 | | | | | | |
| TTA-22 | Y132C | | | | | |

TABLE 2-continued

| Designation of tTA sequence variant | Novel tTA mutants | | | | | |
|---|---|---|---|---|---|---|
| | 1st aa exchange/ new codon | 2nd aa exchange/ new codon | 3rd aa exchange/ new codon | 4th aa exchange/ new codon | 5th aa exchange/ new codon | 6th aa exchange/ new codon |
| nt = SEQ ID NO:32 | tgt | | | | | |
| aa = SEQ ID NO:33 | | | | | | |
| TTA-23 | Y110C | I174V | | | | |
| nt = SEQ ID NO:34 | tgt | gtc | | | | |
| aa = SEQ ID NO:35 | | | | | | |
| TTA-24 | I174T | E183K | | | | |
| nt = SEQ ID NO:36 | acc | aag | | | | |
| aa = SEQ ID NO:37 | | | | | | |
| TTA-31 | L113H | | | | | |
| nt = SEQ ID NO:38 | cac | | | | | |
| aa = SEQ ID NO:39 | | | | | | |
| TTA-36 | S85G | I174V | | | | |
| nt = SEQ ID NO:40 | ggt | gtc | | | | |
| aa = SEQ ID NO:41 | | | | | | |
| TTA-38 | S85R | | | | | |
| nt = SEQ ID NO:42 | aga | | | | | |
| aa = SEQ ID NO:43 | | | | | | |
| TTA-45 | D77D | L170V | L187L | | | |
| nt = SEQ ID NO:3 | gac | gta | ttg | | | |
| aa = SEQ ID NO:4 | | | | | | |
| TTA-50 | A56V | | | | | |
| nt = SEQ ID NO:44 | gtc | | | | | |
| aa = SEQ ID NO:45 | | | | | | |

One mutant that was isolated from this screen, tTA-45, was sequenced and found to carry an amino acid exchange at position 170 from a leucine to a valine (L170V). The induction efficiency of tTA-45 in response to varying concentrations of Tc or Dox was determined in transient transfection assays in HeLa cells. The inducer concentration leading to 50% repression of the luciferase activity ($IC_{50}$) was determined and is described in Table 3 below.

TABLE 3

Effects of Tc and Dox on induction properties of tTA and tTA-45

| | $IC_{50}$ (ng inducer/ml) | |
|---|---|---|
| Inducer | tTA (Wildtype) | tTA-45 (L170V) |
| Tc | 3 | 270 |
| Dox | 0.6 | 5 |

The mutant tTA-45 is 100-fold less sensitive to Tc, but only about 10-fold less sensitive to Dox.

Therefore, we conclude that the *S. cerevisiae* based screen for Tc dependent eukaryotic transcriptional activators is also suitable for the identification of tTAs with altered inducer recognition properties. This is important for practical applications because this screen can be used to change the induction profiles of Tc dependent transcription factors, thus enabling the construction of novel alleles which respond differentially to chemically distinct inducers. These Tc dependent transcription factors may then be used to construct mammalian cell lines or transgenic animals in which a number of different genes can be differentially regulated by various combinations of Tc analogues.

Figure 4:
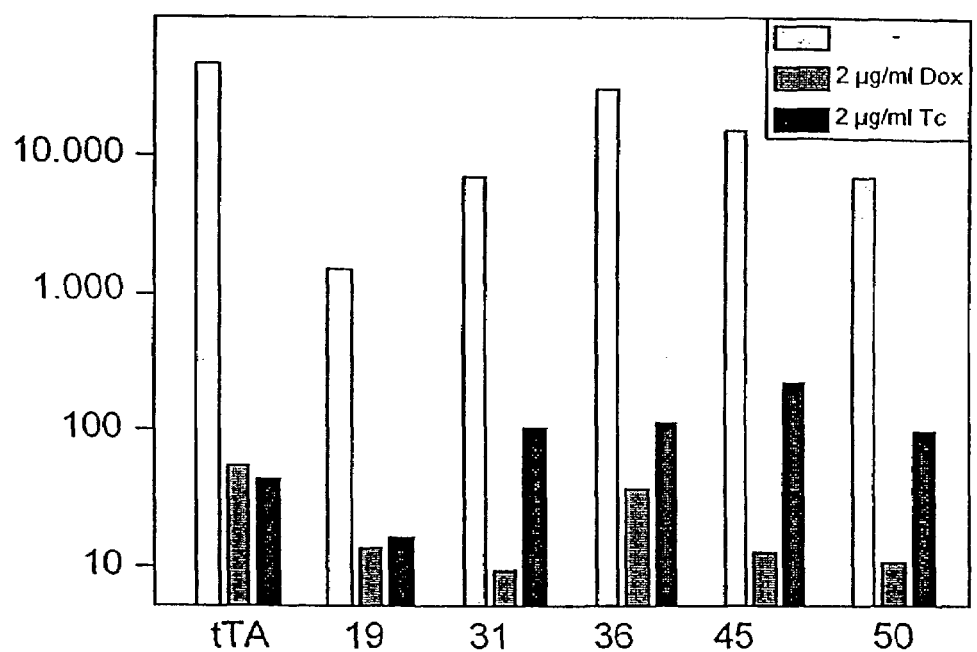
FIG. 4 is a graph depicting the tTA dependent luciferase expression in transiently transfected human epithelial cells in dependence of Tc and/or Dox.

Analysis of five novel tTA alleles, tTA-19, tTA-31, tTA-36, tTA-45 and tTA-50, was performed by transient transfection into human epithelial cells. Luciferase activities were measured in absence (light column) and presence of 2 μg/ml of the effectors doxycycline (Dox, light grey) or tetracycline (Tc, dark grey), as shown in FIG. 4. On the X axis, (−) corresponds to control human epithelial cells into which no DNA was transferred.

EXAMPLE 3

A Novel TetR-Based Transactivator: rtTA-34R

The new allele encoding the reverse Dox-inducible transactivator rtTA-34R was sequenced and found to contain different mutations than the previously characterized rtTA. This demonstrates that a reverse transactivator phenotype can be obtained by mutations in different regions of TetR. The mutations found in rtTA-34R are: E19G, A56P, H139H (silent), A148E, and H179R. The amino acids at positions 95, 101, and 102, which are mutated in the original rtTA are the wild type residues in rtTA-34R.

Figure 5:
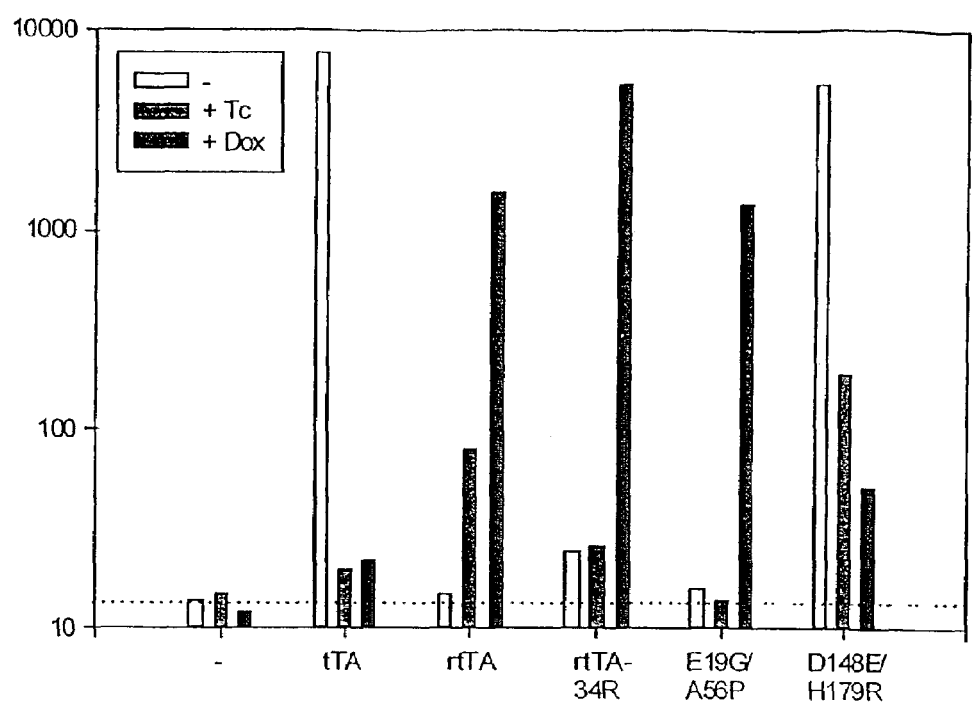
FIG. 5 is a graph depicting the contribution of various mutations in rtTA-34R to the reverse phenotype.

To obtain additional information about the role of the mutated residues, we separated the mutations at positions 19 and 56 from those at 139, 148 and 179. The resulting proteins are called rtTA-1956R and rtTA-148179R. The activation potential of rtTA-1956R and rtTA-148179R was assessed in transient expression experiments. Plasmids encoding the respective rtTA variants were cotransfected with the pUHC13-3 luciferase indicator plasmid into HeLa cells and the luciferase activity was determined. The results shown in FIG. 5 indicate that two exchanges, E19G and A56P, are sufficient for the reverse phenotype. The mutations in positions 148 and 179 are merely slightly supportive for the phenotype as they do not yield a reverse phenotype by themselves.

EXAMPLE 4

HeLa Cell Lines Producing rtTA-34R from Episomally Stabilized Plasmids

In order to generate cell lines that maintain the plasmid episomally and thus produce the transactivator over extended periods of time, the transcription unit containing the rtTA-34R coding sequence controlled by the hCMV promoter was inserted into pREP9 (Invitrogen, Carlsbad, USA) from which the RSV promoter had been excised. This resulted in the Epstein Barr-based vector pCEP4-rtTA-34R. HeLa cells were transfected with the plasmid pCEP4-rtTA-34R, and clones isolated via G418 selection. Clones stably producing the transactivator were selected and tested for their ability to activate transcription from the transiently transfected luciferase reporter construct pUHC13-3 in the presence and absence of Dox.

The data shown in Table 4 indicates that three HeLa cell lines derived from various clones (0.34R-16,-33 and -36) exhibit similar background activity slightly higher than the parent cell line. Upon addition of 5 µg/ml of Dox, luciferase activity is induced up to 600 fold. In comparison to the HeLa cell line HR5 harboring chromosomal copies of the rtTA gene (Gossen et al., 1995), the background level is reduced. In addition, the induced level of luciferase is significantly elevated. This leads to a several hundred fold induction of gene expression in the case of the rtTA-34R clones whereas in HR5 cells rtTA achieves only a 20 to 30 fold induction under these conditions.

TABLE 4

Doxycycline-dependent regulation of luciferase in HeLa cells producing rtTA-34R from episomally stabilized plasmids.

| Cell line | Luciferase activity (RLU/µg protein) | | factor of induction |
|---|---|---|---|
| | with Dox | without Dox | |
| HeLa | 430 ± 110 | 324 ± 20 | 1 |
| HeLa HR5 (Tet on) | 920 ± 170 | 26400 ± 4030 | 27 |
| HeLa 0.34R-16 | 540 ± 50 | 323600 ± 69470 | 600 |
| HeLa 0.34R-33 | 360 ± 140 | 74620 ± 3230 | 200 |
| HeLa 0.34R-36 | 430 ± 50 | 87000 ± 7820 | 200 |

EXAMPLE 5

Gene Encoding rTetR-34R Allele Fused to Minimal Activation Domains

The coding sequence of rTetR-34R was fused with a DNA encoding four minimal activation domains (FFFF)(Baron et al., 1997) by insertion into a proper pUHD vector to generate plasmid pUHrT61-1. HeLa cell line X1/6 was transfected with plasmid pUHrT5 1-1 carrying the rtTA-34R-FFFF gene under the control of $P_{hCMV}$. The resulting HeLa cell line X1/6-34R-FFFF contains, in addition, the $P_{tet}$-luciferase expression unit in a "silent but activatable" locus.

Cell lines derived from various clones that contain pUHrT51-1 stably inserted into the genome where it is constitutively expressed were isolated via hygromycin-B selection and analyzed for Dox dependent luciferase activity. As shown in FIG. 6, in the absence of Dox there was no detectable luciferase activity, whereas upon addition of Dox, luciferase activity was induced up to 50 000 fold. In contrast, in our previously described HR5-CL11 cell line (Gossen et al., 1995), a significant background luciferase activity is observed in the absence of Dox and induction by Dox reaches only about 700 fold. This is most likely due to the residual affinity between rtTA and tetO.

EXAMPLE 6

A Synthetic Gene Encoding TetR-34R Fused to Minimal Activation Domains (rtTA2-34R$^S$)

To further improve rtTA-34R (SEQ ID NO:2), the DNA sequence encoding the first 206 amino acids of the rtTA-34R transactivator was fused to 3 minimal activation domains (FFF) of the VP-16 activation domain, and was converted into a polynucleotide that encodes the transactivator in codon frequencies as found in humans. This rtTA2-34R$^S$ sequence (SEQ ID NO: 5) was optimized with respect to a variety of additional parameters as described previously (Pan et al., 1999). Thus, it contains neither splice donor nor splice acceptor sites. Other features that might limit its expression have been eliminated as well. It is anticipated that with this synthetic gene, rtTA2-34R$^S$ can be stably produced in a variety of eukaryotic cells that are presently not amenable to rtTA-mediated gene regulation. This is currently being examined through the generation of several transgenic mouse lines that are expected to produce rtTA2-34R$^S$ in hepatocytes and in mature B-cells.

The synthetic gene encoding rtTA2-34R$^S$ was cloned into pUHD15-1 and expression was examined in HeLa cells. In transient transfection experiments using luciferase activity in relative light units as a functional readout, induction of up to 20 fold was observed in cells treated with Dox, as shown in Table 5, Experiment A. Results with cells transfected with rtTA2 are shown in Experiment B.

TABLE 5

Doxycycline-dependent regulation of luciferase in HeLa cells producing rtTA2-34R$^s$

| | Experiment A | Experiment B |
|---|---|---|
| − Dox | 1 | 1 |
| + Dox | 20.325 | 7.279 |

Figure 7:
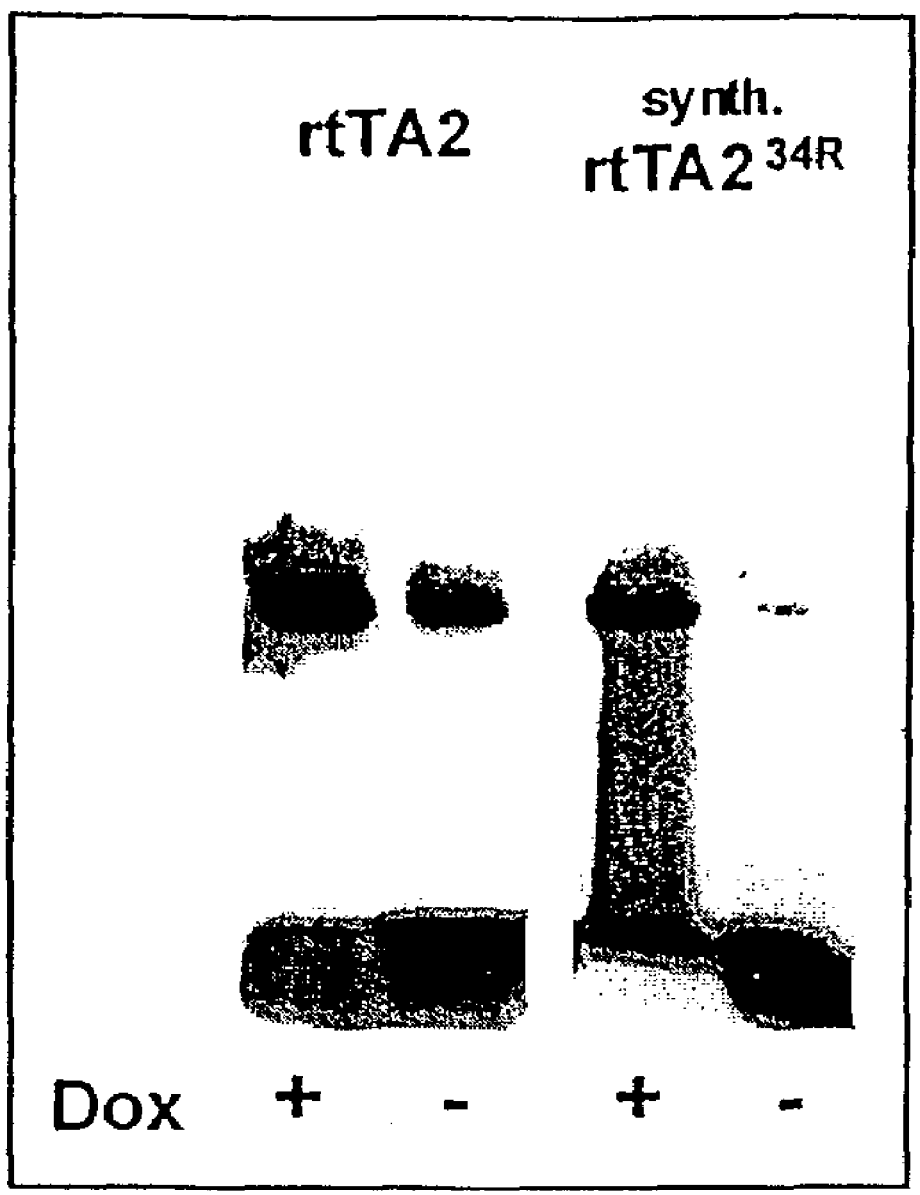
FIG. 7 is a gel depicting the mobility change of tet operator DNA in presence of rtTA2 and rtTA2-34R.

Cellular material from cells transfected as described above was also used to compare the binding of rtTA2-34R and rtTA2 (rtTA fused to 3 minimal activation domains) to operator DNA in DNA retardation experiments.

rtTA2 and rtTA2-34R$^S$ were produced in HeLa cells and exposed to radioactively labeled tetO DNA in presence (+) and absence (−) of Dox. Electrophoretic migration of the complexes reveals the differential affinities between tetO and the two transactivators. As indicated in FIG. 7, the residual binding (i.e., binding in the absence of Dox) of rtTA2-34R$^S$ to operator DNA is greatly reduced.

Therefore, the new reverse transactivator is a decisive improvement when compared to the previously characterized rtTA. Since there is little reason to assume that the screening performed for this result was saturating, we anticipate that other rtTA's with still improved properties may be obtained.

REFERENCES

Baron, U., Gossen, M. & Bujard, H. (1997) Tetracycline controlled transcription in eukaryotes: novel transactivators with graded transactivation potential. Nucl. Acids Res. 25, 2723-2729.

Baron, U., Schnappinger, D., Helbl, V., Gossen, M., Hillen, W. & Bujard, H. (1999) Generation of conditional mutants in higher eukaryotes by switching between the expression of two genes. Proc. Natl. Acad. Sci. USA 96, 1013-1018.

Belli, G., Gari, E., Piedrafita, L., Aldea, M., & Herrero, E. (1998). An activator/repressor dual system allows tight tetracycline-regulated gene expression in budding yeast. Nucleic Acids Res. 26, 942-947.

Bello, B., Resendez-Perez, D., & Gehring, W. J. (1998). Spatial and temporal targeting of gene expression in *Drosophila* by means of a tetracycline-dependent transactivator system. Development 125, 2193-2202.

Bieschke, E. T., Wheeler, J. C., & Tower, J. (1998). Doxycycline-induced transgene expression during *Drosophila* development and aging. Mol. Gen. Genet. 258, 571-579.

Camacho-Vanegas, O., Mannucci, L. & Amaldi, F. (1998) Construction of *Xenopus* (B3.2) and human (HeLa) cell lines expressing the tetracycline-controlled transactivator (tTA). In Vitro Cell Dev. Biol. Anim. 34, 14-15.

Cohlan, S. Q. (1977). Tetracycline staining of teeth. Teratology 15, 127-129.

Efrat, S., Fusco-DeMane, D., Lemberg, H., Emran, O. A. & Wang, X. (1995) Conditional transformation of a pancreatic β-cell line derived from transgenic mice expressing a tetracycline regulated oncogene. Proc. Natl. Acad. Sci. USA 92, 3576-3580.

Ewald, D., Li, M., Efrat, S., Auer, G., Wall, R. J., Furth, P. A. & Hennighausen, L. (1996) Time-sensitive reversal of hyperplasia in transgenic mice expressing SV40 T antigen. Science 273, 1384-1386.

Fishman, G. I., Kaplan, M. L. & Buttrick, P. M. (1994) Tetracycline-regulated cardiac gene expression in vivo. J. Clin. Invest. 93, 1864-1868.

Früh, K., Gossen, M., Wang, K., Bujard, H., Peterson, P. A., & Yang, Y. (1994). Displacement of housekeeping proteasome subunits by MHC-encoded LMPs: a newly discovered mechanism for modulating the multicatalytic proteinase complex. EMBO J. 13, 3236-3244.

Furth, P. A., Onge, L. S., Böger, H., Gruss, P., Gossen, M., Kistner, A., Bujard, H., & Henninghausen, L. (1994). Temporal control of gene expression in transgenic mice by a tetracycline-responsive promoter. Proc. Natl. Acad. Sci. USA 91, 9302-9306.

Gari, E., Piedrafita, L., Aldea, M., & Herrero, E. (1997). A set of vectors with a tetracycline-regulatable promoter system for modulated gene expression in *Saccharomyces cerevisiae*. Yeast 13, 837-848.

Gatz, C., & Quail, P. H. (1988). Tn10-encoded Tet repressor can regulate an operator-containing plant promoter. Proc. Natl. Acad. Sci. USA 85, 1394-1937.

Gossen, M., & Bujard, H. (1992). Tight control of gene expression in mammalian cells by tetracycline-responsive promoters. Proc. Natl. Acad. Sci. USA 89, 5547-5551.

Gossen, M., Freundlieb, S., Bender, G., Müller, G., Hillen, W., & Bujard, H. (1995). Transcriptional activation by tetracyclines in mammalian cells. Science 268, 1766-1769.

Harding, T. C., Geddes, B. J., Murphy, D., Knight, D. & Uney, J. B. (1998) Switching transgene expression in the brain using an adenoviral tetracycline-regulatable system. Nat. Biotechnol. 16, 553-555.

Helbl, V., & Hillen, W. (1998). Stepwise selection of TetR variants recognizing tet operator 4C with high affinity and specificity. J. Mol. Biol. 276, 313-318.

Helbl, V., Tiebel, B., & Hillen, W. (1998). Stepwise selection of TetR variants recognizing tet operator 6C with high affinity and specificity. J. Mol. Biol. 276, 319-324.

Hillen, W., & Berens, C. (1994). Mechanisms underlying expression of tn10 encoded tetracycline resistance. Annu. Rev. Microbiol. 48, 345-369.

Hinrichs, W., Kisker, C., Düvel, M., Müller, A., Tovar, K., Hillen, W., & Saenger, W. (1994). Structure of the Tet repressor-tetracycline complex and regulation of antibiotic resistance. Science 264, 418-420.

Ito, H., Fukuda, Y., Murata, K., & Kimura, A. (1983). Transformation of intact yeast cells treated with alkali cations. J. Bact. 153, 163-168.

Kisker, C., Hinrichs, W., Tovar, K., Hillen, W., & Saenger, W. (1995). The complex formed between tet repressor and tetracycline-$Mg^{2+}$ reveals mechanism of antibiotic resistance. J. Mol. Biol. 247, 260-280.

Kistner, A., Gossen, M., Zimmermann, F., Jerecic, J., Ullmer, C., Lübbert, H., & Bujard, H. (1996). Doxycycline-mediated quantitative and tissue-specific control of gene expression in transgenic mice. Proc. Natl. Acad. Sci. USA 93, 10933-10938.

Leung, D. W., Chen, E., & Goeddel, D. V. (1989). A method for random mutagenesis of a defined DNA segment using a modified polymerase chain reaction. Technique 1, 11-15.

Müller, G., Hecht, B., Helbl, V., Hinrichs, W., Saenger, W., & Hillen, W. (1995). Characterization of non-inducible Tet repressor mutants suggests conformational changes necessary for induction. Nature Struct. Biol. 2, 693-703.

Niedenthal, R. K., Riles, L., Johnston, M., & Hegemann, J. H. (1996). Green fluorescent protein as a marker for gene expression and subcellular localization in budding yeast. Yeast 12, 773-786.

Oldenburg, K. R., Vo, K. T., Michaelis, S., & Paddon, C. (1997). Recombination-mediated PCR-directed plasmid construction in vivo in yeast. Nucl. Acids Res. 25, 2.

Orth, P., Cordes, F., Schnappinger, D., Hillen, W., Saenger, W., & Hinrichs, W. (1998). Conformational changes of the Tet repressor induced by tetracycline trapping. J. Mol. Biol. 279, 439-447.

Pan, W., Ravot, E., Tolle, R., Frank, R., Mosbach, R., Türbachova, I. & Bujard, H. (1999) Vaccine candidate MSP-1 from *Plasmodium falciparum*: a redesigned 4917 bp polynucleotide enables synthesis and isolation of full length protein from *E. coli* and mammalian cells. Nucl. Acids Res. 27, 1094-1103.

Paulus, W., Baur, I., Oberer, D. M., Breakefield, X. O., & Reeves, S. A. (1997). Regulated expression of the diphtheria toxin A gene in human glioma cells using prokaryotic transcriptional control elements. J. Neurosurg. 87, 89-95.

Schnappinger, D., Schubert, P., Pfleiderer, K., & Hillen, W. (1998). Determinants of protein-protein recognition by four helix bundles: changing the dimerization specificity of Tet repressor. EMBO J. 17, 535-543.

Shockett, P., Difilippantonio, M., Hellman, N., & Schatz, D. G. (1995). A modified tetracycline-regulated system provides autoregulatory, inducible gene expression in cultured cells and transgenic mice. Proc. Natl. Acad. Sci. USA 92, 6522-6526.

Wach, A., Brachat, A., Alberti-Segui, C., Rebischung, C., & Philippsen, P. (1997). Heterologous HIS3 marker and GFP reporter modules for PCR-targeting in *Saccharomyces cerevisiae*. Yeast 13, 1065-1075.

Weinmann, P., Gossen, M., Hillen, W., Bujard, H. & Gatz, C. (1994) A chimeric transactivator allows tetracycline-responsive gene expression in whole plants. Plant J. 5, 559-569.

Zeidler, M., Gatz, C., Hartmann, E. & Hughes, J. (1996) Tetracycline-regulated reporter gene expression in the moss *Physcomitrella patens*. Plant Mol. Biol. 30, 199-205.

Zhou, Y., Zhang, X., & Ebright, R. H. (1991). Random mutagenesis of gene-sized DNA molecules by use of PCR with Taq DNA polymerase. Nucl. Acids Res. 19, 6052.

Gallego, C., Gari, E., Colomina, N., Herrero E. and Aldea, M. (1997) The Cln3 cyclin is down-regulated by translational repression and degradation during the G1 arrest caused by nitrogen deprivation in budding yeast. EMBO Journal 16, 7196-7206.

Gan, E., Piedrafita, L., Aldea, M. and Herrero, E. (1997) A set of vectors with a tetracycline-regulatable promoter system for modulated gene expression in Saccharomyces cerevisiae. Yeast 13, 837-848.

Belli, G., Gari, E., Aldea, M. and Herrero, E. (1998a) Functional analysis of yeast essential genes using a promoter-substitution cassette and the tetracycline-regulatable dual expression system. Yeast 14, 1127-1138.

Belli, G., Gari, E., Piedrafita, L., Aldea, M. and Herrero, E. (1998b) An activator/repressor dual system allows tight tetracycline-regulated gene expression in budding yeast. Nucl. Acids Res. 26, 942-947.

Nagahashi, S., Lussier, M. and Bussey, H. (1998) Isolation of Candida glabrata homologs of the Saccharomyces cerevisiae KRE9 and KNH1 genes and their involvement in cell wall beta-1, 6-glucan synthesis. J. Bacteriol. 180, 5020-5029.

Nakayama, H., Izuta, M., Nagahashi, S., Sihta, E. Y., Sato, Y. Yamazaki, T., Arisawa, M. and Kitada, K. (1998) A controllable gene expression system for the pathogenic fungus Candida glabrata. Microbiology 144, 2407-2415.

Colomina, N., Gari, E., Gallego, C., Herrero, E. and Aldea, M. (1999) G1 cyclins block the Ime1 pathway to make mitosis and meiosis incompatible in budding yeast. EMBO J. 18, 320-329.

Wissmann, A., Wray, L. V. Jr., Somaggio, U., Baumeister, R., Geissendoerfer, M. and Hillen, W. (1991) Selection for Tn10 Tet repressor binding to tet operator in Escherichia coli: Isolation of temperature sensitive mutants and combinatorial mutagenesis in the DNA binding motif. Genetics 128, 225-232.

INCORPORATION BY REFERENCE

All patents, published patent applications and other references disclosed herein are hereby expressly incorporated herein in their entireties by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated polynucleotide selected from the group consisting of:
   (a) a polynucleotide having the nucleic acid sequence as shown in SEQ ID No:5;
   (b) a polynucleotide encoding a first polypeptide, wherein the first polypeptide differs from the polypeptide encoded by SEQ ID NO: 5 by a single amino acid, wherein the amino acid difference is S12G;
   (c) a polynucleotide having a nucleic acid sequence which differs from the nucleic acid sequence of (a) due to the degeneracy of the genetic code;
   wherein the polypeptide encoded by each of the polynucleotides (a), (b), and (c) is capable of inducing transcriptional activity in the presence of tetracycline, tetracycline derivatives, or tetracycline analogs in a host cell.

2. The polynucleotide of claim 1, wherein the host cell is a mammalian cell.

3. The polynucleotide of claim 1, wherein the tetracycline analog is doxycycline.

4. The polynucleotide of claim 1, wherein the polypeptide encoded by the polynucleotide mediates an increased induced transcriptional activity in the presence of tetracycline, tetracycline derivatives, or tetracycline analogs or a decreased basal transcriptional activity in the absence of tetracycline, tetracycline derivatives, or tetracycline analogs compared to the rtTA polypeptide encoded by the nucleic acid sequence shown in FIG. 8, wherein the tetracycline repressor is fused to three minimal activation domains.

5. A vector comprising the polynucleotide of claim 1.

6. The vector of claim 5, wherein the vector is an expression vector.

7. The vector of claim 5, wherein the vector is selected from the group consisting of: pCM190GFP+, pUHD15-1, pREP9, pUHD, and baculovirus expression vectors.

8. An isolated host cell comprising the vector of claim 5.

9. The host cell of claim 8, wherein the host cell is selected from the group consisting of: a plant cell, an insect cell, a fungal cell, a bacterial cell or a mammalian cell.

10. A method for producing a protein encoded by the polynucleotide of claim 1 comprising:
   inserting the polynucleotide of claim 1 into an expression vector;
   transforming or transfecting an isolated host cell;
   incubating the host cell under conditions conducive for protein expression;
   producing the protein encoded by the polynucleotide of claim 1.

11. The method of claim 10, wherein the expression vector is selected from the group consisting of: pCM190GFP+, pUHD15-1, pREP9, pUHD, and baculovirus expression vectors.

12. The method of claim 10, wherein the isolated host cell is selected from the group consisting of: a plant cell, an insect cell, a fungal cell, a bacterial cell or a mammalian cell.

13. The method of claim 10, wherein the isolated host cell is a HeLa cell.

* * * * *

SEQUENCE LISTING

```
<160> NUMBER OF SEQ ID NOS: 47

<210> SEQ ID NO 1
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 1 atg tct aga tta gat aaa agt aaa gtg att aac agc gca tta gag ctg      48
Met Ser Arg Leu Asp Lys Ser Lys Val Ile Asn Ser Ala Leu Glu Leu
 1               5                  10                  15 ctt aat ggg gtc gga atc gaa ggt tta aca acc cgt aaa ctc gcc cag      96
Leu Asn Gly Val Gly Ile Glu Gly Leu Thr Thr Arg Lys Leu Ala Gln
             20                  25                  30 yaag cta ggt gta gag cag cct aca ttg tat tgg cat gta aaa aat aag    144
Lys Leu Gly Val Glu Gln Pro Thr Leu Tyr Trp His Val Lys Asn Lys
         35                  40                  45 ycgg gct ttg ctc gac gcc tta ccc att gag atg tta gat agg cac cat    192
Arg Ala Leu Leu Asp Ala Leu Pro Ile Glu Met Leu Asp Arg His His
     50                  55                  60 yact cac ttt tgc cct tta gaa ggg gaa agc tgg caa gat ttt tta cgt    240
Thr His Phe Cys Pro Leu Glu Gly Glu Ser Trp Gln Asp Phe Leu Arg
 65                  70                  75                  80 yaat aac gct aaa agt ttt aga tgt gct tta cta agt cat cgc gat gga    288
Asn Asn Ala Lys Ser Phe Arg Cys Ala Leu Leu Ser His Arg Asp Gly
                 85                  90                  95 ygca aaa gta cat tta ggt aca cgg cct aca gaa aaa cag tat gaa act    336
Ala Lys Val His Leu Gly Thr Arg Pro Thr Glu Lys Gln Tyr Glu Thr
            100                 105                 110 yctc gaa aat caa tta gcc ttt tta tgc caa caa ggt ttt tca cta gag    384
Leu Glu Asn Gln Leu Ala Phe Leu Cys Gln Gln Gly Phe Ser Leu Glu
```

```
yaat gca tta tat gca ctc agc gct gtg ggg cac ttt act tta ggt tgc        432
Asn Ala Leu Tyr Ala Leu Ser Ala Val Gly His Phe Thr Leu Gly Cys
    130                 135                 140 ygta ttg gaa gaa caa gag cat caa gtc gct aaa gaa gaa agg gaa aca        480
Val Leu Glu Glu Gln Glu His Gln Val Ala Lys Glu Glu Arg Glu Thr
145                 150                 155                 160 ycct act act gat agt atg ccg cca tta tta cga caa gct atc gaa tta        528
Pro Thr Thr Asp Ser Met Pro Pro Leu Leu Arg Gln Ala Ile Glu Leu
                165                 170                 175 yttt gat cgc caa ggt gca gag cca gcc ttc tta ttc ggc ctt gaa ttg        576
Phe Asp Arg Gln Gly Ala Glu Pro Ala Phe Leu Phe Gly Leu Glu Leu
            180                 185                 190 yatc ata tgc gga tta gaa aaa caa ctt aaa tgt gaa agt ggg tcc gcg        624
Ile Ile Cys Gly Leu Glu Lys Gln Leu Lys Cys Glu Ser Gly Ser Ala
        195                 200                 205 ytac agc cgc gcg cgt acg aaa aac aat tac ggg tct acc atc gag ggc        672
Tyr Ser Arg Ala Arg Thr Lys Asn Asn Tyr Gly Ser Thr Ile Glu Gly
    210                 215                 220 yctg ctc gat ctc ccg gac gac gac gcc ccc gaa gag gcg ggg ctg gcg        720
Leu Leu Asp Leu Pro Asp Asp Asp Ala Pro Glu Glu Ala Gly Leu Ala
225                 230                 235                 240 ygct ccg cgc ctg tcc ttt ctc ccc gcg gga cac acg cgc aga ctg tcg        768
Ala Pro Arg Leu Ser Phe Leu Pro Ala Gly His Thr Arg Arg Leu Ser
                245                 250                 255 yacg gcc ccc ccg acc gat gtc agc ctg ggg gac gag ctc cac tta gac        816
Thr Ala Pro Pro Thr Asp Val Ser Leu Gly Asp Glu Leu His Leu Asp
            260                 265                 270 yggc gag gac gtg gcg atg gcg cat gcc gac gcg cta gac gat ttc gat        864
Gly Glu Asp Val Ala Met Ala His Ala Asp Ala Leu Asp Asp Phe Asp
        275                 280                 285 yctg gac atg ttg ggg gac ggg gat tcc ccg ggt ccg gga ttt acc ccc        912
Leu Asp Met Leu Gly Asp Gly Asp Ser Pro Gly Pro Gly Phe Thr Pro
    290                 295                 300 ycac gac tcc gcc ccc tac ggc gct ctg gat atg gcc gac ttc gag ttt        960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag       1008
Glu Gln Met Phe Thr Asp Ala Leu Gly Ile Asp Glu Tyr Gly Gly
                325                 330                 335

<210> SEQ ID NO 2
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 2

Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Phe Cys Pro Leu Glu Gly Glu Ser Trp Gln Asp Phe Leu Arg
65                  70                  75                  80
```

```
Asn Asn Ala Lys Ser Phe Arg Cys Ala Leu Leu Ser His Arg Asp Gly
             85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
        130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
        210                 215                 220

Leu Leu Asp Leu Pro Asp Asp Ala Pro Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
        290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 3
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 3 atg tct aga tta gat aaa agt aaa gtg att aac agc gca tta gag ctg       48
Met Ser Arg Leu Asp Lys Ser Lys Val Ile Asn Ser Ala Leu Glu Leu
 1               5                  10                  15 ctt aat gag gtc gga atc gaa ggt tta aca acc cgt aaa ctc gcc cag       96
Leu Asn Glu Val Gly Ile Glu Gly Leu Thr Thr Arg Lys Leu Ala Gln
            20                  25                  30 aag cta ggt gta gag cag cct aca ttg tat tgg cat gta aaa aat aag      144
Lys Leu Gly Val Glu Gln Pro Thr Leu Tyr Trp His Val Lys Asn Lys
        35                  40                  45 cgg gct ttg ctc gac gcc tta gcc att gag atg tta gat agg cac cat      192
Arg Ala Leu Leu Asp Ala Leu Ala Ile Glu Met Leu Asp Arg His His
    50                  55                  60 act cac ttt tgc cct tta gaa ggg gaa agc tgg caa gac ttt tta cgt      240
```

```
                Thr His Phe Cys Pro Leu Glu Gly Glu Ser Trp Gln Asp Phe Leu Arg
                 65                  70                  75                  80 aat aac gct aaa agt ttt aga tgt gct tta cta agt cat cgc gat gga                288
Asn Asn Ala Lys Ser Phe Arg Cys Ala Leu Leu Ser His Arg Asp Gly
                 85                  90                  95 gca aaa gta cat tta ggt aca cgg cct aca gaa aaa cag tat gaa act                336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag                384
Leu Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc                432
Asn Ala Leu Tyr Ala Leu Ser Ala Val Gly His Phe Thr Leu Gly Cys
    130                 135                 140 gta ttg gaa gat caa gag cat caa gtc gct aaa gaa gaa agg gaa aca                480
Val Leu Glu Asp Gln Glu His Gln Val Ala Lys Glu Glu Arg Glu Thr
145                 150                 155                 160 cct act act gat agt atg ccg cca tta gta cga caa gct atc gaa tta                528
Pro Thr Thr Asp Ser Met Pro Pro Leu Val Arg Gln Ala Ile Glu Leu
                165                 170                 175 ttt gat cac caa ggt gca gag cca gcc ttc ttg ttc ggc ctt gaa ttg                576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg                624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc                672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg                720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg                768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac                816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat                864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc                912
Leu Asp Met Leu Gly Asp Gly Asp Ser Pro Gly Pro Gly Phe Thr Pro
    290                 295                 300 cac gac tcc gcc ccc tac ggc gct ctg gat atg gcc gac ttc gag ttt                960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag              1008
Glu Gln Met Phe Thr Asp Ala Leu Gly Ile Asp Glu Tyr Gly Gly
                325                 330                 335

<210> SEQ ID NO 4
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 4

Met Ser Arg Leu Asp Lys Ser Lys Val Ile Asn Ser Ala Leu Glu Leu
```

```
                1               5              10              15
        Leu Asn Glu Val Gly Ile Glu Gly Leu Thr Thr Arg Lys Leu Ala Gln
                            20                  25                  30

Lys Leu Gly Val Glu Gln Pro Thr Leu Tyr Trp His Val Lys Asn Lys
                        35                  40                  45

Arg Ala Leu Leu Asp Ala Leu Ala Ile Glu Met Leu Asp Arg His His
                    50                  55                  60

Thr His Phe Cys Pro Leu Gly Gly Glu Ser Trp Gln Asp Phe Leu Arg
        65                  70                  75                  80

Asn Asn Ala Lys Ser Phe Arg Cys Ala Leu Leu Ser His Arg Asp Gly
                        85                  90                  95

Ala Lys Val His Leu Gly Thr Arg Pro Thr Glu Lys Gln Tyr Glu Thr
                        100                 105                 110

Leu Glu Asn Gln Leu Ala Phe Leu Cys Gln Gln Gly Phe Ser Leu Glu
                        115                 120                 125

Asn Ala Leu Tyr Ala Leu Ser Ala Val Gly His Phe Thr Leu Gly Cys
                        130                 135                 140

Val Leu Glu Asp Gln Glu His Gln Val Ala Lys Glu Glu Arg Glu Thr
        145                 150                 155                 160

Pro Thr Thr Asp Ser Met Pro Pro Leu Val Arg Gln Ala Ile Glu Leu
                        165                 170                 175

Phe Asp His Gln Gly Ala Glu Pro Ala Phe Leu Phe Gly Leu Glu Leu
                        180                 185                 190

Ile Ile Cys Gly Leu Glu Lys Gln Leu Lys Cys Glu Ser Gly Ser Ala
                        195                 200                 205

Tyr Ser Arg Ala Arg Thr Lys Asn Asn Tyr Gly Ser Thr Ile Glu Gly
                        210                 215                 220

Leu Leu Asp Leu Pro Asp Asp Ala Pro Glu Glu Ala Gly Leu Ala
        225                 230                 235                 240

Ala Pro Arg Leu Ser Phe Leu Pro Ala Gly His Thr Arg Arg Leu Ser
                        245                 250                 255

Thr Ala Pro Pro Thr Asp Val Ser Leu Gly Asp Glu Leu His Leu Asp
                        260                 265                 270

Gly Glu Asp Val Ala Met Ala His Ala Asp Ala Leu Asp Asp Phe Asp
                        275                 280                 285

Leu Asp Met Leu Gly Asp Gly Asp Ser Pro Gly Pro Gly Phe Thr Pro
                        290                 295                 300

His Asp Ser Ala Pro Tyr Gly Ala Leu Asp Met Ala Asp Phe Glu Phe
                        305                 310                 315                 320

Glu Gln Met Phe Thr Asp Ala Leu Gly Ile Asp Glu Tyr Gly Gly
                        325                 330                 335

<210> SEQ ID NO 5
<211> LENGTH: 747
<212> TYPE: DNA
<213> ORGANISM: Artificial Sequence
<220> FEATURE:
<223> OTHER INFORMATION: Description of Artificial Sequence: hybrid gene

<400> SEQUENCE: 5
atgtctagac tggacaagag caaagtcata aactctgctc tggaattact caatggagtc      60
ggtatcgaag gcctgacgac aaggaaactc gctcaaaagc tgggagttga gcagcctacc     120
ctgtactggc acgtgaagaa caagcgggcc ctgctcgatg ccctgccaat cgagatgctg     180
gacaggcatc ataccacctt ctgccccctg gaaggcgagt catggcaaga ctttctgcgg     240
```

```
aacaacgcca agtcattccg ctgtgctctc ctctcacatc gcgacgggc taaagtgcat      300 ctcggcaccc gcccaacaga gaaacagtac gaaaccctgg aaaatcagct cgcgttcctg      360
tgtcagcaag gcttctccct ggagaacgca ctgtacgctc tgtccgccgt gggccacttt      420
acactgggct gcgtattgga ggaacaggag catcaagtag caaagagga agagagaca      480 cctaccaccg attctatgcc cccacttctg agacaagcaa ttgagctgtt cgaccggcag      540
ggagccgaac ctgccttcct tttcggcctg aactaatca tatgtggcct ggagaaacag      600
ctaaagtgcg aaagcggcgg gccggccgac gcccttgacg attttgactt agacatgctc      660
ccagccgatg cccttgacga ctttgacctt gatatgctgc ctgctgacgc tcttgacgat      720
tttgaccttg acatgctccc cgggtaa                                         747
```

```
<210> SEQ ID NO 6
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 6 atg tct aga tta gat aaa agt aaa gtg att aac agc gca tta gag ctg       48
Met Ser Arg Leu Asp Lys Ser Lys Val Ile Asn Ser Ala Leu Glu Leu
 1               5                  10                  15 ctt aat ggg gtc gga atc gaa ggt tta aca acc cgt aaa ctc gcc cag       96
Leu Asn Gly Val Gly Ile Glu Gly Leu Thr Thr Arg Lys Leu Ala Gln
             20                  25                  30 aag cta ggt gta gag cag cct aca ttg tat tgg cat gta aaa aat aag      144
Lys Leu Gly Val Glu Gln Pro Thr Leu Tyr Trp His Val Lys Asn Lys
         35                  40                  45 cgg gct ttg ctc gac gcc tta ccc att gag atg tta gat agg cac cat      192
Arg Ala Leu Leu Asp Ala Leu Pro Ile Glu Met Leu Asp Arg His His
     50                  55                  60 act cac ttt tgc cct tta gaa ggg gaa agc tgg caa gat ttt tta cgt      240
Thr His Phe Cys Pro Leu Glu Gly Glu Ser Trp Gln Asp Phe Leu Arg
 65                  70                  75                  80 aat aac gct aaa agt ttt aga tgt gct tta cta agt cat cgc gat gga      288
Asn Asn Ala Lys Ser Phe Arg Cys Ala Leu Leu Ser His Arg Asp Gly
                 85                  90                  95 gca aaa gta cat tta ggt aca cgg cct aca gaa aaa cag tat gaa act      336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag      384
Leu Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc      432
Asn Ala Leu Tyr Ala Leu Ser Ala Val Gly His Phe Thr Leu Gly Cys
    130                 135                 140 gta ttg gaa gat caa gag cat caa gtc gct aaa gaa gaa agg gaa aca      480
Val Leu Glu Asp Gln Glu His Gln Val Ala Lys Glu Glu Arg Glu Thr
145                 150                 155                 160 cct act act gat agt atg ccg cca tta tta cga caa gct atc gaa tta      528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg      576
Phe Asp His Gln Gly Ala Glu Pro Ala Phe Leu Phe Gly Leu Glu Leu
            180                 185                 190
```

```
atc ata tgc gga tta gaa aaa caa ctt aaa tgt gaa agt ggg tcc gcg      624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc      672
Tyr Ser Arg Ala Arg Thr Lys Asn Asn Tyr Gly Ser Thr Ile Glu Gly
210                 215                 220 ctg ctc gat ctc ccg gac gac gac gcc ccc gaa gag gcg ggg ctg gcg      720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg      768
Ala Pro Arg Leu Ser Phe Leu Pro Ala Gly His Thr Arg Arg Leu Ser
            245                 250                 255 acg gcc ccc ccg acc gat gtc agc ctg ggg gac gag ctc cac tta gac      816
Thr Ala Pro Pro Thr Asp Val Ser Leu Gly Asp Glu Leu His Leu Asp
        260                 265                 270 ggc gag gac gtg gcg atg gcg cat gcc gac gcg cta gac gat ttc gat      864
Gly Glu Asp Val Ala Met Ala His Ala Asp Ala Leu Asp Asp Phe Asp
275                 280                 285 ctg gac atg ttg ggg gac ggg gat tcc ccg ggt ccg gga ttt acc ccc      912
Leu Asp Met Leu Gly Asp Gly Asp Ser Pro Gly Pro Gly Phe Thr Pro
290                 295                 300 cac gac tcc gcc ccc tac ggc gct ctg gat atg gcc gac ttc gag ttt      960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag     1008
Glu Gln Met Phe Thr Asp Ala Leu Gly Ile Asp Glu Tyr Gly Gly
            325                 330                 335

<210> SEQ ID NO 7
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 7

Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
```

```
                      165                 170                 175
Phe Asp His Gln Gly Ala Glu Pro Ala Phe Leu Phe Gly Leu Glu Leu
                180                 185                 190

Ile Ile Cys Gly Leu Glu Lys Gln Leu Lys Cys Glu Ser Gly Ser Ala
            195                 200                 205

Tyr Ser Arg Ala Arg Thr Lys Asn Asn Tyr Gly Ser Thr Ile Glu Gly
        210                 215                 220

Leu Leu Asp Leu Pro Asp Asp Ala Pro Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
                260                 265                 270

Gly Glu Asp Val Ala Met Ala His Ala Asp Ala Leu Asp Asp Phe Asp
            275                 280                 285

Leu Asp Met Leu Gly Asp Gly Asp Ser Pro Gly Pro Gly Phe Thr Pro
        290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 8
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 8 atg tct aga tta gat aaa agt aaa gtg att aac ggc gca tta gag ctg      48
Met Ser Arg Leu Asp Lys Ser Lys Val Ile Asn Gly Ala Leu Glu Leu
 1               5                  10                  15 ctt aat ggg gtc gga atc gaa ggt tta aca acc cgt aaa ctc gcc cag      96
Leu Asn Gly Val Gly Ile Glu Gly Leu Thr Thr Arg Lys Leu Ala Gln
             20                  25                  30 aag cta ggt gta gag cag cct aca ttg tat tgg cat gta aaa aat aag     144
Lys Leu Gly Val Glu Gln Pro Thr Leu Tyr Trp His Val Lys Asn Lys
         35                  40                  45 cgg gct ttg ctc gac gcc tta ccc att gag atg tta gat agg cac cat     192
Arg Ala Leu Leu Asp Ala Leu Pro Ile Glu Met Leu Asp Arg His His
     50                  55                  60 act cac ttt tgc cct tta gaa ggg gaa agc tgg caa gat ttt tta cgt     240
Thr His Phe Cys Pro Leu Glu Gly Glu Ser Trp Gln Asp Phe Leu Arg
 65                  70                  75                  80 aat aac gct aaa agt ttt aga tgt gct tta cta agt cat cgc gat gga     288
Asn Asn Ala Lys Ser Phe Arg Cys Ala Leu Leu Ser His Arg Asp Gly
                 85                  90                  95 gca aaa gta cat tta ggt aca cgg cct aca gaa aaa cag tat gaa act     336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag     384
Leu Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc     432
Asn Ala Leu Tyr Ala Leu Ser Ala Val Gly His Phe Thr Leu Gly Cys
```

```
           130                 135                 140
gta ttg gaa gat caa gag cat caa gtc gct aaa gaa gaa agg gaa aca    480
Val Leu Glu Asp Gln Glu His Gln Val Ala Lys Glu Glu Arg Glu Thr
145                 150                 155                 160 cct act act gat agt atg ccg cca tta tta cga caa gct atc gaa tta    528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg    576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg    624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc    672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg    720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg    768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac    816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat    864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc    912
Leu Asp Met Leu Gly Asp Gly Asp Ser Pro Gly Pro Gly Phe Thr Pro
    290                 295                 300 cac gac tcc gcc ccc tac ggc gct ctg gat atg gcc gac ttc gag ttt    960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag   1008
Glu Gln Met Phe Thr Asp Ala Leu Gly Ile Asp Glu Tyr Gly Gly
                325                 330                 335

<210> SEQ ID NO 9
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 9

Met Ser Arg Leu Asp Lys Ser Lys Val Ile Asn Gly Ala Leu Glu Leu
 1               5                  10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95
```

```
Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 10
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 10 atg tct aga tta gat aaa agt aaa gtg att aac ggc gca tta gag ctg      48
Met Ser Arg Leu Asp Lys Ser Lys Val Ile Asn Gly Ala Leu Glu Leu
1               5                   10                  15 ctt aat ggg gtc gga atc gaa ggt tta aca acc cgt aaa ctc gcc cag      96
Leu Asn Gly Val Gly Ile Glu Gly Leu Thr Thr Arg Lys Leu Ala Gln
            20                  25                  30 aag cta ggt gta gag cag cct aca ttg tat tgg cat gta aaa aat aag     144
Lys Leu Gly Val Glu Gln Pro Thr Leu Tyr Trp His Val Lys Asn Lys
        35                  40                  45 cgg gct ttg ctc gac gcc tta ccc att gag atg tta gat agg cac cat     192
Arg Ala Leu Leu Asp Ala Leu Pro Ile Glu Met Leu Asp Arg His His
    50                  55                  60 act cac ttt tgc cct tta gaa ggg gaa agc tgg caa gat ttt tta cgt     240
Thr His Phe Cys Pro Leu Glu Gly Glu Ser Trp Gln Asp Phe Leu Arg
65                  70                  75                  80 aat aac gct aaa agt ttt aga tgt gct tta cta agt cat cgc gat gga     288
```

```
                Asn Asn Ala Lys Ser Phe Arg Cys Ala Leu Leu Ser His Arg Asp Gly
                            85                  90                  95 gca aaa gta cat tta ggt aca cgg cct aca gaa aaa cag tat gaa act           336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag           384
Leu Glu Asn Gln Leu Ala Phe Leu Cys Gln Gln Gly Phe Ser Leu Glu
            115                 120                 125 aat gca tta tat gca ctc agc gct gtg ggg cac ttt act tta ggt tgc           432
Asn Ala Leu Tyr Ala Leu Ser Ala Val Gly His Phe Thr Leu Gly Cys
        130                 135                 140 gta ttg gaa gaa caa gag cat caa gtc gct aaa gaa gaa agg gaa aca           480
Val Leu Glu Glu Gln Glu His Gln Val Ala Lys Glu Glu Arg Glu Thr
145                 150                 155                 160 cct act act gat agt atg ccg cca tta tta cga caa gct atc gaa tta           528
Pro Thr Thr Asp Ser Met Pro Pro Leu Leu Arg Gln Ala Ile Glu Leu
                165                 170                 175 ttt gat cgc caa ggt gca gag cca gcc tta ttc ggc ctt gaa ttg               576
Phe Asp Arg Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg           624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc           672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg           720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg           768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac           816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat           864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc           912
Leu Asp Met Leu Gly Asp Gly Asp Ser Pro Gly Pro Gly Phe Thr Pro
    290                 295                 300 cac gac tcc gcc ccc tac ggc gct ctg gat atg gcc gac ttc gag ttt           960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag          1008
Glu Gln Met Phe Thr Asp Ala Leu Gly Ile Asp Glu Tyr Gly Gly
                325                 330                 335

<210> SEQ ID NO 11
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 11

Met Ser Arg Leu Asp Lys Ser Lys Val Ile Asn Gly Ala Leu Glu Leu
 1               5                  10                  15

Leu Asn Gly Val Gly Ile Glu Gly Leu Thr Thr Arg Lys Leu Ala Gln
            20                  25                  30
```

| | | | | | | | | | | | |
|---|---|---|---|---|---|---|---|---|---|---|---|
|Lys|Leu|Gly|Val|Glu|Gln|Pro|Thr|Leu|Tyr|Trp|His|Val|Lys|Asn|Lys|
| | |35| | | |40| | | |45| | | | | |

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
    275                 280                 285

Leu Asp Met Leu Gly Asp Gly Asp Ser Pro Gly Pro Gly Phe Thr Pro
        290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 12
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 12

```
atg tct aga tta gat aaa agt aaa gtg att aac agc gca tta gag ctg     48
Met Ser Arg Leu Asp Lys Ser Lys Val Ile Asn Ser Ala Leu Glu Leu
 1               5                  10                  15 ctt aat gag gtc gga atc gaa ggt tta gca acc cgt aaa ctc gcc cag     96
Leu Asn Glu Val Gly Ile Glu Gly Leu Ala Thr Arg Lys Leu Ala Gln
             20                  25                  30
```

```
aag cta ggt gta gag cag cct aca ttg tat tgg cat gta aaa aat aag    144
Lys Leu Gly Val Glu Gln Pro Thr Leu Tyr Trp His Val Lys Asn Lys
         35                  40                  45 cgg gct ttg ctc gac gcc tta gcc att gag atg tta gat agg cac cat    192
Arg Ala Leu Leu Asp Ala Leu Ala Ile Glu Met Leu Asp Arg His His
 50                  55                  60 act cac ttt tgc cct tta gaa ggg gaa agc tgg caa gat ttt tta cgt    240
Thr His Phe Cys Pro Leu Glu Gly Glu Ser Trp Gln Asp Phe Leu Arg
 65                  70                  75                  80 aat aac gct aaa agt ttt aga tgt gct tta cta agt cat cgc ggt gga    288
Asn Asn Ala Lys Ser Phe Arg Cys Ala Leu Leu Ser His Arg Gly Gly
                 85                  90                  95 gca aaa gta cat tta ggt aca cgg cct aca gaa aaa cag tat gaa act    336
Ala Lys Val His Leu Gly Thr Arg Pro Thr Glu Lys Gln Tyr Glu Thr
        100                 105                 110 ctc gaa aat caa tta gcc ttt tta tgc caa caa ggt ttt tca cta gag    384
Leu Glu Asn Gln Leu Ala Phe Leu Cys Gln Gln Gly Phe Ser Leu Glu
            115                 120                 125 aat gca tta tat gca ctc agc gct gtg ggg cat ttt act tta ggt tgc    432
Asn Ala Leu Tyr Ala Leu Ser Ala Val Gly His Phe Thr Leu Gly Cys
130                 135                 140 gta ttg gaa gat caa gag cat caa gtc gct aaa gaa gaa agg gaa aca    480
Val Leu Glu Asp Gln Glu His Gln Val Ala Lys Glu Glu Arg Glu Thr
145                 150                 155                 160 cct act act gat agt atg ccg cca tta tta cga caa gct atc gaa tta    528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg    576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg    624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc    672
Tyr Ser Arg Ala Arg Thr Lys Asn Asn Tyr Gly Ser Thr Ile Glu Gly
210                 215                 220 ctg ctc gat ctc ccg gac gac gac gcc ccc gaa gag gcg ggg ctg gcg    720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg    768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac    816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat    864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc    912
Leu Asp Met Leu Gly Asp Gly Asp Ser Pro Gly Pro Gly Phe Thr Pro
290                 295                 300 cac gac tcc gcc ccc tac ggc gct ctg gat atg gcc gac ttc gag ttt    960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag   1008
Glu Gln Met Phe Thr Asp Ala Leu Gly Ile Asp Glu Tyr Gly Gly
                325                 330                 335
```

<210> SEQ ID NO 13
<211> LENGTH: 335

```
<212> TYPE: PRT
<213> ORGANISM: Artificial Sequence
<220> FEATURE:
<223> OTHER INFORMATION: Description of Artificial Sequence: fusion
      protein

<400> SEQUENCE: 13

Met Ser Arg Leu Asp Lys Ser Lys Val Ile Asn Ser Ala Leu Glu Leu
  1               5                  10                  15

Leu Asn Glu Val Gly Ile Glu Gly Leu Ala Thr Arg Lys Leu Ala Gln
                 20                  25                  30

Lys Leu Gly Val Glu Gln Pro Thr Leu Tyr Trp His Val Lys Asn Lys
             35                  40                  45

Arg Ala Leu Leu Asp Ala Leu Ala Ile Glu Met Leu Asp Arg His His
         50                  55                  60

Thr His Phe Cys Pro Leu Glu Gly Glu Ser Trp Gln Asp Phe Leu Arg
 65                  70                  75                  80

Asn Asn Ala Lys Ser Phe Arg Cys Ala Leu Leu Ser His Arg Gly Gly
                 85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 14
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
```

```
<221> NAME/KEY: CDS
<222> LOCATION: (1)..(1005)

<400> SEQUENCE: 14 atg tct aga tta gat aaa agt aaa gtg att aac agc gca tta gag ctg         48
Met Ser Arg Leu Asp Lys Ser Lys Val Ile Asn Ser Ala Leu Glu Leu
1               5                   10                  15 ctt aat gag gtc gga atc gaa ggt tta aca acc cgt aaa ctc gcc cag         96
Leu Asn Glu Val Gly Ile Glu Gly Leu Thr Thr Arg Lys Leu Ala Gln
            20                  25                  30 aag cta ggt gta gag cag cct aca ttg tat tgg cat gta aaa aat aag        144
Lys Leu Gly Val Glu Gln Pro Thr Leu Tyr Trp His Val Lys Asn Lys
        35                  40                  45 cgg gct ttg ctc gac gcc tta gcc att gag atg tta gat agg cac cat        192
Arg Ala Leu Leu Asp Ala Leu Ala Ile Glu Met Leu Asp Arg His His
    50                  55                  60 act cac ttt tgc cct tta gaa ggg gaa agc tgg caa gat ttt tta cgt        240
Thr His Phe Cys Pro Leu Glu Gly Glu Ser Trp Gln Asp Phe Leu Arg
65                  70                  75                  80 aat aac gct aaa agt ttt aga tgt gct tta cta agt cat cgc gat aga        288
Asn Asn Ala Lys Ser Phe Arg Cys Ala Leu Leu Ser His Arg Asp Arg
                85                  90                  95 gca aaa gta cat tta ggt aca cgg cct aca gaa aaa cag tat gaa act        336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag        384
Leu Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc        432
Asn Ala Leu Tyr Ala Leu Ser Ala Val Gly His Phe Thr Leu Gly Cys
    130                 135                 140 gta ttg gaa gat caa gag cat caa gtc gct aaa gaa gaa agg gaa aca        480
Val Leu Glu Asp Gln Glu His Gln Val Ala Lys Glu Glu Arg Glu Thr
145                 150                 155                 160 cct act act gat agt atg ccg cca tta tta cga caa gct atc gaa tta        528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg        576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg        624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc        672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg        720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg        768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac        816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat        864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc        912
Leu Asp Met Leu Gly Asp Gly Asp Ser Pro Gly Pro Gly Phe Thr Pro
```

```
                 290                 295                 300
cac gac tcc gcc ccc tac ggc gct ctg gat atg gcc gac ttc gag ttt    960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag   1008
Glu Gln Met Phe Thr Asp Ala Leu Gly Ile Asp Glu Tyr Gly Gly
                325                 330                 335
```

<210> SEQ ID NO 15
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 15

```
Met Ser Arg Leu Asp Lys Ser Lys Val Ile Asn Ser Ala Leu Glu Leu
1               5                  10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
        50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Arg
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
```

```
                305                 310                 315                 320
        Glu Gln Met Phe Thr Asp Ala Leu Gly Ile Asp Glu Tyr Gly Gly
                        325                 330                 335

<210> SEQ ID NO 16
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 16 atg tct aga tta gat aaa agt aaa gtg att aac agc gca tta gag ctg        48
Met Ser Arg Leu Asp Lys Ser Lys Val Ile Asn Ser Ala Leu Glu Leu
 1               5                  10                  15 ctt aat gag gtc gga atc gaa ggt tta aca acc cgt aaa ctc gcc cag        96
Leu Asn Glu Val Gly Ile Glu Gly Leu Thr Thr Arg Lys Leu Ala Gln
                20                  25                  30 aag cta ggt gta gag cag cct aca ttg tat tgg cat gta aaa aat aag       144
Lys Leu Gly Val Glu Gln Pro Thr Leu Tyr Trp His Val Lys Asn Lys
            35                  40                  45 cgg gct ttg ctc gac gcc tta gcc att gag atg tta gat agg cac cat       192
Arg Ala Leu Leu Asp Ala Leu Ala Ile Glu Met Leu Asp Arg His His
        50                  55                  60 act cac ttt tgc cct tta gaa ggg gaa agc tgg caa gat ttt tta cgt       240
Thr His Phe Cys Pro Leu Glu Gly Glu Ser Trp Gln Asp Phe Leu Arg
 65                  70                  75                  80 aat aac gct aaa agt ttt aga tgt gct tta cta agt cat cgc gat gga       288
Asn Asn Ala Lys Ser Phe Arg Cys Ala Leu Leu Ser His Arg Asp Gly
                85                  90                  95 gca aaa gaa cat tta ggt aca cgg cct aca gaa aaa cag tat gaa act       336
Ala Lys Glu His Leu Gly Thr Arg Pro Thr Glu Lys Gln Tyr Glu Thr
           100                 105                 110 ctc gaa aat caa tta gcc ttt tta tgc caa caa ggt ttt tca cta gag       384
Leu Glu Asn Gln Leu Ala Phe Leu Cys Gln Gln Gly Phe Ser Leu Glu
       115                 120                 125 aat gca tta tat gca ctc agc gct gtg ggg cat ttt act tta ggt tgc       432
Asn Ala Leu Tyr Ala Leu Ser Ala Val Gly His Phe Thr Leu Gly Cys
   130                 135                 140 gta ttg gaa gat caa gag cat caa gtc gct aaa gaa gaa agg gaa aca       480
Val Leu Glu Asp Gln Glu His Gln Val Ala Lys Glu Glu Arg Glu Thr
145                 150                 155                 160 cct act act gat agt atg ccg cca tta tta cga caa gct atc gaa tta       528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg       576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg       624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc       672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg       720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg       768
```

```
                Ala Pro Arg Leu Ser Phe Leu Pro Ala Gly His Thr Arg Arg Leu Ser
                                245                 250                 255 acg gcc ccc ccg acc gat gtc agc ctg ggg gac gag ctc cac tta gac           816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat           864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc           912
Leu Asp Met Leu Gly Asp Gly Asp Ser Pro Gly Pro Gly Phe Thr Pro
    290                 295                 300 cac gac tcc gcc ccc tac ggc gct ctg gat atg gcc gac ttc gag ttt           960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag          1008
Glu Gln Met Phe Thr Asp Ala Leu Gly Ile Asp Glu Tyr Gly Gly
                325                 330                 335

<210> SEQ ID NO 17
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 17

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Glu His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240
```

```
Ala Pro Arg Leu Ser Phe Leu Pro Ala Gly His Thr Arg Leu Ser
            245                 250                 255

Thr Ala Pro Pro Thr Asp Val Ser Leu Gly Asp Glu Leu His Leu Asp
        260                 265                 270

Gly Glu Asp Val Ala Met Ala His Ala Asp Ala Leu Asp Phe Asp
            275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 18
<211> LENGTH: 1005
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1002)

<400> SEQUENCE: 18 atg tct aga tta gat aaa agt aaa gtg att aac agc gca tta gag ctg     48
Met Ser Arg Leu Asp Lys Ser Lys Val Ile Asn Ser Ala Leu Glu Leu
 1               5                  10                  15 ctt aat ggg gtc gga atc gaa ggt tta aca acc cgt aaa ctc gcc cag    96
Leu Asn Gly Val Gly Ile Glu Gly Leu Thr Thr Arg Lys Leu Ala Gln
            20                  25                  30 aag cta ggt gta gag cag cct aca ttg tat tgg cat gta aaa aat aag   144
Lys Leu Gly Val Glu Gln Pro Thr Leu Tyr Trp His Val Lys Asn Lys
        35                  40                  45 cgg gct ttg ctc gac gcc tta gcc att gag atg tta gat agg cac cat   192
Arg Ala Leu Leu Asp Ala Leu Ala Ile Glu Met Leu Asp Arg His His
    50                  55                  60 act cac ttt tgc cct tta gaa ggg gaa agc tgg caa gat ttt tta cgt   240
Thr His Phe Cys Pro Leu Glu Gly Glu Ser Trp Gln Asp Phe Leu Arg
65                  70                  75                  80 aat aac gct aaa agt ttt agt gct tta cta agt cat cgc gat gga gca   288
Asn Asn Ala Lys Ser Phe Ser Ala Leu Leu Ser His Arg Asp Gly Ala
                85                  90                  95 aaa gta cat tta ggt aca cgg cct aca gaa aaa cag tat gaa act ctc   336
Lys Val His Leu Gly Thr Arg Pro Thr Glu Lys Gln Tyr Glu Thr Leu
            100                 105                 110 gaa aat caa tta gcc ttt tta tgc caa caa ggt ttt tca cta gag aat   384
Glu Asn Gln Leu Ala Phe Leu Cys Gln Gln Gly Phe Ser Leu Glu Asn
        115                 120                 125 gca tta tat gca ctc agc gct gtg ggg cat ttt act tta ggt tgc gta   432
Ala Leu Tyr Ala Leu Ser Ala Val Gly His Phe Thr Leu Gly Cys Val
    130                 135                 140 ttg gaa gat caa gag cat caa gtc gct aaa gaa gaa agg gaa aca cct   480
Leu Glu Asp Gln Glu His Gln Val Ala Lys Glu Glu Arg Glu Thr Pro
145                 150                 155                 160 act act gat agt atg ccg cca tta tta cga caa gct atc gaa tta ttt   528
Thr Thr Asp Ser Met Pro Pro Leu Leu Arg Gln Ala Ile Glu Leu Phe
                165                 170                 175 gat cac caa ggt gca gag cca gcc ttc tta ttc ggc ctt gaa ttg atc   576
Asp His Gln Gly Ala Glu Pro Ala Phe Leu Phe Gly Leu Glu Leu Ile
            180                 185                 190
```

| | | | | | | | | | | | | | | | | |
|---|---|---|---|---|---|---|---|---|---|---|---|---|---|---|---|---|
| ata | tgc | gga | tta | gaa | aaa | caa | ctt | aaa | tgt | gaa | agt | ggg | tcc | gcg | tac | 624 |
| Ile | Cys | Gly | Leu | Glu | Lys | Gln | Leu | Lys | Cys | Glu | Ser | Gly | Ser | Ala | Tyr | |
| | | 195 | | | | | 200 | | | | | 205 | | | | |
| agc | cgc | gcg | cgt | acg | aaa | aac | aat | tac | ggg | tct | acc | atc | gag | ggc | ctg | 672 |
| Ser | Arg | Ala | Arg | Thr | Lys | Asn | Asn | Tyr | Gly | Ser | Thr | Ile | Glu | Gly | Leu | |
| | 210 | | | | | 215 | | | | | 220 | | | | | |
| ctc | gat | ctc | ccg | gac | gac | gac | gcc | ccc | gaa | gag | gcg | ggg | ctg | gcg | gct | 720 |
| Leu | Asp | Leu | Pro | Asp | Asp | Asp | Ala | Pro | Glu | Glu | Ala | Gly | Leu | Ala | Ala | |
| 225 | | | | 230 | | | | | 235 | | | | | 240 | | |
| ccg | cgc | ctg | tcc | ttt | ctc | ccc | gcg | gga | cac | acg | cgc | aga | ctg | tcg | acg | 768 |
| Pro | Arg | Leu | Ser | Phe | Leu | Pro | Ala | Gly | His | Thr | Arg | Arg | Leu | Ser | Thr | |
| | | | 245 | | | | | 250 | | | | | 255 | | | |
| gcc | ccc | ccg | acc | gat | gtc | agc | ctg | ggg | gac | gag | ctc | cac | tta | gac | ggc | 816 |
| Ala | Pro | Pro | Thr | Asp | Val | Ser | Leu | Gly | Asp | Glu | Leu | His | Leu | Asp | Gly | |
| | | 260 | | | | | 265 | | | | | 270 | | | | |
| gag | gac | gtg | gcg | atg | gcg | cat | gcc | gac | gcg | cta | gac | gat | ttc | gat | ctg | 864 |
| Glu | Asp | Val | Ala | Met | Ala | His | Ala | Asp | Ala | Leu | Asp | Asp | Phe | Asp | Leu | |
| | 275 | | | | | 280 | | | | | 285 | | | | | |
| gac | atg | ttg | ggg | gac | ggg | gat | tcc | ccg | ggt | ccg | gga | ttt | acc | ccc | cac | 912 |
| Asp | Met | Leu | Gly | Asp | Gly | Asp | Ser | Pro | Gly | Pro | Gly | Phe | Thr | Pro | His | |
| | 290 | | | | | 295 | | | | | 300 | | | | | |
| gac | tcc | gcc | ccc | tac | ggc | gct | ctg | gat | atg | gcc | gac | ttc | gag | ttt | gag | 960 |
| Asp | Ser | Ala | Pro | Tyr | Gly | Ala | Leu | Asp | Met | Ala | Asp | Phe | Glu | Phe | Glu | |
| 305 | | | | 310 | | | | | 315 | | | | | 320 | | |
| cag | atg | ttt | acc | gat | gcc | ctt | gga | att | gac | gag | tac | ggt | ggg | tag | | 1005 |
| Gln | Met | Phe | Thr | Asp | Ala | Leu | Gly | Ile | Asp | Glu | Tyr | Gly | Gly | | | |
| | | | 325 | | | | | 330 | | | | | | | | |

<210> SEQ ID NO 19
<211> LENGTH: 334
<212> TYPE: PRT
<213> ORGANISM: Artificial Sequence
<220> FEATURE:
<223> OTHER INFORMATION: Description of Artificial Sequence: fusion protein

<400> SEQUENCE: 19

Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Ser Ala Leu Leu Ser His Arg Asp Gly Ala
                85                  90                  95

Lys Val His Leu Gly Thr Arg Pro Thr Glu Lys Gln Tyr Glu Thr Leu
            100                 105                 110

Glu Asn Gln Leu Ala Phe Leu Cys Gln Gln Gly Phe Ser Leu Glu Asn
        115                 120                 125

Ala Leu Tyr Ala Leu Ser Ala Val Gly His Phe Thr Leu Gly Cys Val
    130                 135                 140

Leu Glu Asp Gln Glu His Gln Val Ala Lys Glu Glu Arg Glu Thr Pro
145                 150                 155                 160

Thr Thr Asp Ser Met Pro Pro Leu Leu Arg Gln Ala Ile Glu Leu Phe
                165                 170                 175

```
Asp His Gln Gly Ala Glu Pro Ala Phe Leu Phe Gly Leu Glu Leu Ile
            180                 185                 190

Ile Cys Gly Leu Glu Lys Gln Leu Lys Cys Glu Ser Gly Ser Ala Tyr
            195                 200                 205

Ser Arg Ala Arg Thr Lys Asn Asn Tyr Gly Ser Thr Ile Glu Gly Leu
            210                 215                 220

Leu Asp Leu Pro Asp Asp Ala Pro Glu Glu Ala Gly Leu Ala Ala
225                 230                 235                 240

Pro Arg Leu Ser Phe Leu Pro Ala Gly His Thr Arg Arg Leu Ser Thr
                245                 250                 255

Ala Pro Pro Thr Asp Val Ser Leu Gly Asp Glu Leu His Leu Asp Gly
            260                 265                 270

Glu Asp Val Ala Met Ala His Ala Asp Ala Leu Asp Asp Phe Asp Leu
            275                 280                 285

Asp Met Leu Gly Asp Gly Asp Ser Pro Gly Pro Gly Phe Thr Pro His
            290                 295                 300

Asp Ser Ala Pro Tyr Gly Ala Leu Asp Met Ala Asp Phe Glu Phe Glu
305                 310                 315                 320

Gln Met Phe Thr Asp Ala Leu Gly Ile Asp Glu Tyr Gly Gly
                325                 330
```

```
<210> SEQ ID NO 20
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 20 atg tct aga tta gat aaa agt aaa gtg att aac agc gca tta gag ctg     48
Met Ser Arg Leu Asp Lys Ser Lys Val Ile Asn Ser Ala Leu Glu Leu
  1               5                  10                  15 ctt aat gag gtc gga atc gaa ggt tta aca acc cgt aaa ctc gcc cag     96
Leu Asn Glu Val Gly Ile Glu Gly Leu Thr Thr Arg Lys Leu Ala Gln
             20                  25                  30 aag cta ggt gta gag cag cct aca ttg tat tgg cat gta aaa aat aag    144
Lys Leu Gly Val Glu Gln Pro Thr Leu Tyr Trp His Val Lys Asn Lys
         35                  40                  45 cgg gct ttg ctc gac gcc tta gcc att gag atg tta gat agg cac cat    192
Arg Ala Leu Leu Asp Ala Leu Ala Ile Glu Met Leu Asp Arg His His
     50                  55                  60 act cac ttt tgc cct tta gaa ggg gaa agc tgg caa gat ttt tta cgt    240
Thr His Phe Cys Pro Leu Glu Gly Glu Ser Trp Gln Asp Phe Leu Arg
 65                  70                  75                  80 aat aac gct aaa agt ttt aga tgt gct tta cta agt cat cgc gat gga    288
Asn Asn Ala Lys Ser Phe Arg Cys Ala Leu Leu Ser His Arg Asp Gly
                 85                  90                  95 gca aaa gaa cat tta ggt aca cgg cct aca gaa aaa cag tat gaa act    336
Ala Lys Glu His Leu Gly Thr Arg Pro Thr Glu Lys Gln Tyr Glu Thr
            100                 105                 110 ctc gaa aat caa tta gcc ttt tta tgc caa caa ggt ttt tca cta gag    384
Leu Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc    432
Asn Ala Leu Tyr Ala Leu Ser Ala Val Gly His Phe Thr Leu Gly Cys
    130                 135                 140
```

```
gta ttg gaa gat caa gag cat caa gtc gct aaa gaa gaa agg gaa aca        480
Val Leu Glu Asp Gln Glu His Gln Val Ala Lys Glu Glu Arg Glu Thr
145                 150                 155                 160 cct act act gat agt atg ccg cca tta tta cga caa gct atc gaa tta        528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg        576
Phe Asp His Gln Gly Ala Glu Pro Ala Phe Leu Phe Gly Leu Glu Leu
            180                 185                 190 atc ata tgc gga tta gaa aaa caa ctt aaa tgt aaa agt ggg tcc gcg        624
Ile Ile Cys Gly Leu Glu Lys Gln Leu Lys Cys Lys Ser Gly Ser Ala
        195                 200                 205 tac agc cgc gcg cgt acg aaa aac aat tac ggg tct acc atc gag ggc        672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg        720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg        768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac        816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat        864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc        912
Leu Asp Met Leu Gly Asp Gly Asp Ser Pro Gly Pro Gly Phe Thr Pro
    290                 295                 300 cac gac tcc gcc ccc tac ggc gct ctg gat atg gcc gac ttc gag ttt        960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag      1008
Glu Gln Met Phe Thr Asp Ala Leu Gly Ile Asp Glu Tyr Gly Gly
                325                 330                 335

<210> SEQ ID NO 21
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 21

Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
        50                  55                  60

Thr His Phe Cys Pro Leu Glu Gly Glu Ser Trp Gln Asp Phe Leu Arg
 65                 70                  75                  80

Asn Asn Ala Lys Ser Phe Arg Cys Ala Leu Leu Ser His Arg Asp Gly
                85                  90                  95

Ala Lys Glu His Leu Gly Thr Arg Pro Thr Glu Lys Gln Tyr Glu Thr
```

```
            100                 105                 110
Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Asp Gln Glu His Gln Val Ala Lys Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Lys Ser Gly Ser Ala
            195                 200                 205

Tyr Ser Arg Ala Arg Thr Lys Asn Asn Tyr Gly Ser Thr Ile Glu Gly
        210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
                260                 265                 270

Gly Glu Asp Val Ala Met Ala His Ala Asp Ala Leu Asp Asp Phe Asp
            275                 280                 285

Leu Asp Met Leu Gly Asp Gly Asp Ser Pro Gly Pro Gly Phe Thr Pro
        290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 22
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 22 atg tct aga tta gat aaa agt aaa gtg att aac agc gca tta gag ctg    48
Met Ser Arg Leu Asp Lys Ser Lys Val Ile Asn Ser Ala Leu Glu Leu
 1               5                  10                  15 ctt aat gag gtc gga atc gaa ggt tta aca acc cgt aaa ctc gcc cag    96
Leu Asn Glu Val Gly Ile Glu Gly Leu Thr Thr Arg Lys Leu Ala Gln
                20                  25                  30 aag ctt ggt gta gag cag cct aca ctg tat tgg cat gta aaa aat aag   144
Lys Leu Gly Val Glu Gln Pro Thr Leu Tyr Trp His Val Lys Asn Lys
            35                  40                  45 cgg gct ttg ctc gac gcc tta gcc att gag atg tta gat agg cac cat   192
Arg Ala Leu Leu Asp Ala Leu Ala Ile Glu Met Leu Asp Arg His His
        50                  55                  60 act cac ttt tgc cct tta aaa ggg gaa agc tgg caa gat ttt tta cgc   240
Thr His Phe Cys Pro Leu Lys Gly Glu Ser Trp Gln Asp Phe Leu Arg
65                  70                  75                  80 aat aac gct aaa agt ttt aga tgt gct tta cta agt cat cgc aat gga   288
Asn Asn Ala Lys Ser Phe Arg Cys Ala Leu Leu Ser His Arg Asn Gly
```

|  |  |  |  |  |  |  |  |  |  |  |  |  |
|---|---|---|---|---|---|---|---|---|---|---|---|---|
| | | | | 85 | | | | 90 | | | 95 | |
| gca | aaa | gta | cat | tca | gat | aca | cgg | cct | aca | gaa | aaa | cag | tat | gaa | act | 336 |
| Ala | Lys | Val | His | Ser | Asp | Thr | Arg | Pro | Thr | Glu | Lys | Gln | Tyr | Glu | Thr | |
| | | | 100 | | | | | 105 | | | | | 110 | | | |

```
gca aaa gta cat tca gat aca cgg cct aca gaa aaa cag tat gaa act    336
Ala Lys Val His Ser Asp Thr Arg Pro Thr Glu Lys Gln Tyr Glu Thr
            100                 105                 110 ctc gaa aat caa tta gcc ttt tta tgc caa caa ggt ttt tca cta gag    384
Leu Glu Asn Gln Leu Ala Phe Leu Cys Gln Gln Gly Phe Ser Leu Glu
        115                 120                 125 aac gcg tta tat gca ctc agc gct gtg ggg cat ttt act tta ggt tgc    432
Asn Ala Leu Tyr Ala Leu Ser Ala Val Gly His Phe Thr Leu Gly Cys
    130                 135                 140 gta ttg gaa gat caa gag cat caa gtc gct aaa gaa gaa agg gaa aca    480
Val Leu Glu Asp Gln Glu His Gln Val Ala Lys Glu Glu Arg Glu Thr
145                 150                 155                 160 cct act act gat agt atg ccg cca tta tta cga caa gct atc gaa tta    528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg    576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg    624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc    672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg    720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg    768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac    816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat    864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc    912
Leu Asp Met Leu Gly Asp Gly Asp Ser Pro Gly Pro Gly Phe Thr Pro
    290                 295                 300 cac gac tcc gcc ccc tac ggc gct ctg gat atg gcc gac ttc gag ttt    960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag   1008
Glu Gln Met Phe Thr Asp Ala Leu Gly Ile Asp Glu Tyr Gly Gly
                325                 330                 335

<210> SEQ ID NO 23
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 23

Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
            20                  25                  30
```

```
Lys Leu Gly Val Glu Gln Pro Thr Leu Tyr Trp His Val Lys Asn Lys
             35                  40                  45

Arg Ala Leu Leu Asp Ala Leu Ala Ile Glu Met Leu Asp Arg His His
         50                  55                  60

Thr His Phe Cys Pro Leu Lys Gly Glu Ser Trp Gln Asp Phe Leu Arg
 65                  70                  75                  80

Asn Asn Ala Lys Ser Phe Arg Cys Ala Leu Leu Ser His Arg Asn Gly
                 85                  90                  95

Ala Lys Val His Ser Asp Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 24
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 24 atg tct aga tta gat aaa agt aaa gtg att aac agc gca tta gag ctg      48
Met Ser Arg Leu Asp Lys Ser Lys Val Ile Asn Ser Ala Leu Glu Leu
 1               5                  10                  15 ctt aat gag gtc gga atc gaa ggt tta aca acc cgt aaa ctc gcc cag      96
Leu Asn Glu Val Gly Ile Glu Gly Leu Thr Thr Arg Lys Leu Ala Gln
                20                  25                  30 aag cta ggt gta gag cag cct aca ttg tat tgg cat gta aaa aat aag     144
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Lys | Leu | Gly | Val | Glu | Gln | Pro | Thr | Leu | Tyr | Trp | His | Val | Lys | Asn | Lys |     |
|     |     | 35  |     |     |     |     | 40  |     |     |     |     | 45  |     |     |     |     |

| cgg | gct | ttg | ctc | gac | gcc | tta | gcc | att | gag | atg | tta | gat | agg | cac | cat | 192 |
| --- | --- | --- | --- | --- | --- | --- | --- | --- | --- | --- | --- | --- | --- | --- | --- | --- |
| Arg | Ala | Leu | Leu | Asp | Ala | Leu | Ala | Ile | Glu | Met | Leu | Asp | Arg | His | His |     |
|     | 50  |     |     |     |     | 55  |     |     |     |     | 60  |     |     |     |     |     |

| act | cac | ttt | tgc | cct | tta | gaa | ggg | gaa | agc | tgg | caa | gat | ttt | tta | cgt | 240 |
| --- | --- | --- | --- | --- | --- | --- | --- | --- | --- | --- | --- | --- | --- | --- | --- | --- |
| Thr | His | Phe | Cys | Pro | Leu | Glu | Gly | Glu | Ser | Trp | Gln | Asp | Phe | Leu | Arg |     |
| 65  |     |     |     |     | 70  |     |     |     |     | 75  |     |     |     |     | 80  |     |

| aat | aac | gct | aaa | agt | ttt | aga | tgt | gct | tta | cta | agt | cat | cgc | gat | gga | 288 |
| --- | --- | --- | --- | --- | --- | --- | --- | --- | --- | --- | --- | --- | --- | --- | --- | --- |
| Asn | Asn | Ala | Lys | Ser | Phe | Arg | Cys | Ala | Leu | Leu | Ser | His | Arg | Asp | Gly |     |
|     |     |     |     | 85  |     |     |     |     | 90  |     |     |     |     | 95  |     |     |

| gca | aaa | gta | cat | tta | ggt | aca | cgg | cct | aca | gaa | aaa | cag | tat | gaa | act | 336 |
| --- | --- | --- | --- | --- | --- | --- | --- | --- | --- | --- | --- | --- | --- | --- | --- | --- |
| Ala | Lys | Val | His | Leu | Gly | Thr | Arg | Pro | Thr | Glu | Lys | Gln | Tyr | Glu | Thr |     |
|     |     |     | 100 |     |     |     |     | 105 |     |     |     |     | 110 |     |     |     |

| ctc | gaa | aat | caa | tta | gcc | ttt | tta | tgc | caa | caa | ggt | ttt | tca | cta | gag | 384 |
| --- | --- | --- | --- | --- | --- | --- | --- | --- | --- | --- | --- | --- | --- | --- | --- | --- |
| Leu | Glu | Asn | Gln | Leu | Ala | Phe | Leu | Cys | Gln | Gln | Gly | Phe | Ser | Leu | Glu |     |
|     |     | 115 |     |     |     |     | 120 |     |     |     |     | 125 |     |     |     |     |

| aat | gca | tta | tat | gca | ctc | agc | gct | gtg | ggg | cat | ttt | act | tta | ggt | tgc | 432 |
| --- | --- | --- | --- | --- | --- | --- | --- | --- | --- | --- | --- | --- | --- | --- | --- | --- |
| Asn | Ala | Leu | Tyr | Ala | Leu | Ser | Ala | Val | Gly | His | Phe | Thr | Leu | Gly | Cys |     |
| 130 |     |     |     |     | 135 |     |     |     |     | 140 |     |     |     |     |     |     |

| gta | ttg | gaa | gat | caa | gag | cat | caa | gtc | gct | aaa | gaa | gaa | agg | gaa | aca | 480 |
| --- | --- | --- | --- | --- | --- | --- | --- | --- | --- | --- | --- | --- | --- | --- | --- | --- |
| Val | Leu | Glu | Asp | Gln | Glu | His | Gln | Val | Ala | Lys | Glu | Glu | Arg | Glu | Thr |     |
| 145 |     |     |     |     | 150 |     |     |     |     | 155 |     |     |     |     | 160 |     |

| cct | act | act | gat | agt | atg | ccg | cca | tta | tta | cga | caa | gct | atc | gaa | tta | 528 |
| --- | --- | --- | --- | --- | --- | --- | --- | --- | --- | --- | --- | --- | --- | --- | --- | --- |
| Pro | Thr | Thr | Asp | Ser | Met | Pro | Pro | Leu | Leu | Arg | Gln | Ala | Ile | Glu | Leu |     |
|     |     |     |     | 165 |     |     |     |     | 170 |     |     |     |     | 175 |     |     |

| ttt | gat | cac | caa | ggt | gca | gag | cca | gcc | ttc | tta | ttc | ggc | ctt | gaa | ttg | 576 |
| --- | --- | --- | --- | --- | --- | --- | --- | --- | --- | --- | --- | --- | --- | --- | --- | --- |
| Phe | Asp | His | Gln | Gly | Ala | Glu | Pro | Ala | Phe | Leu | Phe | Gly | Leu | Glu | Leu |     |
|     |     |     | 180 |     |     |     |     | 185 |     |     |     |     | 190 |     |     |     |

| atc | ata | tgc | gga | tta | gaa | aaa | caa | ctt | aaa | tgt | gaa | agt | ggg | tcc | gcg | 624 |
| --- | --- | --- | --- | --- | --- | --- | --- | --- | --- | --- | --- | --- | --- | --- | --- | --- |
| Ile | Ile | Cys | Gly | Leu | Glu | Lys | Gln | Leu | Lys | Cys | Glu | Ser | Gly | Ser | Ala |     |
|     |     |     | 195 |     |     |     |     | 200 |     |     |     |     | 205 |     |     |     |

| tac | agc | cgc | gcg | cgt | acg | aaa | aac | aat | tac | ggg | tct | acc | atc | gag | ggc | 672 |
| --- | --- | --- | --- | --- | --- | --- | --- | --- | --- | --- | --- | --- | --- | --- | --- | --- |
| Tyr | Ser | Arg | Ala | Arg | Thr | Lys | Asn | Asn | Tyr | Gly | Ser | Thr | Ile | Glu | Gly |     |
|     | 210 |     |     |     |     | 215 |     |     |     |     | 220 |     |     |     |     |     |

| ctg | ctc | gat | ctc | ccg | gac | gac | gac | gcc | ccc | gaa | gag | gcg | ggg | ctg | gcg | 720 |
| --- | --- | --- | --- | --- | --- | --- | --- | --- | --- | --- | --- | --- | --- | --- | --- | --- |
| Leu | Leu | Asp | Leu | Pro | Asp | Asp | Asp | Ala | Pro | Glu | Glu | Ala | Gly | Leu | Ala |     |
| 225 |     |     |     |     | 230 |     |     |     |     | 235 |     |     |     |     | 240 |     |

| gct | ccg | cgc | ctg | tcc | ttt | ctc | ccc | gcg | gga | cac | acg | cgc | aga | ctg | tcg | 768 |
| --- | --- | --- | --- | --- | --- | --- | --- | --- | --- | --- | --- | --- | --- | --- | --- | --- |
| Ala | Pro | Arg | Leu | Ser | Phe | Leu | Pro | Ala | Gly | His | Thr | Arg | Arg | Leu | Ser |     |
|     |     |     |     | 245 |     |     |     |     | 250 |     |     |     |     | 255 |     |     |

| acg | gcc | ccc | ccg | acc | gat | gtc | agc | ctg | ggg | gac | gag | ctc | cac | tta | gac | 816 |
| --- | --- | --- | --- | --- | --- | --- | --- | --- | --- | --- | --- | --- | --- | --- | --- | --- |
| Thr | Ala | Pro | Pro | Thr | Asp | Val | Ser | Leu | Gly | Asp | Glu | Leu | His | Leu | Asp |     |
|     |     |     | 260 |     |     |     |     | 265 |     |     |     |     | 270 |     |     |     |

| ggc | gag | gac | gtg | gcg | atg | gcg | cat | gcc | gac | gcg | cta | gac | gat | ttc | gat | 864 |
| --- | --- | --- | --- | --- | --- | --- | --- | --- | --- | --- | --- | --- | --- | --- | --- | --- |
| Gly | Glu | Asp | Val | Ala | Met | Ala | His | Ala | Asp | Ala | Leu | Asp | Asp | Phe | Asp |     |
|     |     | 275 |     |     |     |     | 280 |     |     |     |     | 285 |     |     |     |     |

| ctg | gac | atg | ttg | ggg | gac | ggg | gat | tcc | ccg | ggt | ccg | gga | ttt | acc | ccc | 912 |
| --- | --- | --- | --- | --- | --- | --- | --- | --- | --- | --- | --- | --- | --- | --- | --- | --- |
| Leu | Asp | Met | Leu | Gly | Asp | Gly | Asp | Ser | Pro | Gly | Pro | Gly | Phe | Thr | Pro |     |
|     | 290 |     |     |     |     | 295 |     |     |     |     | 300 |     |     |     |     |     |

| cac | gac | tcc | gcc | ccc | tac | ggc | gct | ctg | gat | atg | gcc | gac | ttc | gag | ttt | 960 |
| --- | --- | --- | --- | --- | --- | --- | --- | --- | --- | --- | --- | --- | --- | --- | --- | --- |
| His | Asp | Ser | Ala | Pro | Tyr | Gly | Ala | Leu | Asp | Met | Ala | Asp | Phe | Glu | Phe |     |
| 305 |     |     |     |     | 310 |     |     |     |     | 315 |     |     |     |     | 320 |     |

| gag | cag | atg | ttt | acc | gat | gcc | ctt | gga | att | gac | gag | tac | ggt | ggg | tag | 1008 |
| --- | --- | --- | --- | --- | --- | --- | --- | --- | --- | --- | --- | --- | --- | --- | --- | ---  |
| Glu | Gln | Met | Phe | Thr | Asp | Ala | Leu | Gly | Ile | Asp | Glu | Tyr | Gly | Gly |     |      |
|     |     |     |     | 325 |     |     |     |     | 330 |     |     |     |     | 335 |     |      |

<210> SEQ ID NO 25
<211> LENGTH: 335
<212> TYPE: PRT

<213> ORGANISM: Artificial Sequence
<220> FEATURE:
<223> OTHER INFORMATION: Description of Artificial Sequence: fusion
    protein

<400> SEQUENCE: 25

Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 26
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS

<222> LOCATION: (1)..(1005)

<400> SEQUENCE: 26

```
atg tct aga tta gat aaa agt aaa gtg att aac agc gca tta gag ctg      48
Met Ser Arg Leu Asp Lys Ser Lys Val Ile Asn Ser Ala Leu Glu Leu
 1               5                  10                  15 ctt aat gag gtc gga atc gaa ggt tta aca acc cgt aaa ctc gcc cag      96
Leu Asn Glu Val Gly Ile Glu Gly Leu Thr Thr Arg Lys Leu Ala Gln
             20                  25                  30 aag cta ggt gta gag cag cct aca ttg tat tgg cat gta aaa aat aag     144
Lys Leu Gly Val Glu Gln Pro Thr Leu Tyr Trp His Val Lys Asn Lys
         35                  40                  45 cgg gct ttg ctc gac gcc tta gcc att gag atg tta gat agg cac cat     192
Arg Ala Leu Leu Asp Ala Leu Ala Ile Glu Met Leu Asp Arg His His
     50                  55                  60 act cac ttt tgc cct tta gaa ggg gaa agc tgg caa gat ttt tta cgt     240
Thr His Phe Cys Pro Leu Glu Gly Glu Ser Trp Gln Asp Phe Leu Arg
 65                  70                  75                  80 aat aac gct aaa agt ttt aga tgt gct tta cta agt cat cgc gat gga     288
Asn Asn Ala Lys Ser Phe Arg Cys Ala Leu Leu Ser His Arg Asp Gly
                 85                  90                  95 gca aaa gta cat tta ggt aca cgg cct aca gaa aaa cag tat gaa act     336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag     384
Leu Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc     432
Asn Ala Leu Tyr Ala Leu Ser Ala Val Gly His Phe Thr Leu Gly Cys
    130                 135                 140 gta ttg gaa gat caa gag cat caa gtc gct aaa gaa gaa agg gaa aca     480
Val Leu Glu Asp Gln Glu His Gln Val Ala Lys Glu Glu Arg Glu Thr
145                 150                 155                 160 cct act act gat agt atg tcg cca tta tta cga caa gct atc gaa tta     528
Pro Thr Thr Asp Ser Met Ser Pro Leu Leu Arg Gln Ala Ile Glu Leu
                165                 170                 175 ttt gat cac caa ggt gca gag cca gcc ttc tta ttc ggc ctt gaa ttg     576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg     624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc     672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg     720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg     768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac     816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat     864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc     912
Leu Asp Met Leu Gly Asp Gly Asp Ser Pro Gly Pro Gly Phe Thr Pro
    290                 295                 300
```

```
cac gac tcc gcc ccc tac ggc gct ctg gat atg gcc gac ttc gag ttt    960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag   1008
Glu Gln Met Phe Thr Asp Ala Leu Gly Ile Asp Glu Tyr Gly Gly
                325                 330                 335
```

<210> SEQ ID NO 27
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 27

```
Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
             20                  25                  30

Lys Leu Gly Val Glu Gln Pro Thr Leu Tyr Trp His Val Lys Asn Lys
         35                  40                  45

Arg Ala Leu Leu Asp Ala Leu Ala Ile Glu Met Leu Asp Arg His His
     50                  55                  60

Thr His Phe Cys Pro Leu Glu Gly Glu Ser Trp Gln Asp Phe Leu Arg
 65                  70                  75                  80

Asn Asn Ala Lys Ser Phe Arg Cys Ala Leu Leu Ser His Arg Asp Gly
                 85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Ser Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320
```

```
                            Glu Gln Met Phe Thr Asp Ala Leu Gly Ile Asp Glu Tyr Gly Gly
                                            325                 330                 335

<210> SEQ ID NO 28
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 28 atg tct aga tta gat aaa agt aaa gtg att aac agc gca tta gag ctg      48
Met Ser Arg Leu Asp Lys Ser Lys Val Ile Asn Ser Ala Leu Glu Leu
  1               5                  10                  15 ctt aat gag gtc gga atc gaa ggt tta aca acc cgt aaa ctc gcc cag      96
Leu Asn Glu Val Gly Ile Glu Gly Leu Thr Thr Arg Lys Leu Ala Gln
             20                  25                  30 aag cta ggt gta gag cag cct aca ttg tat tgg cat gta aaa aat aag     144
Lys Leu Gly Val Glu Gln Pro Thr Leu Tyr Trp His Val Lys Asn Lys
         35                  40                  45 cgg gct ttg ctc gac gcc tta gcc att gag atg tta gat agg cac cat     192
Arg Ala Leu Leu Asp Ala Leu Ala Ile Glu Met Leu Asp Arg His His
     50                  55                  60 act cac ttt tgc cct tta gaa ggg gaa agc tgg caa gat ttt tta cgt     240
Thr His Phe Cys Pro Leu Glu Gly Glu Ser Trp Gln Asp Phe Leu Arg
 65                  70                  75                  80 aat aac gct aaa agt ttt aga tgt gct tta cta agt cat cgc gat gga     288
Asn Asn Ala Lys Ser Phe Arg Cys Ala Leu Leu Ser His Arg Asp Gly
                 85                  90                  95 gca aaa gta cat tta ggt aca cgg cct aca gaa aaa cag tat gaa act     336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag     384
Leu Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc     432
Asn Ala Leu Tyr Ala Leu Ser Ala Val Gly His Phe Thr Leu Gly Cys
    130                 135                 140 gta ttg gaa gat caa gag cat caa gtc gct aaa gaa gaa agg gaa aca     480
Val Leu Glu Asp Gln Glu His Gln Val Ala Lys Glu Glu Arg Glu Thr
145                 150                 155                 160 cct act act gat agt atg ccg cca tta tta cga caa gct atc gaa tta     528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg     576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg     624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc     672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg     720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg     768
Ala Pro Arg Leu Ser Phe Leu Pro Ala Gly His Thr Arg Arg Leu Ser
```

```
                    245                 250                 255
acg gcc ccc ccg acc gat gtc agc ctg ggg gac gag ctc cac tta gac      816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat      864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc      912
Leu Asp Met Leu Gly Asp Gly Asp Ser Pro Gly Pro Gly Phe Thr Pro
        290                 295                 300 cac gac tcc gcc ccc tac ggc gct ctg gat atg gcc gac ttc gag ttt      960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag     1008
Glu Gln Met Phe Thr Asp Ala Leu Gly Ile Asp Glu Tyr Gly Gly
                325                 330                 335

<210> SEQ ID NO 29
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 29

Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
```

```
                 245                 250                 255
Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 30
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 30 atg tct aga tta gat aaa agt aaa gtg att aac agc gca tta gag ctg    48
Met Ser Arg Leu Asp Lys Ser Lys Val Ile Asn Ser Ala Leu Glu Leu
1               5                   10                  15 ctt aat gag gtc gga atc gaa ggt tta aca acc cgt aaa ctc gcc cag    96
Leu Asn Glu Val Gly Ile Glu Gly Leu Thr Thr Arg Lys Leu Ala Gln
            20                  25                  30 aag cta ggt gta gag cag cct aca ttg tat tgg cat gta aaa aat aag   144
Lys Leu Gly Val Glu Gln Pro Thr Leu Tyr Trp His Val Lys Asn Lys
        35                  40                  45 cgg gct ttg ctc gac gcc tta gcc att gag atg tta gat agg cac cat   192
Arg Ala Leu Leu Asp Ala Leu Ala Ile Glu Met Leu Asp Arg His His
    50                  55                  60 act cac ttt tgc cct tta gaa ggg gaa agc tgg caa gat tct tta cgt   240
Thr His Phe Cys Pro Leu Glu Gly Glu Ser Trp Gln Asp Ser Leu Arg
65                  70                  75                  80 aat aac gct aaa agt ttt aga tgt gct tta cta agt cat cgc gat gga   288
Asn Asn Ala Lys Ser Phe Arg Cys Ala Leu Leu Ser His Arg Asp Gly
                85                  90                  95 gca aaa gta cat tta ggt aca cgg cct aca gaa aaa cag tat gaa act   336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag   384
Leu Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc   432
Asn Ala Leu Tyr Ala Leu Ser Ala Val Gly His Phe Thr Leu Gly Cys
    130                 135                 140 gta ttg gaa gat caa gag cat caa gtc gct aaa gaa gaa agg gaa aca   480
Val Leu Glu Asp Gln Glu His Gln Val Ala Lys Glu Glu Arg Glu Thr
145                 150                 155                 160 cct act act gat agt atg ccg cca tta tta cga caa gct atc gaa tta   528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg   576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg   624
```

```
                Ile Ile Cys Gly Leu Glu Lys Gln Leu Lys Cys Glu Ser Gly Ser Ala
                        195                 200                 205 tac agc cgc gcg cgt acg aaa aac aat tac ggg tct acc atc gag ggc      672
Tyr Ser Arg Ala Arg Thr Lys Asn Asn Tyr Gly Ser Thr Ile Glu Gly
210                 215                 220 ctg ctc gat ctc ccg gac gac gac gcc ccc gaa gag gcg ggg ctg gcg      720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg      768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac      816
Thr Ala Pro Pro Thr Asp Val Ser Leu Gly Asp Glu Leu His Leu Asp
                260                 265                 270 ggc gag gac gtg gcg atg gcg cat gcc gac gcg cta gac gat ttc gat      864
Gly Glu Asp Val Ala Met Ala His Ala Asp Ala Leu Asp Asp Phe Asp
                275                 280                 285 ctg gac atg ttg ggg gac ggg gat tcc ccg ggt ccg gga ttt acc ccc      912
Leu Asp Met Leu Gly Asp Gly Asp Ser Pro Gly Pro Gly Phe Thr Pro
                290                 295                 300 cac gac tcc gcc ccc tac ggc gct ctg gat atg gcc gac ttc gag ttt      960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag     1008
Glu Gln Met Phe Thr Asp Ala Leu Gly Ile Asp Glu Tyr Gly Gly
                325                 330                 335

<210> SEQ ID NO 31
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 31

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
        50                  55                  60

Thr His Phe Cys Pro Leu Glu Gly Glu Ser Trp Gln Asp Ser Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175
```

```
Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
            195                 200                 205

Tyr Ser Arg Ala Arg Thr Lys Asn Asn Tyr Gly Ser Thr Ile Glu Gly
            210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
            245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
            275                 280                 285

Leu Asp Met Leu Gly Asp Gly Asp Ser Pro Gly Pro Gly Phe Thr Pro
            290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 32
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 32 atg tct aga tta gat aaa agt aaa gtg att aac agc gca tta gag ctg      48
Met Ser Arg Leu Asp Lys Ser Lys Val Ile Asn Ser Ala Leu Glu Leu
  1               5                  10                  15 ctt aat gag gtc gga atc gaa ggt tta aca acc cgt aaa ctc gcc cag      96
Leu Asn Glu Val Gly Ile Glu Gly Leu Thr Thr Arg Lys Leu Ala Gln
                 20                  25                  30 aag cta ggt gta gag cag cct aca ttg tat tgg cat gta aaa aat aag     144
Lys Leu Gly Val Glu Gln Pro Thr Leu Tyr Trp His Val Lys Asn Lys
             35                  40                  45 cgg gct ttg ctc gac gcc tta gcc att gag atg tta gat agg cac cat     192
Arg Ala Leu Leu Asp Ala Leu Ala Ile Glu Met Leu Asp Arg His His
         50                  55                  60 act cac ttt tgc cct tta gaa ggg gaa agc tgg caa gat ttt tta cgt     240
Thr His Phe Cys Pro Leu Glu Gly Glu Ser Trp Gln Asp Phe Leu Arg
 65                  70                  75                  80 aat aac gct aaa agt ttt aga tgt gct tta cta agt cat cgc gat gga     288
Asn Asn Ala Lys Ser Phe Arg Cys Ala Leu Leu Ser His Arg Asp Gly
                 85                  90                  95 gca aaa gta cat tta ggt aca cgg cct aca gaa aaa cag tat gaa act     336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag     384
Leu Glu Asn Gln Leu Ala Phe Leu Cys Gln Gln Gly Phe Ser Leu Glu
        115                 120                 125 aat gca tta tgt gca ctc agc gct gtg ggg cat ttt act tta ggt tgc     432
Asn Ala Leu Cys Ala Leu Ser Ala Val Gly His Phe Thr Leu Gly Cys
    130                 135                 140
```

-continued

```
gta ttg gaa gat caa gag cat caa gtc gct aaa gaa gaa agg gaa aca       480
Val Leu Glu Asp Gln Glu His Gln Val Ala Lys Glu Glu Arg Glu Thr
145                 150                 155                 160 cct act act gat agt atg ccg cca tta tta cga caa gct atc gaa tta       528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg       576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg       624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc       672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg       720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg       768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac       816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat       864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc       912
Leu Asp Met Leu Gly Asp Gly Asp Ser Pro Gly Pro Gly Phe Thr Pro
    290                 295                 300 cac gac tcc gcc ccc tac ggc gct ctg gat atg gcc gac ttc gag ttt       960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag      1008
Glu Gln Met Phe Thr Asp Ala Leu Gly Ile Asp Glu Tyr Gly Gly
                325                 330                 335

<210> SEQ ID NO 33
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 33

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110
```

```
Leu Glu Asn Gln Leu Ala Phe Leu Cys Gln Gln Gly Phe Ser Leu Glu
            115                 120                 125
Asn Ala Leu Cys Ala Leu Ser Ala Val Gly His Phe Thr Leu Gly Cys
        130                 135                 140
Val Leu Glu Asp Gln Glu His Gln Val Ala Lys Glu Glu Arg Glu Thr
145                 150                 155                 160
Pro Thr Thr Asp Ser Met Pro Pro Leu Leu Arg Gln Ala Ile Glu Leu
                165                 170                 175
Phe Asp His Gln Gly Ala Glu Pro Ala Phe Leu Phe Gly Leu Glu Leu
            180                 185                 190
Ile Ile Cys Gly Leu Glu Lys Gln Leu Lys Cys Glu Ser Gly Ser Ala
        195                 200                 205
Tyr Ser Arg Ala Arg Thr Lys Asn Asn Tyr Gly Ser Thr Ile Glu Gly
    210                 215                 220
Leu Leu Asp Leu Pro Asp Asp Ala Pro Glu Glu Ala Gly Leu Ala
225                 230                 235                 240
Ala Pro Arg Leu Ser Phe Leu Pro Ala Gly His Thr Arg Arg Leu Ser
                245                 250                 255
Thr Ala Pro Pro Thr Asp Val Ser Leu Gly Asp Glu Leu His Leu Asp
            260                 265                 270
Gly Glu Asp Val Ala Met Ala His Ala Asp Ala Leu Asp Asp Phe Asp
        275                 280                 285
Leu Asp Met Leu Gly Asp Gly Asp Ser Pro Gly Pro Gly Phe Thr Pro
    290                 295                 300
His Asp Ser Ala Pro Tyr Gly Ala Leu Asp Met Ala Asp Phe Glu Phe
305                 310                 315                 320
Glu Gln Met Phe Thr Asp Ala Leu Gly Ile Asp Glu Tyr Gly Gly
                325                 330                 335

<210> SEQ ID NO 34
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 34 atg tct aga tta gat aaa agt aaa gtg att aac agc gca tta gag ctg     48
Met Ser Arg Leu Asp Lys Ser Lys Val Ile Asn Ser Ala Leu Glu Leu
 1               5                  10                  15 ctt aat gag gtc gga atc gaa ggt tta aca acc cgt aaa ctc gcc cag     96
Leu Asn Glu Val Gly Ile Glu Gly Leu Thr Thr Arg Lys Leu Ala Gln
                20                  25                  30 aag cta ggt gta gag cag cct aca ttg tat tgg cat gta aaa aat aag    144
Lys Leu Gly Val Glu Gln Pro Thr Leu Tyr Trp His Val Lys Asn Lys
            35                  40                  45 cgg gct ttg ctc gac gcc tta gcc att gag atg tta gat agg cac cat    192
Arg Ala Leu Leu Asp Ala Leu Ala Ile Glu Met Leu Asp Arg His His
        50                  55                  60 act cac ttt tgc cct tta gaa ggg gaa agc tgg caa gat ttt tta cgt    240
Thr His Phe Cys Pro Leu Glu Gly Glu Ser Trp Gln Asp Phe Leu Arg
    65                  70                  75                  80 aat aac gct aaa agt ttt aga tgt gct tta cta agt cat cgc gat gga    288
Asn Asn Ala Lys Ser Phe Arg Cys Ala Leu Leu Ser His Arg Asp Gly
                85                  90                  95
```

```
gca aaa gta cat tta ggt aca cgg cct aca gaa aaa cag tgt gaa act    336
Ala Lys Val His Leu Gly Thr Arg Pro Thr Glu Lys Gln Cys Glu Thr
        100                 105                 110 ctc gaa aat caa tta gcc ttt tta tgc caa caa ggt ttt tca cta gag    384
Leu Glu Asn Gln Leu Ala Phe Leu Cys Gln Gln Gly Phe Ser Leu Glu
            115                 120                 125 aat gca tta tat gca ctc agc gct gtg ggg cat ttt act tta ggt tgc    432
Asn Ala Leu Tyr Ala Leu Ser Ala Val Gly His Phe Thr Leu Gly Cys
    130                 135                 140 gta ttg gaa gat caa gag cat caa gtc gct aaa gaa gaa agg gaa aca    480
Val Leu Glu Asp Gln Glu His Gln Val Ala Lys Glu Glu Arg Glu Thr
145                 150                 155                 160 cct act act gat agt atg ccg cca tta tta cga caa gct gtc gaa tta    528
Pro Thr Thr Asp Ser Met Pro Pro Leu Leu Arg Gln Ala Val Glu Leu
                165                 170                 175 ttt gat cac caa ggt gca gag cca gcc ttc tta ttc ggc ctt gaa ttg    576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg    624
Ile Ile Cys Gly Leu Glu Lys Gln Leu Lys Cys Glu Ser Gly Ser Ala
    195                 200                 205 tac agc cgc gcg cgt acg aaa aac aat tac ggg tct acc atc gag ggc    672
Tyr Ser Arg Ala Arg Thr Lys Asn Asn Tyr Gly Ser Thr Ile Glu Gly
210                 215                 220 ctg ctc gat ctc ccg gac gac gac gcc ccc gaa gag gcg ggg ctg gcg    720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg    768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac    816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat    864
Gly Glu Asp Val Ala Met Ala His Ala Asp Ala Leu Asp Asp Phe Asp
    275                 280                 285 ctg gac atg ttg ggg gac ggg gat tcc ccg ggt ccg gga ttt acc ccc    912
Leu Asp Met Leu Gly Asp Gly Asp Ser Pro Gly Pro Gly Phe Thr Pro
290                 295                 300 cac gac tcc gcc ccc tac ggc gct ctg gat atg gcc gac ttc gag ttt    960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag   1008
Glu Gln Met Phe Thr Asp Ala Leu Gly Ile Asp Glu Tyr Gly Gly
                325                 330                 335

<210> SEQ ID NO 35
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 35

Met Ser Arg Leu Asp Lys Ser Lys Val Ile Asn Ser Ala Leu Glu Leu
  1               5                  10                  15

Leu Asn Glu Val Gly Ile Glu Gly Leu Thr Thr Arg Lys Leu Ala Gln
                 20                  25                  30

Lys Leu Gly Val Glu Gln Pro Thr Leu Tyr Trp His Val Lys Asn Lys
```

```
                  35                  40                  45
Arg Ala Leu Leu Asp Ala Leu Ala Ile Glu Met Leu Asp Arg His His
             50                  55                  60

Thr His Phe Cys Pro Leu Glu Gly Glu Ser Trp Gln Asp Phe Leu Arg
 65                  70                  75                  80

Asn Asn Ala Lys Ser Phe Arg Cys Ala Leu Leu Ser His Arg Asp Gly
                 85                  90                  95

Ala Lys Val His Leu Gly Thr Arg Pro Thr Glu Lys Gln Cys Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
130                 135                 140

Val Leu Glu Asp Gln Glu His Gln Val Ala Lys Glu Arg Glu Thr
145                 150                 155                 160

Pro Thr Thr Asp Ser Met Pro Leu Leu Arg Gln Ala Val Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 36
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 36 atg tct aga tta gat aaa agt aaa gtg att aac agc gca tta gag ctg      48
Met Ser Arg Leu Asp Lys Ser Lys Val Ile Asn Ser Ala Leu Glu Leu
 1               5                  10                  15 ctt aat gag gtc gga atc gaa ggt tta aca acc cgt aaa ctc gcc cag     96
Leu Asn Glu Val Gly Ile Glu Gly Leu Thr Thr Arg Lys Leu Ala Gln
            20                  25                  30 aag cta ggt gta gag cag cct aca ttg tat tgg cat gta aaa aat aag    144
Lys Leu Gly Val Glu Gln Pro Thr Leu Tyr Trp His Val Lys Asn Lys
```

```
               35                  40                  45
cgg gct ttg ctc gac gcc tta gcc att gag atg tta gat agg cac cat    192
Arg Ala Leu Leu Asp Ala Leu Ala Ile Glu Met Leu Asp Arg His His
 50                  55                  60 act cac ttt tgc cct tta gaa ggg gaa agc tgg caa gat ttt tta cgt    240
Thr His Phe Cys Pro Leu Glu Gly Glu Ser Trp Gln Asp Phe Leu Arg
 65                  70                  75                  80 aat aac gct aaa agt ttt aga tgt gct tta cta agt cat cgc gat gga    288
Asn Asn Ala Lys Ser Phe Arg Cys Ala Leu Leu Ser His Arg Asp Gly
                 85                  90                  95 gca aaa gta cat tta ggt aca cgg cct aca gaa aaa cag tat gaa act    336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag    384
Leu Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc    432
Asn Ala Leu Tyr Ala Leu Ser Ala Val Gly His Phe Thr Leu Gly Cys
    130                 135                 140 gta ttg gaa gat caa gag cat caa gtc gct aaa gaa gaa agg gaa aca    480
Val Leu Glu Asp Gln Glu His Gln Val Ala Lys Glu Glu Arg Glu Thr
145                 150                 155                 160 cct act act gat agt atg ccg cca tta tta cga caa gct acc gaa tta    528
Pro Thr Thr Asp Ser Met Pro Pro Leu Leu Arg Gln Ala Thr Glu Leu
                165                 170                 175 ttt gat cac caa ggt gca aag cca gcc ttc tta ttc ggc ctt gaa ttg    576
Phe Asp His Gln Gly Ala Lys Pro Ala Phe Leu Phe Gly Leu Glu Leu
            180                 185                 190 atc ata tgc gga tta gaa aaa caa ctt aaa tgt gaa agt ggg tcc gcg    624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc    672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg    720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg    768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac    816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat    864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc    912
Leu Asp Met Leu Gly Asp Gly Asp Ser Pro Gly Pro Gly Phe Thr Pro
    290                 295                 300 cac gac tcc gcc ccc tac ggc gct ctg gat atg gcc gac ttc gag ttt    960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag   1008
Glu Gln Met Phe Thr Asp Ala Leu Gly Ile Asp Glu Tyr Gly Gly
                325                 330                 335

<210> SEQ ID NO 37
<211> LENGTH: 335
<212> TYPE: PRT
<213> ORGANISM: Artificial Sequence
```

```
<220> FEATURE:
<223> OTHER INFORMATION: Description of Artificial Sequence: fusion
      protein

<400> SEQUENCE: 37

Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Thr Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 38
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)
```

<400> SEQUENCE: 38

```
atg tct aga tta gat aaa agt aaa gtg att aac agc gca tta gag ctg      48
Met Ser Arg Leu Asp Lys Ser Lys Val Ile Asn Ser Ala Leu Glu Leu
 1               5                  10                  15 ctt aat gag gtc gga atc gaa ggt tta aca acc cgt aaa ctc gcc cag      96
Leu Asn Glu Val Gly Ile Glu Gly Leu Thr Thr Arg Lys Leu Ala Gln
             20                  25                  30 aag cta ggt gta gag cag cct aca ttg tat tgg cat gta aaa aat aag     144
Lys Leu Gly Val Glu Gln Pro Thr Leu Tyr Trp His Val Lys Asn Lys
         35                  40                  45 cgg gct ttg ctc gac gcc tta gcc att gag atg tta gat agg cac cat     192
Arg Ala Leu Leu Asp Ala Leu Ala Ile Glu Met Leu Asp Arg His His
 50                  55                  60 act cac ttt tgc cct tta gaa ggg gaa agc tgg caa gat ttt tta cgt     240
Thr His Phe Cys Pro Leu Glu Gly Glu Ser Trp Gln Asp Phe Leu Arg
 65                  70                  75                  80 aat aac gct aaa agt ttt aga tgt gct tta cta agt cat cgc gat gga     288
Asn Asn Ala Lys Ser Phe Arg Cys Ala Leu Leu Ser His Arg Asp Gly
                 85                  90                  95 gca aaa gta cat tta ggt aca cgg cct aca gaa aaa cag tat gaa act     336
Ala Lys Val His Leu Gly Thr Arg Pro Thr Glu Lys Gln Tyr Glu Thr
            100                 105                 110 cac gaa aat caa tta gcc ttt tta tgc caa caa ggt ttt tca cta gag     384
His Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc     432
Asn Ala Leu Tyr Ala Leu Ser Ala Val Gly His Phe Thr Leu Gly Cys
130                 135                 140 gta ttg gaa gat caa gag cat caa gtc gct aaa gaa gaa agg gaa aca     480
Val Leu Glu Asp Gln Glu His Gln Val Ala Lys Glu Glu Arg Glu Thr
145                 150                 155                 160 cct act act gat agt atg ccg cca tta tta cga caa gct atc gaa tta     528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg     576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg     624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc     672
Tyr Ser Arg Ala Arg Thr Lys Asn Asn Tyr Gly Ser Thr Ile Glu Gly
210                 215                 220 ctg ctc gat ctc ccg gac gac gac gcc ccc gaa gag gcg ggg ctg gcg     720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg     768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac     816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat     864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc     912
Leu Asp Met Leu Gly Asp Gly Asp Ser Pro Gly Pro Gly Phe Thr Pro
290                 295                 300
```

```
cac gac tcc gcc ccc tac ggc gct ctg gat atg gcc gac ttc gag ttt         960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag        1008
Glu Gln Met Phe Thr Asp Ala Leu Gly Ile Asp Glu Tyr Gly Gly
                325                 330                 335

<210> SEQ ID NO 39
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 39

Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
             20                  25                  30

Lys Leu Gly Val Glu Gln Pro Thr Leu Tyr Trp His Val Lys Asn Lys
         35                  40                  45

Arg Ala Leu Leu Asp Ala Leu Ala Ile Glu Met Leu Asp Arg His His
     50                  55                  60

Thr His Phe Cys Pro Leu Glu Gly Glu Ser Trp Gln Asp Phe Leu Arg
 65                  70                  75                  80

Asn Asn Ala Lys Ser Phe Arg Cys Ala Leu Leu Ser His Arg Asp Gly
                 85                  90                  95

Ala Lys Val His Leu Gly Thr Arg Pro Thr Glu Lys Gln Tyr Glu Thr
            100                 105                 110

His Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320
```

-continued

Glu Gln Met Phe Thr Asp Ala Leu Gly Ile Asp Glu Tyr Gly Gly
              325                 330                 335

<210> SEQ ID NO 40
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 40

```
atg tct aga tta gat aaa agt aaa gtg att aac agc gca tta gag ctg      48
Met Ser Arg Leu Asp Lys Ser Lys Val Ile Asn Ser Ala Leu Glu Leu
 1               5                  10                  15 ctt aat gag gtc gga atc gaa ggt tta aca acc cgt aaa ctc gcc cag      96
Leu Asn Glu Val Gly Ile Glu Gly Leu Thr Thr Arg Lys Leu Ala Gln
             20                  25                  30 aag cta ggt gta gag cag cct aca ttg tat tgg cat gta aaa aat aag     144
Lys Leu Gly Val Glu Gln Pro Thr Leu Tyr Trp His Val Lys Asn Lys
         35                  40                  45 cgg gct ttg ctc gac gcc tta gcc att gag atg tta gat agg cac cat     192
Arg Ala Leu Leu Asp Ala Leu Ala Ile Glu Met Leu Asp Arg His His
     50                  55                  60 act cac ttt tgc cct tta gaa ggg gaa agc tgg caa gat ttt tta cgt     240
Thr His Phe Cys Pro Leu Glu Gly Glu Ser Trp Gln Asp Phe Leu Arg
 65                  70                  75                  80 aat aac gct aaa ggt ttt aga tgt gct tta cta agt cat cgc gat gga     288
Asn Asn Ala Lys Gly Phe Arg Cys Ala Leu Leu Ser His Arg Asp Gly
                 85                  90                  95 gca aaa gta cat tta ggt aca cgg cct aca gaa aaa cag tat gaa act     336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag     384
Leu Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc     432
Asn Ala Leu Tyr Ala Leu Ser Ala Val Gly His Phe Thr Leu Gly Cys
    130                 135                 140 gta ttg gaa gat caa gag cat caa gtc gct aaa gaa gaa agg gaa aca     480
Val Leu Glu Asp Gln Glu His Gln Val Ala Lys Glu Glu Arg Glu Thr
145                 150                 155                 160 cct act act gat agt atg ccg cca tta tta cga caa gct gtc gaa tta     528
Pro Thr Thr Asp Ser Met Pro Pro Leu Leu Arg Gln Ala Val Glu Leu
                165                 170                 175 ttt gat cac caa ggt gca gag cca gcc ttc tta ttc ggc ctt gaa ttg     576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg     624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc     672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg     720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg     768
Ala Pro Arg Leu Ser Phe Leu Pro Ala Gly His Thr Arg Arg Leu Ser
                245                 250                 255
```

```
acg gcc ccc ccg acc gat gtc agc ctg ggg gac gag ctc cac tta gac    816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat    864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc    912
Leu Asp Met Leu Gly Asp Gly Asp Ser Pro Gly Pro Gly Phe Thr Pro
    290                 295                 300 cac gac tcc gcc ccc tac ggc gct ctg gat atg gcc gac ttc gag ttt    960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag   1008
Glu Gln Met Phe Thr Asp Ala Leu Gly Ile Asp Glu Tyr Gly Gly
                325                 330                 335

<210> SEQ ID NO 41
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 41

Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Gly Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Val Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255
```

```
Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
            275                 280                 285

Leu Asp Met Leu Gly Asp Gly Asp Ser Pro Gly Pro Gly Phe Thr Pro
            290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 42
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 42 atg tct aga tta gat aaa agt aaa gtg att aac agc gca tta gag ctg     48
Met Ser Arg Leu Asp Lys Ser Lys Val Ile Asn Ser Ala Leu Glu Leu
 1               5                  10                  15 ctt aat gag gtc gga atc gaa ggt tta aca acc cgt aaa ctc gcc cag    96
Leu Asn Glu Val Gly Ile Glu Gly Leu Thr Thr Arg Lys Leu Ala Gln
                20                  25                  30 aag cta ggt gta gag cag cct aca ttg tat tgg cat gta aaa aat aag    144
Lys Leu Gly Val Glu Gln Pro Thr Leu Tyr Trp His Val Lys Asn Lys
            35                  40                  45 cgg gct ttg ctc gac gcc tta gcc att gag atg tta gat agg cac cat    192
Arg Ala Leu Leu Asp Ala Leu Ala Ile Glu Met Leu Asp Arg His His
        50                  55                  60 act cac ttt tgc cct tta gaa ggg gaa agc tgg caa gat ttt tta cgt    240
Thr His Phe Cys Pro Leu Glu Gly Glu Ser Trp Gln Asp Phe Leu Arg
 65                  70                  75                  80 aat aac gct aaa aga ttt aga tgt gct tta cta agt cat cgc gat gga    288
Asn Asn Ala Lys Arg Phe Arg Cys Ala Leu Leu Ser His Arg Asp Gly
                 85                  90                  95 gca aaa gta cat tta ggt aca cgg cct aca gaa aaa cag tat gaa act    336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag    384
Leu Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc    432
Asn Ala Leu Tyr Ala Leu Ser Ala Val Gly His Phe Thr Leu Gly Cys
    130                 135                 140 gta ttg gaa gat caa gag cat caa gtc gct aaa gaa gaa agg gaa aca    480
Val Leu Glu Asp Gln Glu His Gln Val Ala Lys Glu Glu Arg Glu Thr
145                 150                 155                 160 cct act act gat agt atg ccg cca tta tta cga caa gct atc gaa tta    528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg    576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg    624
Ile Ile Cys Gly Leu Glu Lys Gln Leu Lys Cys Glu Ser Gly Ser Ala
```

```
                195                 200                 205
tac agc cgc gcg cgt acg aaa aac aat tac ggg tct acc atc gag ggc      672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg      720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg      768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac      816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat      864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc      912
Leu Asp Met Leu Gly Asp Gly Asp Ser Pro Gly Pro Gly Phe Thr Pro
    290                 295                 300 cac gac tcc gcc ccc tac ggc gct ctg gat atg gcc gac ttc gag ttt      960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag     1008
Glu Gln Met Phe Thr Asp Ala Leu Gly Ile Asp Glu Tyr Gly Gly
                325                 330                 335

<210> SEQ ID NO 43
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 43

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Arg Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
```

```
                    180                 185                 190
Ile Ile Cys Gly Leu Glu Lys Gln Leu Lys Cys Glu Ser Gly Ser Ala
            195                 200                 205

Tyr Ser Arg Ala Arg Thr Lys Asn Asn Tyr Gly Ser Thr Ile Glu Gly
        210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Leu Ser
            245                 250                 255

Thr Ala Pro Pro Thr Asp Val Ser Leu Gly Asp Glu Leu His Leu Asp
        260                 265                 270

Gly Glu Asp Val Ala Met Ala His Ala Asp Ala Leu Asp Asp Phe Asp
    275                 280                 285

Leu Asp Met Leu Gly Asp Gly Asp Ser Pro Gly Pro Gly Phe Thr Pro
290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
            325                 330                 335

<210> SEQ ID NO 44
<211> LENGTH: 1008
<212> TYPE: DNA
<213> ORGANISM: Artificial Sequence
<220> FEATURE:
<223> OTHER INFORMATION: Description of Artificial Sequence: hybrid gene
<220> FEATURE:
<221> NAME/KEY: CDS
<222> LOCATION: (1)..(1005)

<400> SEQUENCE: 44 atg tct aga tta gat aaa agt aaa gtg att aac agc gca tta gag ctg      48
Met Ser Arg Leu Asp Lys Ser Lys Val Ile Asn Ser Ala Leu Glu Leu
  1               5                  10                  15 ctt aat gag gtc gga atc gaa ggt tta aca acc cgt aaa ctc gcc cag      96
Leu Asn Glu Val Gly Ile Glu Gly Leu Thr Thr Arg Lys Leu Ala Gln
                 20                  25                  30 aag cta ggt gta gag cag cct aca ttg tat tgg cat gta aaa aat aag     144
Lys Leu Gly Val Glu Gln Pro Thr Leu Tyr Trp His Val Lys Asn Lys
             35                  40                  45 cgg gct ttg ctc gac gcc tta gtc att gag atg tta gat agg cac cat     192
Arg Ala Leu Leu Asp Ala Leu Val Ile Glu Met Leu Asp Arg His His
     50                  55                  60 act cac ttt tgc cct tta gaa ggg gaa agc tgg caa gat ttt tta cgt     240
Thr His Phe Cys Pro Leu Glu Gly Glu Ser Trp Gln Asp Phe Leu Arg
 65                  70                  75                  80 aat aac gct aaa agt ttt aga tgt gct tta cta agt cat cgc gat gga     288
Asn Asn Ala Lys Ser Phe Arg Cys Ala Leu Leu Ser His Arg Asp Gly
                 85                  90                  95 gca aaa gta cat tta ggt aca cgg cct aca gaa aaa cag tat gaa act     336
Ala Lys Val His Leu Gly Thr Arg Pro Thr Glu Lys Gln Tyr Glu Thr
            100                 105                 110 ctc gaa aat caa tta gcc ttt tta tgc caa caa ggt ttt tca cta gag     384
Leu Glu Asn Gln Leu Ala Phe Leu Cys Gln Gln Gly Phe Ser Leu Glu
        115                 120                 125 aat gca tta tat gca ctc agc gct gtg ggg cat ttt act tta ggt tgc     432
Asn Ala Leu Tyr Ala Leu Ser Ala Val Gly His Phe Thr Leu Gly Cys
    130                 135                 140 gta ttg gaa gat caa gag cat caa gtc gct aaa gaa gaa agg gaa aca     480
```

```
Val Leu Glu Asp Gln Glu His Gln Val Ala Lys Glu Glu Arg Glu Thr
145                 150                 155                 160 cct act act gat agt atg ccg cca tta tta cga caa gct atc gaa tta    528
Pro Thr Thr Asp Ser Met Pro Pro Leu Leu Arg Gln Ala Ile Glu Leu
                165                 170                 175 ttt gat cac caa ggt gca gag cca gcc ttc tta ttc ggc ctt gaa ttg    576
Phe Asp His Gln Gly Ala Glu Pro Ala Phe Leu Phe Gly Leu Glu Leu
            180                 185                 190 atc ata tgc gga tta gaa aaa caa ctt aaa tgt gaa agt ggg tcc gcg    624
Ile Ile Cys Gly Leu Glu Lys Gln Leu Lys Cys Glu Ser Gly Ser Ala
        195                 200                 205 tac agc cgc gcg cgt acg aaa aac aat tac ggg tct acc atc gag ggc    672
Tyr Ser Arg Ala Arg Thr Lys Asn Asn Tyr Gly Ser Thr Ile Glu Gly
    210                 215                 220 ctg ctc gat ctc ccg gac gac gac gcc ccc gaa gag gcg ggg ctg gcg    720
Leu Leu Asp Leu Pro Asp Asp Asp Ala Pro Glu Glu Ala Gly Leu Ala
225                 230                 235                 240 gct ccg cgc ctg tcc ttt ctc ccc gcg gga cac acg cgc aga ctg tcg    768
Ala Pro Arg Leu Ser Phe Leu Pro Ala Gly His Thr Arg Arg Leu Ser
                245                 250                 255 acg gcc ccc ccg acc gat gtc agc ctg ggg gac gag ctc cac tta gac    816
Thr Ala Pro Pro Thr Asp Val Ser Leu Gly Asp Glu Leu His Leu Asp
            260                 265                 270 ggc gag gac gtg gcg atg gcg cat gcc gac gcg cta gac gat ttc gat    864
Gly Glu Asp Val Ala Met Ala His Ala Asp Ala Leu Asp Asp Phe Asp
        275                 280                 285 ctg gac atg ttg ggg gac ggg gat tcc ccg ggt ccg gga ttt acc ccc    912
Leu Asp Met Leu Gly Asp Gly Asp Ser Pro Gly Pro Gly Phe Thr Pro
    290                 295                 300 cac gac tcc gcc ccc tac ggc gct ctg gat atg gcc gac ttc gag ttt    960
His Asp Ser Ala Pro Tyr Gly Ala Leu Asp Met Ala Asp Phe Glu Phe
305                 310                 315                 320 gag cag atg ttt acc gat gcc ctt gga att gac gag tac ggt ggg tag   1008
Glu Gln Met Phe Thr Asp Ala Leu Gly Ile Asp Glu Tyr Gly Gly
                325                 330                 335

<210> SEQ ID NO 45
<211> LENGTH: 335
<212> TYPE: PRT
<213> ORGANISM: Artificial Sequence
<220> FEATURE:
<223> OTHER INFORMATION: Description of Artificial Sequence: fusion
      protein

<400> SEQUENCE: 45

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Val Ile Glu Met Leu Asp Arg His His
        50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110
```

-continued

```
Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
                180                 185                 190

Ile Ile Cys Gly Leu Glu Lys Gln Leu Lys Cys Glu Ser Gly Ser Ala
                195                 200                 205

Tyr Ser Arg Ala Arg Thr Lys Asn Asn Tyr Gly Ser Thr Ile Glu Gly
        210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
                260                 265                 270

Gly Glu Asp Val Ala Met Ala His Ala Asp Ala Leu Asp Asp Phe Asp
                275                 280                 285

Leu Asp Met Leu Gly Asp Gly Asp Ser Pro Gly Pro Gly Phe Thr Pro
                290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 46
gaccgatcca gcctccgcgg                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 47
cgtgtgtccc gcggggagaa                                              20
```